United States Patent
Melis et al.

(10) Patent No.: US 12,391,950 B2
(45) Date of Patent: *Aug. 19, 2025

(54) FUSION CONSTRUCTS AS PROTEIN OVER-EXPRESSION VECTORS

(71) Applicant: The Regents of the University of California, Oakland, CA (US)

(72) Inventors: Anastasios Melis, El Cerrito, CA (US); Cinzia Formighieri, Saugus, MA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/544,275

(22) Filed: Dec. 18, 2023

(65) Prior Publication Data

US 2024/0150775 A1    May 9, 2024

Related U.S. Application Data

(62) Division of application No. 17/119,670, filed on Dec. 11, 2020, now Pat. No. 11,884,927, which is a division of application No. 15/739,101, filed as application No. PCT/US2016/039050 on Jun. 23, 2016, now Pat. No. 10,876,124.

(60) Provisional application No. 62/185,181, filed on Jun. 26, 2015.

(51) Int. Cl.
*C12N 15/74* (2006.01)
*C12N 9/88* (2006.01)
*C12Q 1/68* (2018.01)

(52) U.S. Cl.
CPC ............... *C12N 15/74* (2013.01); *C12N 9/88* (2013.01); *C12Y 402/0302* (2013.01); *C12Y 402/03051* (2013.01); *C07K 2319/02* (2013.01)

(58) Field of Classification Search
CPC . C12N 15/74; C12N 9/88; C12Q 1/68; G01N 33/569
See application file for complete search history.

(56) References Cited

U.S. PATENT DOCUMENTS

| | | | |
|---|---|---|---|
| 9,163,264 B2 * | 10/2015 | Green | C12P 7/6436 |
| 9,315,820 B2 | 4/2016 | Dühring | |
| 9,580,728 B2 | 2/2017 | Kallas et al. | |
| 2002/0094557 A1 | 7/2002 | Chappell | |
| 2003/0175861 A1 | 9/2003 | Steele | |
| 2009/0104656 A1 | 4/2009 | Weiss et al. | |
| 2012/0077251 A1 | 3/2012 | Reppas | |
| 2013/0133102 A1 | 5/2013 | Kerfeld et al. | |
| 2014/0030785 A1 | 1/2014 | Kallas et al. | |
| 2015/0159178 A1 * | 6/2015 | Green | C12P 7/6472 435/257.1 |
| 2019/0203232 A1 | 7/2019 | Melis et al. | |

FOREIGN PATENT DOCUMENTS

| | | |
|---|---|---|
| EP | 0157253 A1 | 3/1985 |
| WO | 1988/06631 A1 | 9/1988 |
| WO | 2012/078279 A2 | 6/2012 |
| WO | 2013/119644 A1 | 8/2013 |
| WO | 2014/037050 A1 | 3/2014 |

OTHER PUBLICATIONS

International Search report from PCT/US2016/039050, dated Dec. 8, 2016, 3 pages.
Bentley, et al., "Heterologous Expression of the Mevalonic Acid Pathway in Cyanobacteria Enhances Endogenous Carbon Partitioning to Isoprene," Molecular Plant, vol. 7, No. 1, pp. 71-86 (2014).
Bentley, et al., "Paradigm of Monoterpene (β-phellandrene) Hydrocarbons Production via Photosynthesis in Cyanobacteria," Bioenerg. Res. vol. 6, pp. 917-929 (2013).
Desplancq, et al., "Automated overexpression and isotopic labelling of biologically active oncoproteins in the cyanobacterium *Anabaena* sp. PCC 7120," Biotechnology and Applied Biochemistry, vol. 51, No. 1, pp. 53-61 (2008).
Elhai, J., "Strong and regulated promoters in the cyanobacterium *Anabaena* PCC 7120," FEMS Microbiology Letters 114 (1993) pp. 179-184.
Formighieri, et al., "Regulation of β-phellandrene synthase gene expression, recombinant protein accumulation, and monoterpene hydrocarbons production in Synechocystis transformants," Planta vol. 240, pp. 309-324 (2014).
Kirst, et al., "Maximizing photosynthetic efficiency and culture productivity in cyanobacteria upon minimizing the phycobilisome light-harvesting antenna size," Biochimica et Biophysica Acta, vol. 1837, pp. 1653-1664 (2014).
Markley, et al., "Synthetic Biology Toolbox for Controlling Gene Expression in the Cyanobacterium *Synechococcus* sp. Strain PCC 7002," ACS Synth. Biol. 2015, 4, pp. 595-603.
Muto, et al., "Accumulation and processing of a recombinant protein designed as a cleavable fusion to the endogenous Rubisco LSU protein in *Chlamydomonas* chloroplast," BMC Biotechnology 2009 9:26 pp. 1-11.
Plank, et al., "Heterologous Assembly and Rescue of Stranded Phycocyanin Subunits by Expression of a Foreign cpcBA Operon in *Synechocystis* sp. Strain 6803," Journal of Bacteriology, Dec. 1995, vol. 177, No. 23, pp. 6804-6809.
Zhou, et al., "Discovery of a super-strong promoter enables efficient production of heterologous proteins in cyanobacteria," Scientific Reports, vol. 4:4500, pp. 1-6 (2014).
Extended European Search Report issued Nov. 27, 2018 in EP Application No. 16 81 5320, 12 pages.
Lattemann, et al., "Autodisplay: Functional Display of Active Beta-Lactamase on the Surface of *Escherichia coli* by the AIDA-I Autotransporter," Journal of Bacteriology, Jul. 2000, vol. 182, No. 13, pp. 3726-3733.

\* cited by examiner

*Primary Examiner* — Maryam Monshipouri
(74) *Attorney, Agent, or Firm* — Kilpatrick, Townsend & Stockton LLP

(57) ABSTRACT

This invention provides compositions and methods for providing high product yield of transgenes expressed in cyanobacteria and microalgae.

20 Claims, 12 Drawing Sheets
Specification includes a Sequence Listing.

FUSION CONSTRUCTS AS PROTEIN OVER-EXPRESSION VECTORS

CROSS-REFERENCE TO RELATED APPLICATIONS

This application is a divisional of U.S. application Ser. No. 17/119,670, filed Dec. 11, 2020, which is a divisional of Ser. No. 15/739,101, filed Dec. 21, 2017, now U.S. Pat. No. 10,876,124, issued Dec. 29, 2020, which is a U.S. National Phase of International Application No. PCT/US2016/039050, filed Jun. 23, 2016, which claims priority benefit of U.S. Provisional Application No. 62/185,181, filed Jun. 26, 2015, each of which applications is incorporated by reference herein for all purposes.

STATEMENT AS TO RIGHTS TO INVENTIONS MADE UNDER FEDERALLY SPONSORED RESEARCH AND DEVELOPMENT

This invention was made during work supported under Grant number DE-AR0000204 awarded by the U.S. Department of Energy. The government has certain rights in this invention.

REFERENCE TO A "SEQUENCE LISTING" SUBMITTED AS AN XML FILE ELECTRONICALLY

This application includes a Sequence Listing written in file 086540_1233557_005430US_SL.xml created on Dec. 15, 2023; 71,346 bytes. The material contained in the XML file is hereby incorporated by reference in its entirety for all purposes.

BACKGROUND OF THE INVENTION

Cyanobacteria such as *Synechocystis* and other microalgae can be used as photosynthetic platforms for the heterologous generation of products of interest (e.g., Ducat et al. 2011; Oliver and Atsumi 2014; Savakis and Hellingwerf 2015), including terpene hydrocarbons. Compounds that can be synthesized in the cyanobacterial cell but spontaneously separate from the biomass and the extracellular aqueous medium are particularly attractive because product segregation and harvesting are simplified. This is a parameter that weighs heavily on the economics of a microbial production system, as a spontaneous product separation from the biomass alleviates negative effects associated with product accumulation inside the cells. The latter include potential inhibitory or toxic effects of the product molecule on cellular metabolism, and considerably higher costs associated with product extraction from the cell interior, harvesting, and downstream processing (Melis 2012; Wijffels et al. 2013).

β-Phellandrene ($C_{10}H_{16}$) is a monoterpene with commercial value as a key ingredient in synthetic chemistry, medical, cosmetic and cleaning products, and potentially as a fuel (Bentley et al. 2013). It is a component of plant essential oils, naturally synthesized in plant trichomes from geranyldiphosphate (GPP) by a nuclear-encoded and plastid localized β-phellandrene synthase (PHLS) enzyme. Heterologous production of β-phellandrene was achieved by genetic engineering of the cyanobacterium *Synechocystis*, showing spontaneous and quantitative separation of the molecule from the biomass and the extracellular aqueous phase. β-Phellandrene efficiently diffused through the plasma membrane and cell wall and, because of its hydrophobicity, accumulated as a floater molecule at the surface of the culture, from where it was harvested by siphoning (Bentley et al. 2013; Formighieri and Melis 2014a).

Heterologous expression of the PHLS gene via genomic DNA chromosome-based transformation is necessary and sufficient for the constitutive photoautotrophic generation of β-phellandrene in *Synechocystis* transformants (Bentley et al. 2013; Formighieri and Melis 2014a). More specifically, the codon optimized PHLS gene from *Lavandula angustifolia* (lavender) (Demissie et al. 2011) was expressed under the control of the strong endogenous cpc promoter via homologous recombination and replacement of the cpc operon (Formighieri and Melis 2014a). The cpc operon (locus 724094-727466 in the *Synechocystis* genome, see, the website genome.microbedb.jp/cyanobase>) encodes for five proteins, i.e., the phycocyanin (Phc) β- and α-subunits (cpcB and cpcA genes), and their linker polypeptides (encoded for by the cpcC2, cpcC1 and cpcD genes), all of which constitute the peripheral rods of the phycobilisome (PBS) light-harvesting antenna complex.

In *Synechocystis*, the PBS light-harvesting antenna is a pigment-protein macrocomplex resting on the outside surface of thylakoid membranes and functionally connected to the photosystem Chl-proteins. It is composed of three core cylinders of allophycocyanin (APC) and of six peripheral rods that radiate away from APC (Kirst et al. 2014). Each peripheral rod is composed of three stacked discs of phycocyanin hexamers containing the Phc β- and α-subunits. Deletion of the cpc operon by a recombinant construct resulted in a truncated PBS antenna phenotype, improving sunlight utilization efficiency and photosynthetic productivity of the cyanobacteria under mass culture and high light intensities (Kirst et al. 2014). Integration and expression of a transgene via homologous recombination and deletion of the cpc operon is therefore a strategy to simultaneously improve the efficiency of bright sunlight utilization and also to reprogram photosynthate metabolism in *Synechocystis* cells.

Phycocyanin (Phc) is one of the most abundant proteins in cyanobacteria, suggesting strong expression elements in the promoter and 5'UTR of the cpcB gene, including aspects of the function of the cpc operon transcription and translation processes. Taking advantage of this property, expression of the PHLS transgene under the cpc endogenous promoter improved the accumulation of the PHLS protein (Bentley et al. 2013) to a point where the transgenic protein was, for the first time, visible in the Coomassie-stained SDS-PAGE of *Synechocystis* protein extracts (Formighieri and Melis 2014a). Correspondingly, the amount of β-phellandrene hydrocarbons produced also increased from about 0.01 to about 0.2 mg of β-phellandrene per g of dry cell weight (Formighieri and Melis 2014a). It was concluded, however, that limitations in rate and yield of β-phellandrene hydrocarbons production are in part due to the limited concentration of the transgenic enzyme in the transformant cells.

High product yield requires high levels of transgenic protein accumulation to facilitate high rates of catalysis for product synthesis. Bacterial proteins have been heterologously over-expressed in cyanobacteria up to 15% of total soluble protein by using the strong cpc operon promoter (Kirst et al. 2014; Zhou et al. 2014). In cyanobacteria and microalgae, however, heterologous expression of plant genes occurs at low levels, resulting in slow rates of product generation, thus undermining commercial exploitation of these photosynthetic microorganisms in the generation of plant-based products. For example, heterologous expression in cyanobacteria of proteins from higher plants yields low levels of recombinant protein, even under the control of strong endogenous promoters (e.g., psbA1, psbA2, psbA3, rbcL, cpc operon) or strong heterologous promoters (e.g., Ptrc) and even after following codon-use optimization (Lindberg et al. 2010; Bentley et al. 2013; Chen and Melis 2013; Formighieri and Melis 2014a; Jindou et al. 2014; Xue et al. 2014; Halfmann et al. 2014).

Detection of plant transgenic proteins in cyanobacteria typically requires Western blot analysis to visualize the low level of the transgenes, as these cannot be seen in SDS-PAGE Coomassie-stained gels. For example, Lindberg et al. (2010) could show expression of a *Pueraria montana* (kutzu) isoprene synthase in *Synechocystis* only through Western blot analysis. Bentley et al. (2013) could similarly show expression of a *Lavandula angustifolia* (lavender) β-phellandrene synthase in *Synechocystis* only through Western blot analysis. Formighieri and Melis (2014a) could show only low levels of *Lavandula angustifolia* (lavender) β-phellandrene synthase in *Synechocystis* under the control of a variety of strong endogenous or exogenous promoters. Jindou et al. (2014) successfully expressed two ethylene biosynthesis genes from *Solanum lycopersicum* in *Synechococcus elongatus*, but could offer evidence of transgenic proteins expression only through Western blot analysis. Xue et al. (2014) expressed only low levels of p-coumarate-3-hydroxylase from *Arabidopsis thaliana* for caffeic acid production in *Synechocystis*. Similarly, Halfmann et al. (2014) expressed only low levels of limonene synthase from Sitka spruce for limonene production in the filamentous cyanobacterium *Anabaena*. Accordingly, there is a need to improve expression levels of heterologous plant proteins, such as terpene synthase. The present invention addresses this need. The present invention discloses fusion constructs in cyanobacteria as transgenic protein over-expression vectors enabling high levels of transgenic plant protein accumulation, e.g. terpene synthases, and resulting in high rates and yields of terpene hydrocarbon synthesis. Specifically, the barrier of expressing plant proteins in cyanobacteria was overcome upon fusion of transgenic plant proteins to highly expressed endogenous proteins (e.g. the CpcB β-subunit of phycocyanin) or to the highly expressed exogenous proteins (e.g. the NPTI selection marker) in cyanobacteria, demonstrating that such fusions are necessary and sufficient to drive over-accumulation of a recalcitrant plant protein.

BRIEF SUMMARY OF SOME ASPECTS OF THE INVENTION

The present invention is based, in part on the discovery of fusion protein constructs that can be used in cyanobacteria as transgenic protein over-expression vectors to provide high levels of transgenic plant protein, e.g., terpene synthases, accumulation and thus provide high rates of production of bioproducts generated by the transgenic plant protein, e.g., high yields of terpene hydrocarbons. The barrier to expressing plant proteins in cyanobacteria at high levels was overcome by the present invention, which provides compositions and methods for the fusion of transgenic plant proteins to highly expressed endogenous cyanobacteria proteins, such as the CpcB β-subunit of phycocyanin, or to an exogenous protein that is highly expressed in cyanobacteria (e.g., the NPTI selection marker).

In one aspect, the invention thus provides an expression construct comprising a nucleic acid sequence encoding a transgene that is codon-optimized for expression in cyanobacteria fused to the 3' end of a leader nucleic acid sequence encoding a cyanobacteria protein that is expressed in cyanobacteria at a level of at least 1% of the total cellular protein or fused to the 3' end of a leader nucleic acid sequence encoding an exogenous protein that is over-expressed in cyanobacteria at a level of at least 1% of the total cellular protein. In some embodiments, the leader nucleic acid sequence encodes a cyanobacteria protein that is expressed at a level of at least 1% of the total cellular protein in cyanobacteria. In some embodiments, the leader nucleic acid sequence encodes a β-subunit of phycocyanin (cpcB), an α-subunit of phycocyanin (cpcA), a phycoerythrin subunit (cpeA or cpeB), an allophycocyanin subunit (apcA or apcB), a large subunit of Rubisco (rbcL), a small subunit of Rubisco (rbcS), a D1/32 kD reaction center protein (psbA) of photosystem-II, a D2/34 kD reaction center protein (psbD) of photosystem-II, a CP47 (psbB) or CP43 (psbC) reaction center protein of photosystem-II, a psaA or psaB reaction center protein of photosystem-I, a psaC or psaD reaction center protein of photosystem-I, an rpl ribosomal RNA protein, or an rps ribosomal RNA protein. In some embodiments, the leader nucleic acid sequence is a variant of a native nucleic acid sequence that encodes a β-subunit of phycocyanin (cpcB), an α-subunit of phycocyanin (cpcA), a phycoerythrin subunit (cpeA or cpeB), an allophycocyanin subunit (apcA or apcB), a large subunit of Rubisco (rbcL), a small subunit of Rubisco (rbcS), a D1/32 kD reaction center protein (psbA) of photosystem-II, a D2/34 kD reaction center protein (psbD) of photosystem-II, a CP47 (psbB) or CP43 (psbC) reaction center protein of photosystem-II, a psaA or psaB reaction center proteins of photosystem-I, a psaC and psaD reaction center proteins of photosystem-I, an rpl ribosomal RNA protein, or an rps ribosomal RNA protein. In some embodiments, the leader nucleic acid sequence encodes an exogenous protein that is over-expressed in cyanobacteria at a level of at least 1% of the total cellular protein. In some embodiments, the exogenous protein that is over-expressed in cyanobacteria is an antibiotic resistance protein. In some embodiments, the leader nucleic acid sequence is an antibiotic resistance gene that encodes a protein that confers resistant to kanamycin, chloramphenicol, streptomycin, or spectinomycin, or a variant of the antibiotic resistance gene.

In some embodiments, the transgene encodes a terpene synthase, e.g., isoprene synthase. In some embodiments, the transgene encodes a monoterpene synthase, e.g., a beta-phellandrene synthase, such as a lavender, tomato, grand fir, pine, or spruce beta-phellandrene synthase. In some embodiments, the transgene encodes a sesquiterpene synthase, such as a farnesene synthase, a zingiberene synthase, a caryophellene synthase, a longifolene synthase, or a dictyophorine synthase.

In a further aspect the invention provides a host cell comprising an expression construct encoding a fusion protein as described herein. In some embodiments the host cell is a cyanobacteria host cell. In some embodiments, the cyanobacteria is a single celled cyanobacteria, e.g., a *Synechococcus* sp., a *Thermosynechococcus elongatus*, a *Synechocystis* sp., or a *Cyanothece* sp.; a micro-colonial cyanobacteria, e.g., a *Gloeocapsa magma, Gloeocapsa phylum, Gloeocapsa alpicola, Gloeocpasa atrata, Chroococcus* spp., or *Aphanothece* sp.; or a filamentous cyanobacteria, e.g., an *Oscillatoria* spp., a *Nostoc* sp., an *Anabaena* sp., or an *Arthrospira* sp.

In further aspects, the invention provides a cyanobacterial cell culture comprising a cyanobacteria host cell containing a fusion expression constructs as described herein, e.g., a cyanobacteria host cell as described in the preceding paragraph; and/or a photobioreactor containing the cyanobacterial cell culture.

In further aspects, the invention provides a method of expressing a transgene at high levels, e.g., to produce a terpenoid, the method comprising culturing a cyanobacterial cell culture of the preceding paragraph under conditions in which the transgene is expressed.

In some embodiments, the invention provides a method of modifying a cyanobacterial cell to express a transgene at high levels, the method comprising introducing an expression cassette as described herein into the cell.

In further aspects, the invention provides an isolated fusion protein comprising a protein to be expressed in cyanobacteria fused to the 3' end of a heterologous leader protein that is expressed in cyanobacteria at a level of at least 1% of the total cellular protein. In some embodiments, the heterologous leader protein is a native cyanobacteria protein. In some embodiments, the heterologous leader protein is a non-native cyanobacteria protein. The invention additionally provides a nucleic acid encoding such a fusion protein.

BRIEF DESCRIPTION OF THE DRAWINGS

FIG. 1 (arrows) also shows the position of primers for this analysis. (A) PCR reactions using primers cpc_us and cpcA_Rv, amplifying the cpc promoter-to-cpcA genomic region. (B) PCR reactions using primers cpc_us and cpcC2_Rv, amplifying the cpc promoter-to-cpcC2 genomic region. (C) PCR reactions using primers cpcC1_Fw and cpc_ds, amplifying the cpcC1-to-3'end downstream region of the cpc operon, where genes encoding for the linker polypeptides are localized. (D) PCR reaction using primers cpc_us and PHLS_Rv, amplifying the cpc promoter-to-PHLS transgene genomic region, and designed to test integration of the PHLS transgene in the transformants.

DETAILED DESCRIPTION OF THE INVENTION

Figure 1:
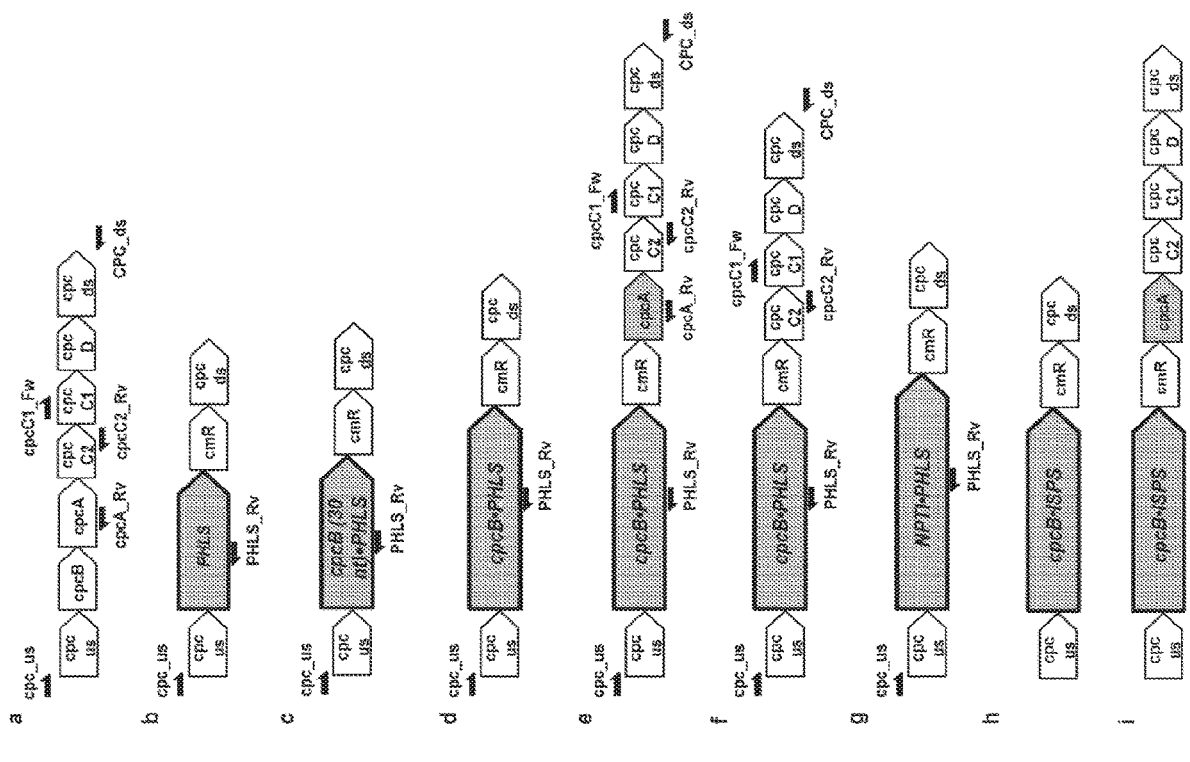
FIG. 1 Schematic overview of DNA constructs designed to transform the genotype of Synechocystis, as used in the present work. (a) The cpc operon, as it occurs in wild type cyanobacteria. (b) Construct Δcpc+PHLS was designed to replace the coding sequence of the endogenous cpc operon in Synechocystis with the PHLS and chloramphenicol resistance (cmR) genes. (c) Construct Δcpc+cpcB(30 nt)·PHLS expresses the PHLS and cmR genes with the former fused to the first 30 nucleotides of the endogenous CpcB-encoding sequence. (d, e, f) Constructs Δcpc+cpcB·PHLS, cpcB·PHLS+cpc, and cpcB·PHLS+cpc(−cpcA) express a fusion CpcB·PHLS and cmR genes in the absence of other cpc operon genes (d), in the presence of the remainder cpc operon genes (e), or in the presence of the remainder cpc operon genes, minus the cpcA gene (f). (g) Construct Δcpc+NPTI·PHLS was designed to replace the coding sequence of the endogenous cpc operon in Synechocystis with a fusion NPTI·PHLS encoding sequence. (h, i) Constructs Δcpc+cpcB·ISPS and cpcB·ISPS+cpc express a fusion CpcB·ISPS and cmR genes in the absence of other cpc operon genes (h) or in the presence of the remainder cpc operon (i).

The term "naturally-occurring" or "native" as used herein as applied to a nucleic acid, a protein, a cell, or an organism, refers to a nucleic acid, protein, cell, or organism that is found in nature. For example, a polypeptide or polynucleotide sequence that is present in an organism that can be isolated from a source in nature and which has not been intentionally modified by a human in the laboratory is naturally occurring.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence endogenous to the host microorganism or host cell. In some embodiments, a "heterologous" nucleic acid may comprise a nucleotide sequence that differs in sequence from the endogenous nucleotide sequence but encodes the same protein (having the same amino acid sequence) as found endogenously; or two or more nucleotide sequences that are not found in the same relationship to each other in nature, e.g., the nucleic acid is recombinant. An example of a heterologous nucleic acid is a nucleotide sequence encoding a fusion protein comprising two proteins that are not joined to one another in nature.

The term "recombinant" polynucleotide or nucleic acid refers to one that is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. A "recombinant" protein is encoded by a recombinant polynucleotide. In the context of a genetically modified host cell, a "recombinant" host cell refers to both the original cell and its progeny.

As used herein, the term "genetically modified" refers to any change in the endogenous genome of a cyanobacteria cell compared to a wild-type cell. Thus, changes that are introduced through recombinant DNA technology and/or classical mutagenesis techniques are both encompassed by this term. The changes may involve protein coding sequences or non-protein coding sequences such as regulatory sequences as promoters or enhancers.

An "expression construct" or "expression cassette" as used herein refers to a recombinant nucleic acid construct, which, when introduced into a cyanobacterial host cell in accordance with the present invention, results in increased expression of a fusion protein encoded by the nucleic acid construct. The expression construct may comprise a promoter sequence operably linked to a nucleic acid sequence encoding the fusion protein or the expression cassette may comprise the nucleic acid sequence encoding the fusion protein where the construct is configured to be inserted into a location in a cyanobacterial genome such that a promoter endogenous to the cyanobacterial host cell is employed to drive expression of the fusion protein.

By "construct" is meant a recombinant nucleic acid, generally recombinant DNA, which has been generated for the purpose of the expression of a specific nucleotide sequence(s), or is to be used in the construction of other recombinant nucleotide sequences.

As used herein, the term "exogenous protein" refers to a protein that is not normally or naturally found in and/or produced by a given cyanobacterium, organism, or cell in nature. As used herein, the term "endogenous protein" refers to a protein that is normally found in and/or produced by a given cyanobacterium, organism, or cell in nature.

An "endogenous" protein or "endogenous" nucleic acid" is also referred to as a "native" protein or nucleic acid that is found in a cell or organism in nature.

The terms "nucleic acid" and "polynucleotide" are used synonymously and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones. Thus, nucleic acids or polynucleotides may also include modified nucleotides, that permit correct read through by a polymerase. "Polynucleotide sequence" or "nucleic acid sequence" may include both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses conservatively modified variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc The term "promoter" or "regulatory element" refers to a region or sequence determinants located upstream or downstream from the start of transcription that are involved in recognition and binding of RNA polymerase and other proteins to initiate transcription. A "cyanobacteria promoter" is a promoter capable of initiating transcription in cyanobacteria cells. Such promoters need not be of cyanobacterial origin, for example, promoters derived from other bacteria or plant viruses, can be used in the present invention.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. *APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" in the context of polynucleotide or polypeptide sequences means that a polynucleotide or polypeptide comprises a sequence that has at least 50% sequence identity to a reference nucleic acid or polypeptide sequence. Alternatively, percent identity can be any integer from 40% to 100%. Exemplary embodiments include at least: 50%, 55%, 60%, 65%, 70%, 75%, 80%, 85%, 90%, 95%, or 99% compared to a reference sequence using the programs described herein; preferably BLAST using standard parameters, as described below.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

The term "isolated", when applied to a nucleic acid or protein, denotes that the nucleic acid or protein is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest.

The term "reactor" as used herein refers to the vessel in which cyanobacteria are grown.

INTRODUCTION

The present invention is based, in part, on the discovery of fusion protein constructs that can be used in cyanobacteria as transgenic protein over-expression vectors to provide high levels of transgenic plant protein, e.g., terpene synthases. Expression of transgenes in cyanobacteria using such vectors results in accumulation of a protein encoded by the transgene to levels that provide high rates of production of products generated by the transgenic plant protein, e.g., high yields of terpene hydrocarbons.

A fusion protein of the present invention comprises a protein that is to be expressed in cyanobacteria, typically a non-native protein that is not expressed in cyanobacteria, e.g., a plant protein fused to a protein that is expressed at high levels in cyanobacteria. In the context of the present invention, a protein that is "expressed at high levels in cyanobacteria" refers to a protein that accumulates to at least 1% of total cellular protein as described herein. Such proteins, when fused at the N-terminus of a protein of interest to be expressed in cyanobacteria, are also referred to herein as "leader proteins", "leader peptides", or "leader sequences". A nucleic acid encoding a leader protein is typically referred to herein as a "leader polynucleotide" or "leader nucleic acid sequence" or "leader nucleotide sequence".

In some embodiments, a protein that is expressed at high levels is a naturally occurring protein that is expressed at high levels in wild-type cyanobacteria, and is used as endogenous "leader polypeptide sequence" in the cyanobacterial strain of origin. Such proteins include, e.g., a phycocyanin β-subunit (cpcB), a phycocyanin α-subunit (cpcA), a phycoerythrin α-subunit (cpeA), a phycoerythrin β-subunit (cpeB), an allophycocyanin α-subunit (apcA), an allophycocyanin β-subunit (apcB), a large subunit of Rubisco (rbcL), a small subunit of Rubisco (rbcS), a photosystem II reaction center protein, a photosystem I reaction center protein, or a rp1 or rps cyanobacterial ribosomal RNA protein. In some embodiments, a protein that is expressed at high levels is a naturally occurring protein that is expressed at high levels in wild-type cyanobacteria, and it is used as heterologous leader sequence in a different cyanobacterial strain.

In some embodiments, a protein that is expressed at high levels is an exogenous protein that the cyanobacteria have been genetically modified to express at high levels. For example, proteins that provide for antibiotic resistance that are expressed to high levels in cyanobacteria, e.g., a bacterial kanamycin resistance protein, NPT, or a bacterial chloramphenicol resistance protein, CmR, may be used as a leader sequence.

The invention additionally provides nucleic acids encoding a fusion protein as described herein, as well as expression constructs comprising the nucleic acids and host cells that have been genetically modified to express such fusion proteins. In further aspects, the invention provides methods of modifying a cyanobacterial cell to overexpress a protein of interest using an expression construct of the invention and methods of producing the protein of interests and products generated by the proteins using such genetically modified cyanobacterial cells.

The invention employs various routine recombinant nucleic acid techniques. Generally, the nomenclature and the laboratory procedures in recombinant DNA technology described below are those commonly employed in the art. Many manuals that provide direction for performing recombinant DNA manipulations are available, e.g., Sambrook, Molecular Cloning, A Laboratory Manual (4th Ed, 2012); and Current Protocols in Molecular Biology (Ausubel et al., eds., 1994-2015).

Proteins Expressed at High Levels in Cyanobacteria

In the present invention, nucleic acid constructs are created in which a polynucleotide sequence encoding a protein of interest is fused to the C-terminal end of a polynucleotide that encodes a leader protein, i.e., a protein that is expressed at high levels in cyanobacteria as described herein. The protein of interest is then also expressed at high levels in conjunction with the leader sequence. In the context of the invention, a protein that is "expressed at high levels" in cyanobacteria refers to a protein that is at least 1%, typically at least 2%, at least 3%, at least 4%, at least 5%, or at least 10%, or greater, of the total protein expressed in the cyanobacteria. Expression levels in cyanobacteria may be evaluated in cells that are logarithmically growing, but may be alternatively determined in cells in a stationary phase of growth. The level of protein expression can be assessed using various techniques. In the present invention, high level expression is typically determined using SDS PAGE analysis. Following electrophoresis, the gel is stained and the level of proteins assessed by scanning the gel and quantifying the amount of protein using an image analyzer.

In some embodiments, a leader sequence in accordance with the invention encodes a naturally occurring cyanobacteria protein that is expressed at high levels in native cyanobacteria. Thus, in some embodiments, the protein is endogenous to cyanobacteria. Examples of such proteins include cpcB, cpcA, cpeA, cpeB, apcA, apcB, rbcL, rbcS, psbA, rp1, or rps. In some embodiments, the leader sequence encodes less than the full-length of the protein, but typically comprises a region that encodes at least 25%, typically at least 50%, or at least 75%, or at least 90%, or at least 95%, or greater, of the length of the protein. As appreciated by one of skill in the art, use of an endogenous cyanobacterial polynucleotide sequence for constructing an expression construct in accordance with the invention provides a sequence that need not be codon-optimized, as the sequence is already expressed at high levels in cyanobacteria. Examples of cyanobacterial polynucleotides that encode cpcB, cpcA, cpeA, cpeB, apcA, apcB, rbcL, rbcS, psbA, rp1, or rps are available at the website www.genome.microbedb.jp/cyanobase under accession numbers, as follows:

cpcA: *Synechocystis* sp. PCC6803 sll1578, *Anabaena* sp. PCC7120 arl0529, *Thermosynechococcus elongatus* BP-1 tlr1958, *Synechococcus elongatus* PCC6301 syc0495_c, syc0500_c cpcB: *Synechocystis* sp. PCC6803 sll1577, *Anabaena* sp. PCC7120 arl0528, *Thermosynechococcus elongatus* BP-1 tlr1957, *Synechococcus elongatus* PCC6301 syc0496_c, syc0501_c cpeA: *Prochlorococcus marinus* SS120 Pro0337, *Synechococcus* sp. WH8102 SYNW2009, SYNW2016 cpeB: *Prochlorococcus marinus* SS120 Pro0338, *Synechococcus* sp. WH8102 SYNW2008, SYNW2017 apcA: *Synechocystis* sp. PCC 6803, slr2067; *Anabaena* sp. PCC 7120, al10450, alr0021; *Synechococcus elongatus* PCC 6301, syc1186_d apcB: *Synechocystis* sp. PCC 6803, slr1986, *Anabaena* sp. PCC 7120, alr0022, *Synechococcus elongatus* PCC 6301, syc1187_d rbcL RubisCO large subunit: *Synechocystis* sp. PCC 6803 slr0009 rbcS RubisCO small subunit: *Synechocystis* sp. PCC 6803 slr0012 rp1: 50S ribosomal protein of *Synechocystis*, e.g. sll1803; sll1810; ssr1398.

rps: 30S ribosomal protein of *Synechocystis*, e.g. sll1804; slr1984.

An illustrative cpcB sequence is indicated in SEQ ID NO:2.

The polynucleotide sequence that encodes the leader protein need not be 100% identical to a native cyanobacteria polynucleotide sequence. A polynucleotide variant having at least 50% identity or at least 60% identity, or greater, to a native cyanobacterial polynucleotide sequence, e.g., a native cpcB, cpcA, cpeA, cpeB, rbcL, rbcS, psbA, rp1, or rps cyanobacteria polynucleotide sequence, may also be used, so long as the codons that vary relative to the native cyanobacterial polynucleotide are codon optimized for expression in cyanobacteria and the codons that vary relative to the wild type sequence do not substantially disrupt the structure of the protein. In some embodiments, a polynucleotide variant that has at least 70% identity, at least 75% identity, at least 80% identity, or at least 85% identity, or greater to a native cyanobacterial polynucleotide sequence, e.g., a native cpcB, cpcA, cpeA, cpeB, rbcL, rbcS, psbA, rp1, or rps cyanobacteria polynucleotide sequence, is used, again maintaining codon optimization for cyanobacteria. In some embodiments, a polynucleotide variant that has least 90% identity, or at least 95% identity, or greater, to a native cyanobacterial polynucleotide sequence, e.g., a native cpcB, cpcA, cpeA, cpeB, rbcL, rbcS, psbA, rp1, or rps cyanobacteria polynucleotide sequence, is used. The percent identity is typically determined with reference the length of the polynucleotide that is employed in the construct, i.e., the percent identity may be over the full length of a polynucleotide that encodes the leader polypeptide sequence, or may be over a smaller length, e.g., in embodiments where the polynucleotide encodes at least 25%, typically at least 50%, or at least 75%, or at least 90%, or at least 95%, or greater, of the length of the protein. The protein encoded by a variant polynucleotide sequence as described need not retain a biological function, however, a codon that varies from the wild-type polynucleotide is typically selected such that the protein structure of the native cyanobacterial sequence is not substantially altered by the changed codon, e.g., a codon that encodes an amino acid that has the same charge, polarity, and/or is similar in size to the native amino acid is selected.

In some embodiments, a polynucleotide variant of a naturally over-expressed (more than 1% of the total cellular protein) cyanobacterial gene is employed, that encodes for a polypeptide sequence that has at least 70%, or 80%, or at least 85% or greater identity to the protein encoded by the wild-type gene. In some embodiments, the polynucleotide encodes a protein that has 90% identity, or at least 95% identity, or greater, to the protein encoded by the wild-type gene. Variant polynucleotides are also codon optimized for expression in cyanobacteria.

In some embodiments, a protein that is expressed at high levels in cyanobacteria is not native to cyanobacteria in which a fusion construct in accordance with the invention is expressed. For example, polynucleotides from bacteria or other organisms that are expressed at high levels in cyanobacteria may be used as leader sequences. In such embodiments, the polynucleotides from other organisms are codon-optimized for expression in cyanobacteria. In some embodiments, codon optimization is performed such that codons used with an average frequency of less than 12% by *Synechocystis* are replaced by more frequently used codons. Rare codons can be defined, e.g., by using a codon usage table derived from the sequenced genome of the host cyanobacterial cell. See, e.g., the codon usage table obtained from Kazusa DNA Research Institute, Japan (website www.kazusa.or.jp/codon/) used in conjunction with software, e.g., "Gene Designer 2.0" software, from DNA 2.0 (website www.dna20.com/) at a cut-off thread of 15%.

In some embodiments, a leader sequence in accordance with the present invention encodes a protein that confers antibiotic resistance. An example of such a polynucleotide is indicated in SEQ ID NO:5, in which the leader sequence encodes neomycin phosphotransferase e.g., NPT1, which confers neomycin and kanamycin resistance. Other polynucleotides that may be employed include a chloramphenicol acetyltransferase polynucleotide, which confers chrloamphenicol resistance; or a polynucleotide encoding a protein that confers streptomycin, ampicillin, or tetracycline resistance, or resistance to another antibiotic. In some embodiments, the leader sequence encodes less than the full-length of the protein, but typically comprises a region that encodes at least 25%, typically at least 50%, or at least 75%, or at least 90%, or at least 95%, or greater, of the length of the protein. In some embodiments, a polynucleotide variant of a naturally occurring antibiotic resistance gene is employed. As noted above, a variant polynucleotide need not encode a protein that retains the native biological function. A variant polynucleotide typically encodes a protein that has at least 80% identity, or at least 85% or greater, identity to the protein encoded by the wild-type antibiotic resistance gene. In some embodiments, the polynucleotide encodes a protein that has 90% identity, or at least 95% identity, or greater, to the wild-type antibiotic resistance protein. Such variant polynucleotides employed as leader sequence are also codon-optimized for expression in cyanobacteria. The percent identity is typically determined with reference to the length of the polynucleotide that is employed in the construct, i.e., the percent identity may be over the full length of a polynucleotide that encodes the leader polypeptide sequence, or may be over a smaller length, e.g., in embodiments where the polynucleotide encodes at least 25%, typically at least 50%, or at least 75%, or at least 90%, or at least 95%, or greater, of the length of the protein. A protein encoded by a variant polynucleotide sequence need not retain a biological function, however, codons that are present in a variant polynucleotide are typically selected such that the protein structure relative to the wild-type protein structure is not substantially altered by the changed codon, e.g., a codon that encodes an amino acid that has the same charge, polarity, and/or is similar in size to the native amino acid is selected.

Other leader proteins can be identified by evaluating the level of expression of a candidate leader protein in cyanobacteria. For example, a leader polypeptide that does not occur in wild type cyanobacteria may be identified by measuring the level of protein expressed from a polynucleotide codon optimized for expression in cyanobacteria that encodes the candidate leader polypeptide. A protein may be selected for use as a leader polypeptide if the protein accumulates to a level of at least 1%, typically at least 2%, at least 3%, at least 4%, at least 5%, or at least 10%, or greater, of the total protein expressed in the cyanobacteria when the polynucleotide encoding the leader polypeptide is introduced into cyanobacteria and the cyanobacteria cultured under conditions in which the transgene is expressed. The level of protein expression is typically determined using SDS PAGE analysis. Following electrophoresis, the gel is scanned and the amount of protein determined by image analysis.

Transgenes

A fusion construct of the invention may be employed to provide high level expression in cyanobacteria for any desired protein product. In some embodiments, the transgene encodes a plant protein. In some embodiments, the transgene encodes a polypeptide pharmaceutical or an enzyme that is used to generate a desired chemical product.

In some embodiments, the transgene that is expressed encodes a terpene synthase. As used herein, the term "terpene synthase" refers to any enzyme that enzymatically modifies IPP, DMAPP, or a polyprenyl diphosphate, such that a terpenoid compound is produced. Terpene synthases have a highly-conserved N-terminal arginine RR(X8)W motif and also a highly conserved aspartate-rich DDxxD motif required for metal cation, usually Mg++ binding. The term "terpene synthase" includes enzymes that catalyze the conversion of a prenyl diphosphate into an isoprenoid. Terpene synthases include, but are not limited to, isoprene synthase, amorpha-4,11-diene synthase (ADS), beta-caryophyllene synthase, germacrene A synthase, 8-epicedrol synthase, valencene synthase, (+)-delta-cadinene synthase, germacrene C synthase, (E)-beta-farnesene synthase, casbene synthase, vetispiradiene synthase, 5-epi-aristolochene synthase, Aristolchene synthase, beta-caryophyllene, alpha-humulene, (E,E)-alpha-farnesene synthase, (−)-beta-pinene synthase, gamma-terpinene synthase, limonene cyclase, Linalool synthase,1,8-cineole synthase, (+)-sabinene synthase, E-alpha-bisabolene synthase, (+)-bornyl diphosphate synthase, levopimaradiene synthase, abietadiene synthase, isopimaradiene synthase, (E)-gamma-bisabolene synthase, taxadiene synthase, copalyl pyrophosphate synthase, kaurene synthase, longifolene synthase, gamma-humulene synthase, Delta-selinene synthase, beta-phellandrene synthase, limonene synthase, myrcene synthase, terpinolene synthase, (−)-camphene synthase, (+)-3-carene synthase, syn-copalyl diphosphate synthase, alpha-terpineol synthase, syn-pimara-7,15-diene synthase, ent-sandaaracopimaradiene synthase, stemer-13-ene synthase, E-beta-ocimene, S-linalool synthase, geraniol synthase, gamma-terpinene synthase, linalool synthase, E-beta-ocimene synthase, epicedrol synthase, alpha-zingiberene synthase, guaiadiene synthase, cascarilladiene synthase, cis-muuroladiene synthase, aphidicolan-16b-ol synthase, elizabethatriene synthase, sandalol synthase, patchoulol synthase, Zinzanol synthase, cedrol synthase, scareol synthase, copalol synthase, and manool synthase.

In some embodiments, the transgene encodes a monoterpene synthase, such as (β-phellandrene synthase. Illustrative β-phellandrene synthase genes include those from lavender (*Lavandular angustifolia*), grand fir (*Abies grandis*), tomato (*Solanum lycopersicum*), pine (*Pinus contorta, Pinus banksiana*), and spruce (*Picea abies, Picea sitchensis*). See, e.g., Demissie et al., *Planta,* 233:685-696 (2011); Bohlmann et al., *Arch. Biochem. Biophys.,* 368:232-243 (1994); Schilmiller et al., *Proc. Nat. Acad. Sci. U.S.A.,* 106:10865-10870 (2009); and Keeling et al., *BMC Plant Biol.* 11:43-57 (2011). Illustrative accession numbers are: lavender (*Lavandula angustifolia* cultivar Lady), Accession: HQ404305; tomato (*Solanum lycopersicum*), Accession: FJ797957; grand fir (*Abies grandis*), Accession: AF139205; spruce (*Picea sitchensis*) (4 genes identified, Accession Nos: Q426162 (PsTPS-Phel-1), HQ426169 (PsTPS-Phel-2), HQ426163 (PsTPS-Phel-3), HQ426159 (PsTPS-Phel-4). See also, U.S. Patent Application Publication No. 20140370562

In some embodiments, the transgene encodes a hemiterpene synthase, such as isoprene synthase. Illustrative isoprene synthase genes include those from poplar (*Populus alba; Populus tremuloides*) (Miller et al. 2001, supra; Sasaki et al., *FEBS Lett* 579: 2514-2518, 2005; Sharkey et al., *Plant Physiol* 137: 700-712, 2005) and kudzu vine (*Pueraria montana*) (Sharkey et al., 2005). Illustrative accession number include AB198190; (*Populus alba*), AJ294819; (*Polulus alba* x *Polulus tremula*); AY341431 (*Populus tremuloides* (quaking aspen)); AM410988 (*Populus nigra* (Lombardy poplar)); and AY316691 *Pueraria montana* var. *lobata*). See also, U.S. Patent Application Publication No. 20120135490.

In some embodiments, the transgene encodes a sesquiterpene synthase, which catalyzes the transformation of FPP to a sesquiterpene compound. Illustrative sesquiterpene synthases include farnesene synthase, zingiberene synthase, caryophellene synthase, longifolene synthase, and dictyophorine synthase. Illustrative sesquiterpene accession numbers include zingiberene synthase (e.g., AY693646.1); farnesene synthase (e.g., AAT70237.1, AAS68019.1, AY182241); caryophyllene synthase (e.g., AGR40502); and longifolene synthase (e.g. AAS47695, ABV44454).

The transgene portion of a fusion construct in accordance with the invention is codon optimized for expression in cyanobacteria. For example, in some embodiments, codon optimization is performed such that codons used with an average frequency of less than 12% by *Synechocystis* are replaced by more frequently used codons. Rare codons can be defined, e.g., by using a codon usage table derived from the sequenced genome of the host cyanobacterial cell. See, e.g., the codon usage table obtained from Kazusa DNA Research Institute, Japan (website www.kazusa.or.jp/codon/) used in conjunction with software, e.g., "Gene Designer 2.0" software, from DNA 2.0 (website www.dna20.com/) at a cut-off thread of 15%.

Preparation of Recombinant Expression Constructs

Recombinant DNA vectors suitable for transformation of cyanobacteria cells are employed in the methods of the invention. Preparation of suitable vectors and transformation methods can be prepared using any number of techniques, including those described, e.g., in Sambrook, Molecular Cloning, A Laboratory Manual (4th Ed, 2012); and Current Protocols in Molecular Biology (Ausubel et al., eds., 1994-2015). For example, a DNA sequence encoding a fusion protein of the present invention will be combined with transcriptional and other regulatory sequences to direct expression in cyanobacteria.

In some embodiments, the vector includes sequences for homologous recombination to insert the fusion construct at a desired site in a cyanobacterial genome, e.g., such that expression of the polynucleotide encoding the fusion construct will be driven by a promoter that is endogenous to the organism. A vector to perform homologous recombination will include sequences required for homologous recombination, such as flanking sequences that share homology with the target site for promoting homologous recombination.

Regulatory sequences incorporated into vectors that comprise sequences that are to be expressed in the modified cyanobacterial cell include promoters, which may be either constitutive or inducible. In some embodiments, a promoter for a nucleic acid construct is a constitutive promoter. Examples of constitutive strong promoters for use in cyanobacteria include, for example, the psbD1 gene or the basal promoter of the psbD2 gene, or the rbcLS promoter, which is constitutive under standard growth conditions. Various other promoters that are active in cyanobacteria are also known. These include the strong cpc operon promoter, the cpe operon and apc operon promoters, which control expression of phycobilisome constituents. The light inducible promoters of the psbA1, psbA2, and psbA3 genes in cyanobacteria may also be used, as noted below. Other promoters that are operative in plants, e.g., promoters derived from plant viruses, such as the CaMV35S promoters, or bacterial viruses, such as the T7, or bacterial promoters, such as the PTrc, can also be employed in cyanobacteria. For a description of strong and regulated promoters, e.g., active in the cyanobacterium *Anabaena* sp. strain PCC 7120 and *Synechocystis* 6803, see e.g., Elhai, *FEMS Microbiol Lett* 114: 179-184, (1993) and Formighieri, *Planta* 240:309-324 (2014).

In some embodiments, a promoter can be used to direct expression of the inserted nucleic acids under the influence of changing environmental conditions. Examples of environmental conditions that may affect transcription by inducible promoters include anaerobic conditions, elevated temperature, or the presence of light. Promoters that are inducible upon exposure to chemicals reagents are also used to express the inserted nucleic acids. Other useful inducible regulatory elements include copper-inducible regulatory elements (Mett et al., *Proc. Natl. Acad. Sci. USA* 90:4567-4571 (1993); Furst et al., *Cell* 55:705-717 (1988)); copper-repressed petJ promoter in *Synechocystis* (Kuchmina et al. 2012, *J Biotechn* 162:75-80); riboswitches, e.g. theophylline-dependent (Nakahira et al. 2013, *Plant Cell Physiol* 54:1724-1735; tetracycline and chlor-tetracycline-inducible regulatory elements (Gatz et al., *Plant J.* 2:397-404 (1992); Roder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible promoters, such as those of the hsp70/dnaK genes (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992)). An inducible regulatory element also can be, for example, a nitrate-inducible promoter, e.g., derived from the spinach nitrite reductase gene (Back et al., *Plant Mol. Biol.* 17:9 (1991)), or a light-inducible promoter, such as that associated with the small subunit of RuBP carboxylase or the LHCP gene families (Feinbaum et al., *Mol. Gen. Genet.* 226:449 (1991); Lam and Chua, Science 248:471 (1990)).

In some embodiments, the promoter may be from a gene associated with photosynthesis in the species to be transformed or another species. For example such a promoter from one species may be used to direct expression of a protein in transformed cyanobacteria cells. Suitable promoters may be isolated from or synthesized based on known sequences from other photosynthetic organisms. Preferred promoters are those for genes from other photosynthetic species, or other photosynthetic organism where the promoter is active in cyanobacteria.

A vector will also typically comprise a marker gene that confers a selectable phenotype on cyanobacteria transformed with the vector. Such marker genes, include, but are not limited to those that confer antibiotic resistance, such as resistance to chloramphenicol, kanamycin, spectinomycin, G418, bleomycin, hygromycin, and the like.

Cell transformation methods and selectable markers for cyanobacteria are well known in the art (Wirth, *Mol. Gen. Genet.*, 216(1):175-7 (1989); Koksharova, *Appl. Microbiol. Biotechnol.*, 58(2): 123-37 (2002); Thelwell et al., *Proc. Natl. Acad. Sci. U.S.A.*, 95:10728-10733 (1998)).

Any suitable cyanobacteria may be employed to express a fusion protein in accordance with the invention. These include unicellular cyanobacteria, micro-colonial cyanobacteria that form small colonies, and filamentous cyanobacteria. Examples of unicellular cyanobacteria for use in the invention include, but are not limited to, *Synechococcus* and *Thermosynechococcus* sp., e.g., *Synechococcus* sp. PCC 7002, *Synechococcus* sp. PCC 6301, and *Thermosynechococcus elongatus*; as well as *Synechocystis* sp., such as *Synechocystis* sp. PCC 6803; and *Cyanothece* sp., such as PCC 8801. Examples of micro-colonial cyanobacteria for use in the invention, include, but are not limited to, *Gloeocapsa magma, Gloeocapsa phylum, Gloeocapsa alpicola, Gloeocpasa atrata, Chroococcus* spp., and *Aphanothece* sp. Examples of filamentous cyanobacteria that can be used include, but are not limited to, *Oscillatoria* spp., *Nostoc* sp., e.g., *Nostoc* sp. PCC 7120, and *Nostoc sphaeroides; Anabaena* sp., e.g., *Anabaena variabilis* and *Arthrospira* sp. ("*Spirulina*"), such as *Arthrospira platensis* and *Arthrospira maxima*, and *Mastigocladus laminosus*. Cyanobacteria that are genetically modified in accordance with the invention may also contain other genetic modifications, e.g., modifications to the terpenoid pathway, to enhance production of a desired compound.

Cyanobacteria can be cultured to high density, e.g., in a photobioreactor (see, e.g., Lee et al., *Biotech. Bioengineering* 44:1161-1167, 1994; Chaumont, *J Appl. Phycology* 5:593-604, 1990) to produce the protein encoded by the transgene. In some embodiments, the protein product of the transgene is purified. In many embodiments, the cyanobacteria culture is used to produce a desired, non-protein product, e.g., isoprene, a hemiterpene; β-phellandrene, a monoterpene; farnesene, a sesquiterpene; or other products. The product produced from the cyanobacteria may then be isolated or collected from the cyanobacterial cell culture.

Examples

The following examples illustrate the over-expression of β-phellandrene synthase and isoprene synthase in cyanobacteria.

Materials and Methods

*Synechocystis* Strains, Recombinant Constructs, and Culturing Conditions

*Synechocystis* sp. PCC 6803 (*Synechocystis*) was used as the recipient strain and referred to as the wild type (wt) in this study (Williams 1988). The β-phellandrene synthase (PHLS)-encoding gene from *Lavandula angustifolia* (lavender) (Demissie et al. 2011) was codon optimized (Bentley et al. 2013) and cloned between 500 pb of the upstream and downstream sequences of the native cpc operon (FIG. 1a), as recently described (Formighieri and Melis 2014a). Resulting *Synechocystis* transformants, where the cpc operon is replaced by the recombinant construct via homologous recombination, are referred to as Δcpc+PHLS (FIG. 1b). The PHLS gene was then fused either to the first 30 nucleotides of cpcB (FIG. 1c) or to the C-terminus of the complete CpcB-encoding gene (FIG. 1d). The upstream 500 bp of the cpc operon and the cpcB sequence were amplified by PCR from the *Synechocystis* genome, using cpc_us-XhoI as forward primer and either cpcB(30 nt)-NdeI or cpcB-NdeI as reverse primer (Table 1). The resulting PCR product was cloned upstream of PHLS via XhoI and NdeI digestion, removing the native stop codon of cpcB. Homologous recombination was allowed to occur between the 500 pb of the upstream and downstream sequences of the cpc operon, leading to replacement of the cpc operon by the recombinant CpcB·PHLS construct. Resulting *Synechocystis* transformants in this case are referred to as Δcpc+cpcB(30 nt)·PHLS (FIG. 1c) and Δcpc+cpcB·PHLS (FIG. 1d). Homologous recombination was alternatively performed between the upstream sequence of the cpc operon and the CpcA-encoding sequence. The latter was amplified by PCR from the *Synechocystis* genome, using cpcA-BamHI and cpcA-SacI as forward and reverse primers, respectively (Table 1). The CpcA-encoding DNA was then cloned downstream of the recombinant CpcB·PHLS construct via BamHI and SacI digestion, thus replacing the 500 bp of the downstream sequence of the cpc operon previously employed. Transformation of *Synechocystis* and homologous recombination allowed substitution of the native cpcB sequence by the cpcB·PHLS fusion construct while maintaining the other cpc genes in the downstream portion of the operon (FIG. 1e, cpcB·PHLS+cpc transformant). In addition, homologous recombination was designed to occur between the upstream sequence of the cpc operon and the CpcC2-encoding sequence. The latter was amplified by PCR from the *Synechocystis* genome, using cpcC2-BamHI and cpcC2-SacI as forward and reverse primers, respectively (Table 1), and cloned downstream of the recombinant cpcB·PHLS construct via BamHI and SacI digestion. Transformation of *Synechocystis* and homologous recombination allowed integration of cpcB·PHLS upstream of the genes encoding for the linker polypeptides, while deleting the endogenous cpcB and cpcA sequences (FIG. 1f, cpcB·PHLS+cpc(−cpcA) transformant).

PHLS was alternatively fused to the codon-optimized NPTI gene conferring kanamycin resistance. The latter was amplified by PCR using the Δcpc+NPTI plasmid as template (Kirst et al. 2014), and cpc_us-XhoI and NPTI-Rv as forward and reverse primers, respectively (Table 1). The PCR product was then cloned upstream of the PHLS sequence via XhoI and NdeI digestion and used to replace the cpc operon via homologous recombination. The resulting *Synechocystis* transformants are referred to as Δcpc+NPTI·PHLS (FIG. 1g).

The cpcB-transgene fusion strategy was in parallel tested with the *Pueraria montana* (kudzu) isoprene synthase (ISPS) (Lindberg et al. 2010). The ISPS-encoding sequence was amplified by PCR using ISPS-NdeI and ISPS-BglII as forward and reverse primers, respectively (Table 1), and was used to replace, via NdeI and BglII digestion, the PHLS sequence and to express the CpcB·ISPS fusion under the cpc operon promoter. The following transformants were thus obtained upon transformation of *Synechocystis*: Δcpc+CpcB·ISPS (FIG. 1h) and CpcB·ISPS+cpc (FIG. 1i).

*Synechocystis* transformations were made according to established protocols (Eaton-Rye 2011). Wild type and transformants were maintained on 1% agar BG11 media supplemented with 10 mM TES-NaOH (pH 8.2) and 0.3% sodium thiosulphate. Liquid cultures in BG11 were buffered with 25 mM phosphate (pH 7.5) and incubated under continuous low-stream bubbling with air at 28° C. Transgenic DNA copy homoplasmy was achieved with cells incubated on agar in the presence of 30 μg/mL chloramphenicol, 5 mM glucose, under illumination of 170 μmol photons m$^{-2}$ s$^{-1}$.

PCR Analysis of *Synechocystis* Transformants for Insert Site Mapping

Genomic DNA templates were prepared with Chelex®100 Resin (BioRad) as described (Formighieri and Melis 2014a). The following genomic DNA PCR primers were used to map the insert site of the *Synechocystis* transformants, to look for transgene insertion into the correct genomic locus, and also to test for DNA copy homoplasmy: cpc_us, cpcA_Rv, cpcC2_Rv, cpcC1_Fw, cpc_ds, PHLS_Rv. The location of these primers on the genomic DNA is shown in FIG. 1. The oligonucleotide sequences are given in Table 1.

RNA Analysis

Total RNA was prepared from *Synechocystis* cells using the TRIzol®Reagent (Invitrogen), according to the manufacturer's instructions. After DNA digestion with DNAseI (Fermentas), the RNA was reverse-transcribed from random hexamers (Invitrogen) by the SuperScript® III Reverse Transcriptase (Invitrogen). For the RT-qPCR, 10 ng of cDNA were used as template. Primers were designed within the PHLS encoding region to amplify a 113 bp DNA fragment at the 3' end (PHLS1_Fw and PHLS1_Rv primers) or a 137 bp DNA fragment toward the 5' end (PHLS2_Fw and PHLS2_Rv primers). DNA amplification was monitored by SYBR Green fluorescence (SsoAdvanced™ Universal SYBR® Green Supermix, Bio-Rad). Analysis of relative gene expression data was performed using the $\Delta\Delta C_T$ method (Livak and Schmittgen 2001). The relative abundance of rnpB was used as internal standard (rnpB_Fw and rnpB_Rv primers). All oligonucleotide primer sequences are reported in Table 1.

Protein Analysis

Cells were harvested by centrifugation and resuspended in a buffer containing 50 mM Tris-HCl pH 8, 50 mM NaCl, 10 mM CaCl$_2$, 10 mM MgCl$_2$). The cell suspension was treated first with lysozyme (Thermo Scientific) then with bovine pancreas DNAseI (Sigma) for 30 min each at room temperature. Cell disruption was achieved by passing the suspension through a French press cell at 20,000 psi in the presence of protease inhibitors (1 mM PMSF, 2 mM aminocaproic acid, and 1 mM benzamidine). The sample was then treated with 1% v/v Triton X-100 for 20 minutes and centrifuged at 21,000 g for 20 min to separate the cleared lysate from the pellet. The supernatant was solubilized upon incubation at room temperature with 62 mM Tris-HCl pH 6.8, 1% SDS, 5% β-mercaptoethanol, 10% glycerol. The pellet was solubilized upon incubation with 62 mM Tris-HCl pH 6.8, 3.5% SDS, 1 M urea, 5% β-mercaptoethanol, and 10% glycerol. Unsolubilized material was removed upon centrifugation at 21,000 g for 5 min and the supernatant was loaded on a SDS-PAGE (Bio-Rad, USA). The SDS-PAGE resolved proteins were stained with Coomassie Brilliant Blue G-250 and densitometric analysis of the protein bands was performed in each lane upon application of the GelPro Analyzer software. For Western blot analysis, resolved proteins were transferred from the polyacrylamide gel to a nitrocellulose membrane and probed with either PHLS (Bentley et al. 2013) or CpcA polyclonal antibodies (Abbiotec, Cat. No. 250488).

Polyribosome Analysis

Exponential growth stage cultures were incubated for 15 min with 5 µg/mL kanamycin. Cultures were then cooled to 4° C. and centrifuged at 6,000 g for 10 min. The cell pellet was resuspended in chilled buffer (50 mM Tris-HCl pH 8.2, 50 mM KCl, 25 mM $MgCl_2$, 10 mM EGTA, 5 mM DTT, and 5 µg/mL kanamycin), frozen then thawed in ice water and disrupted by passing through a French Press at 20,000 psi. Nonidet P40 was added to the lysates at a final concentration of 0.5% v/v. The cleared lysate, after centrifugation at 20,000 g for 10 min, was loaded on a 10-40% w/v continuous sucrose gradient and centrifuged at 122,000 g for 5 h in a Beckman SW27 rotor at 4° C. Gradients were fractionated in 10 equal fractions. After removal of the first and the last fractions, total RNA was extracted from the remaining fractions and analyzed by RT-PCR without normalization of the starting RNA quantities: 8 µL for each RNA sample were reverse transcribed in 20 µL reactions and 3 µL were used as templates for the PCR reaction, which was stopped before saturation. cpcB and PHLS were amplified with either cpcB_Fw and cpc_Rv primers or PHLS_Fw and PHLS_Rv primers, respectively (Table 1).

Analysis of Photosynthetic Pigments and Measurement of Photoautotrophic Growth.

Crude homogenates, following cell disruption by French Press, were analyzed by absorbance spectroscopy, revealing the absorbance contributions of chlorophyll a, carotenoids and phycobilins. The supernatant fractions, after removal of the pellet, contained the dissociated phycobilisome and showed the absorbance contributions of Phc and APC. Chlorophyll a and carotenoid analysis was based on extraction in 90% methanol (Meeks and Castenholz 1971). Photoautotrophic growth of wild type and transformants was measured from the optical density of the cultures at 730 nm.

β-Phellandrene Production Assay

β-Phellandrene production and separation from *Synechocystis* cultures were performed as described (Bentley et al. 2013; Formighieri and Melis 2014a). Briefly, liquid cultures of *Synechocystis*, with an optical density (OD) at 730 nm of 0.5, were supplemented with 100% $CO_2$ gas as to fill the ~500 mL gaseous headspace of a 1 L gaseous/aqueous two-phase reactor, then sealed for 48 h and incubated under slow continuous mechanical mixing under 50 µmol photons $m^{-2}$ $s^{-1}$ of incident light intensity. β-Phellandrene was collected as a floater molecule from the surface of the liquid culture. This was achieved upon dilution of the floater β-phellandrene fraction with hexane, while gently stirring for 2 h. The amount of β-phellandrene present was measured in the hexane extract by absorbance spectroscopy and sensitive gas chromatography (GC), according to Formighieri and Melis (2014a; 2014b).

The in vitro assay for β-phellandrene synthase activity and β-phellandrene hydrocarbons synthesis was performed according to Demissie et al. (2011), with measurements performed either with total cell extracts, following cell disruption by French Press, or pellet fractions, after centrifugation at 21,000 g for 5 min. Samples were suspended in 50 mM Tris-HCl pH 6.8, 5% glycerol, 1 mM $MnCl_2$, 1 mM $MgCl_2$, 1 mg/mL BSA, 1 mM DTT, 50 µM geranyl-pyrophosphate (GPP, by Echelon Biosciences), and incubated for 1 h at 30° C. with half volume of hexane as over-layer. The latter was eventually collected and measured by absorbance spectroscopy and GC-analysis.

TABLE 1

Sequences of primers

| Oligo name | Oligo DNA sequence (SEQ ID NOS: 7-40, respectively) |
|---|---|
| cpc_us-XhoI | 5'-CCGCTCGAGAAGAGTCCCTGAATATCAAAA TGGTG-3' |
| cpcB(30 nt)-NdeI | 5'-GGAATTCCATATGGGAAACAACCCGAGTGA ATACGTCG-3' |
| cpcB-NdeI | 5'-GGAATTCCATATGGGCTACGGCAGCAGCGG CGCGG-3' |
| cpcA-BamHI | 5'-CGCGGATCCTCTGGTTATTTTAAAAACCAA CTTTAC-3' |
| cpcA-SacI | 5'-CGCGAGCTCCTAGCTCAGAGCATTGATGGC G-3' |
| cpcC2-BamHI | 5'-CGCGGATCCTCAGTTTTTAATTCTAGCTGG CCTG-3' |
| cpcC2-SacI | 5'-CGCGAGCTCCCTGATTCTAGGCAAGGGAAA TCATTG-3' |
| NPTI-Rv | 5'-GGAATTCCATATGAAAGAACTCATCTAGCA TCAGATG-3' |
| ISPS-NdeI | 5'-GGAATTCCATATGCCCTGGCGTGTAATCTG TGCAAC-3' |
| ISPS-BglII | 5'-GGAAGATCTTTACACGTACATTAATTGATT AATTG-3' |
| cpc_us | 5'-CCATTAGCAAGGCAAATCAAAGAC-3' |
| cpcA_Rv | 5'-GGTGGAAACGGCTTCAGTTAAAG-3' |
| cpcC2_Rv | 5'-CCTGATTCTAGGCAAGGGAAATCATTG-3' |
| cpcC1_Fw | 5'-GTTCCCTTTGGTCAAGCAAGTAAG-3' |
| cpc_ds | 5'-GGTTGATTCGTTTACATCAGTTCAATAA AG-3' |
| PHLS_Rv | 5'-CAATCCGGTCCCGAACAAAC-3' |
| cpcB-PHLS_Fw (RT-PCR) | 5'-CACCGGTAATGCTTCCGCTA-3' |
| cpcB-PHLS_Rv (RT-PCR) | 5'-GCATGTGACGTTCGCCCTTA-3' |
| cpcA-cpcC2_Fw (RT-PCR) | 5'-CCGCATCGTTACCTACTGCT-3' |
| cpcA-cpcC2_Rv (RT-PCR) | 5'-GATCACTGGTAGCGTAGCCC-3' |
| cpcC1-cpcD_Fw (RT-PCR) | 5'-GCTAACAGTGACCGTTCCCA-3' |
| cpcC1-cpcD_Rv (RT-PCR) | 5'-GCGGAGTCCACTGACTTCAT-3' |
| RbcL_Fw (RT-PCR) | 5'-GTATCACCATGGGCTTCGTT-3' |
| RbcL_Rv (RT-PCR) | 5'-CACAAGCTTCCAAAGCAACA-3' |
| PHLS1_Fw (RT-qPCR) | 5'-GACGACGACGATGACGATGA-3' |
| PHLS1_Rv (RT-qPCR) | 5'-ATCCCAAACCCATCGGAACC-3' |

TABLE 1-continued

Sequences of primers

| Oligo name | Oligo DNA sequence (SEQ ID NOS: 7-40, respectively) |
|---|---|
| PHLS2_Fw (RT-qPCR) | 5'-TCTGGAACTCGCCATTCTCG-3' |
| PHLS2_Rv (RT-qPCR) | 5'-AACCTTCCACAATCCGGTCC-3' |
| rnpB_Fw (RT-qPCR) | 5'-GTGAGGACAGTGCCACAGAA-3' |
| rnpB_Rv (RT-qPCR) | 5'-TGCACCCTTACCCTTTTCAG-3' |
| cpcB_Fw (RT-PCR) | 5'-CACCGGTAATGCTTCCGCTA-3' |
| cpcB_Rv (RT-PCR) | 5'-GGCTACGGCAGCAGCGGCGCGG-3' |
| PHLS_Fw (RT-PCR) | 5'-TTGGTGACCTGTTTGGATGA-3' |
| PHLS_Rv (RT-PCR) | 5'-CCAGGCGTTGTTGAGGTATT-3' |

Results

Example: Heterologous Expression of β-Phellandrene Synthase and Isoprene Synthase in *Synechocystis* as a Fusion Protein with the Endogenous Phycocyanin β-Subunit In the *Synechocystis* genome, the cpc operon includes the cpcB and cpcA genes, encoding for the phycocyanin β- and α-subunits, respectively. These, together with the products of the cpcC2, cpcC1 and cpcD genes, encoding for associated linker polypeptides (FIG. 1a), assemble into the peripheral rods of the light-harvesting phycobilisomes. The cpcB and cpcA genes are highly expressed in cyanobacteria, to provide for the abundant phycocyanin β- and α-subunits in the phycobilisome of these microorganisms (Kirst et al. 2014). In this example, the use of the cpc operon promoter to achieve high levels of β-phellandrene synthase (PHLS) transgene expression was evaluated to determine whether, under the control of the cpc promoter, PHLS protein levels would be comparable to those of phycocyanin β- and α-subunits in transformant cyanobacteria. To this end, the β-phellandrene synthase (PHLS) transgene was inserted in the cpc locus of *Synechocystis*, alone or in combination with other cpc operon genes, and expressed under the control of the cpc operon promoter (FIG. 1).

In one such combination, the inserted cassette replaced the entire coding sequence of the cpc operon (Δcpc+PHLS strain) and expressed the β-phellandrene synthase (PHLS) gene directly under the control of the endogenous cpc operon promoter (FIG. 1b). Recent work (Formighieri and Melis 2014a) showed that Δcpc+PHLS transformants accumulated relatively low levels of β-phellandrene synthase, and yielded low levels of β-phellandrene hydrocarbons. Opposite to expectation, levels of PHLS accumulation were nowhere near those of the phycocyanin β- or α-subunits. It became clear that a strong promoter was necessary (Camsund and Lindblad 2014) but not sufficient to yield high levels of transgenic protein. To investigate why the cpc promoter affords high amounts of phycocyanin β- and α-subunits, but not of the β-phellandrene synthase, additional PHLS gene constructs were made in this work for heterologous transformation in the cpc site. In one such configuration, the PHLS gene was fused to the leading 30-nucleotide sequence of the endogenous cpcB, denoted as the Δcpc+cpcB(30 nt)·PHLS transformant (FIG. 1c). Alternatively, the PHLS gene was fused to the C-terminus of the entire CpcB-encoding gene (FIG. 1d, e, f). For the latter, three alternatives of homologous recombination were employed for transgene integration in the cpc operon locus: (i) the cpc operon was deleted and replaced by the cpcB·PHLS fusion sequence, denoted as Δcpc+cpcB·PHLS (FIG. 1d); (ii) the cpcB·PHLS fusion construct replaced the native cpcB sequence only, inserted upstream of the cpcA, cpcC2, cpcC1 and cpcD genes, denoted as cpcB·PHLS+cpc (FIG. 1e); (iii) the cpcB·PHLS fusion construct replaced the native cpcB and cpcA sequences, and was integrated upstream of the cpcC2, cpcC1 and cpcD genes, denoted as cpcB·PHLS+cpc(−cpcA) (FIG. 1f). The gene conferring resistance to chloramphenicol (cmR) was cloned in operon configuration immediately downstream of the PHLS gene. Positive transformants from the various constructs were selected on chloramphenicol-supplemented media.

In addition, PHLS was fused downstream of the *Synechocystis* codon-optimized NPTI sequence conferring resistance to kanamycin. This kanamycin resistance cassette was highly expressed under the control of the cpc operon promoter in *Synechocystis* transformants (Kirst et al. 2014). NPTI was used in this respect as an upstream moiety of a NPTI·PHLS heterologous fusion tag, with the recombinant fusion-protein expressed under the cpc promoter upon replacement of the entire cpc operon, denoted as Δcpc+NPTI·PHLS (FIG. 1g).

To further investigate transgene expression levels as fusion proteins, a *Synechocystis* codon-optimized ISPS isoprene synthase gene (Lindberg et al. 2010) was fused downstream of the cpcB and, along with the chloramphenicol resistance cassette, replaced the entire cpc operon (FIG. 1h). Alternatively, the cpcB·ISPS+cmR construct was directed to replace the cpcB gene only (FIG. 1i), leaving the rest of the cpc operon in place.

Figure 2:
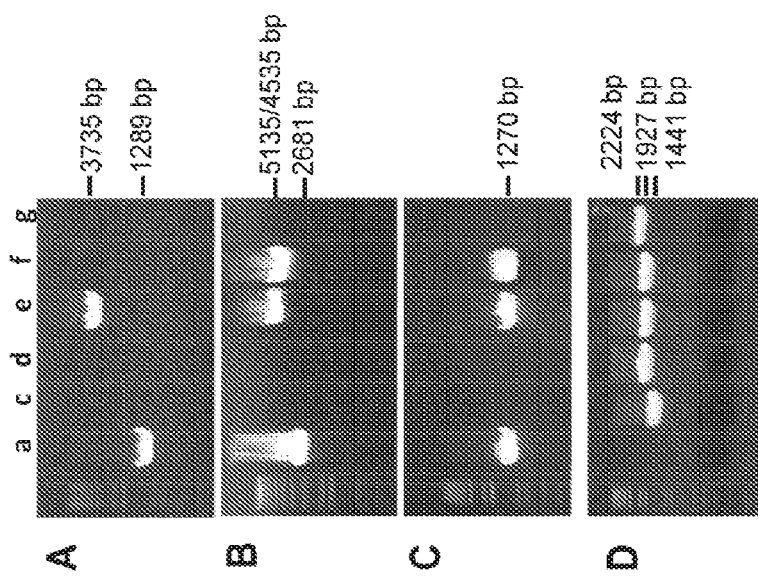
FIG. 2 Genomic DNA PCR analysis with selected forward (us) and reverse (ds) primers positioned on the genomic DNA of Synechocystis wild type and PHLS transformants. Strains a through g were generated by constructs a through g, as shown in FIG. 1.

Genomic DNA PCR analysis was performed to test for insert integration and DNA copy homoplasmy in transformants with each of the above-mentioned constructs. Results from this analysis are shown in FIG. 2. For the results of FIG. 2, lanes a through g, location of the PCR primers is shown in FIG. 1, a through g, respectively. By using primers cpc_us and cpcA_Rv, annealing upstream of the cpc operon promoter and within the cpcA gene, respectively, the PCR reaction generated a 1289 bp product in the wild type (FIG. 2A, lane a) and a 3735 bp product in the cpcB·PHLS+cpc transformant (FIG. 2A, lane e). The larger product size in the latter is due to the CpcB·PHLS fusion and cmR insert. The other transformants (FIG. 2A, lanes c, d, f, g) did not yield a PCR product with these primers, consistent with the absence of the cpcA gene. The specific absence of wild type 1289 bp product in FIG. 2A, lanes c-g, is evidence of having attained transgenic DNA copy homoplasmy in the transformants.

Genomic DNA PCR analysis using primers cpc_us and cpcC2_Rv, annealing upstream of the cpc operon and within the cpcC2 gene, respectively, showed a single 2681 bp product in the wild type (FIG. 2B, lane a). In the cpcB·PHLS+cpc (FIG. 1e) and cpcB·PHLS+cpc(−cpcA) (FIG. 1f) transformants, insertion of the CpcB·PHLS fusion encoding sequence increased the size of the PCR product to 5135 bp and 4535 bp, respectively (FIG. 2B, lanes e and f). The larger size of the PCR products is due to the insertion of the CpcB·PHLS and cmR cassette. In the other transformants in which the cpcC2 gene was deleted upon insertion of the fusion construct (FIG. 2B, lanes c, d, g), no PCR products could be detected with the aforementioned primers. The specific absence of wild type 2681 bp product in FIG.

2B, lanes c-g, is evidence of transgenic DNA copy homoplasmy in the transformants.

PCR reactions using primers cpcC1_Fw and cpc_ds, annealing within the cpcC1 gene and downstream of the cpc operon, respectively, gave a single 1270 bp PCR product in the wild type (FIG. 2C, lane a), in cpcB·PHLS+cpc (FIG. 2C, lane e), and in cpcB·PHLS+cpc(−cpcA) (FIG. 2C, lane f). This result is evidence that genes encoding for the PBS linker polypeptides are present in the genome of these transformants. In contrast, no PCR product could be obtained with the aforementioned primers in the remaining strains (FIG. 2C, lanes c, d, g) because of deletion of the cpc operon upon homologous recombination for the insertion of the PHLS-containing cassette. Absence of a PCR product in the latter is evidence of transgenic DNA copy homoplasmy in the transformants.

Finally, genomic DNA PCR analysis using primers cpc_us and PHLS_Rv, annealing upstream of the cpc operon and within the PHLS sequence, respectively, assessed integration of the PHLS construct in the cpc locus. Products of different sizes, depending on the transgenic construct, were obtained in the transformants including a 1,441 bp for Δcpc+cpcB(30 nt)·PHLS (FIG. 2D, lane c), 1,927 bp for Δcpc+cpcB·PHLS (FIG. 2D, lane d), cpcB·PHLS+cpc (FIG. 2D, lane e), and cpcB·PHLS+cpc(−cpcA) (FIG. 2D, lane f), and 2224 bp for Δcpc+NPTI·PHLS (FIG. 2D, lane g). With the above-mentioned primers, wild type strains generated no PCR product (FIG. 2D, lane a).

A similar thorough genomic DNA PCR analysis was also conducted with the cpcB·ISPS transformants (FIGS. 1h and i), showing a correct integration of the recombinant cassette in the *Synechocystis* genomic DNA, and attainment of transgenic DNA copy homoplasmy in these transformants (results not shown).

Analysis of PHLS Transcription in *Synechocystis* Transformants

Figure 3:
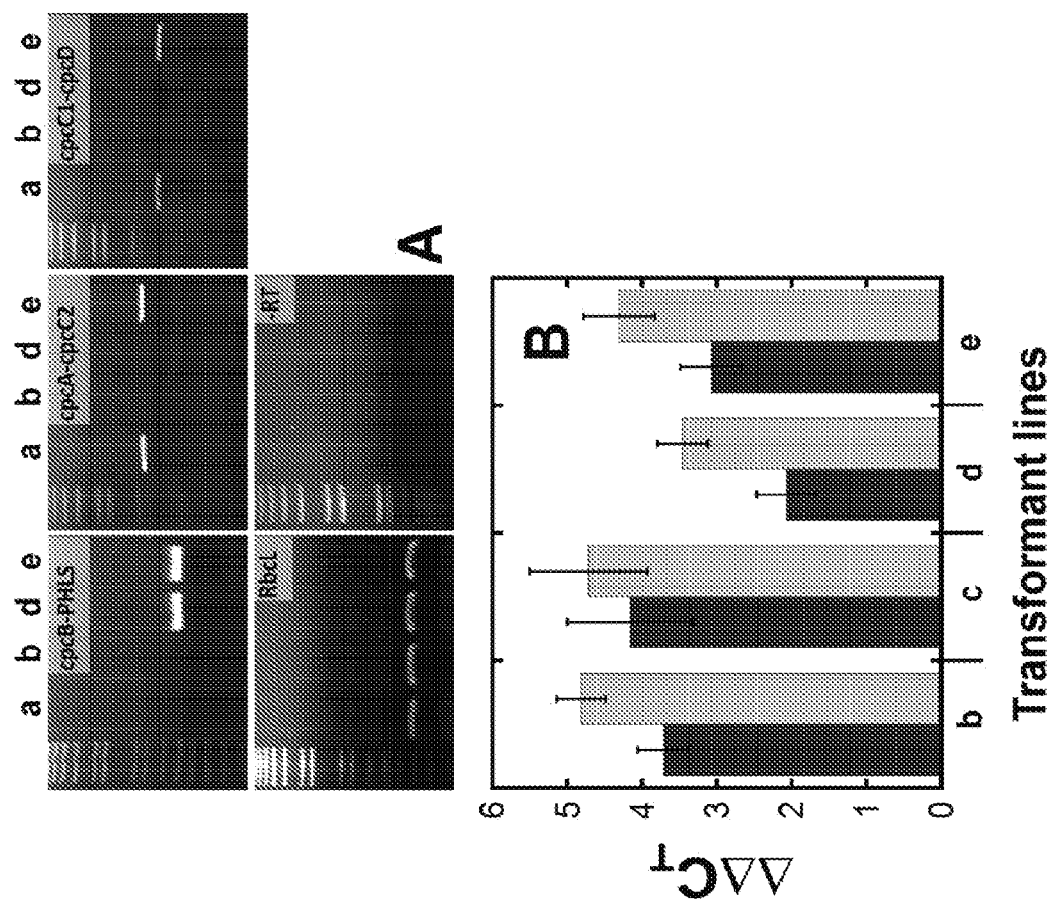
FIG. 3 A. Qualitative RT-PCR analysis of the transcription of the cpcB·PHLS and cpc genes in the wild type and PHLS transformants. A cDNA fragment, including the 3'end of the leading cpcB sequence and the 5' beginning sequence of the PHLS, was amplified with primers cpcB·PHLS_Fw and cpcB·PHLS_Rv (Table 1S). The Δcpc+cpcB·PHLS and cpcB·PHLS+cpc transformants showed evidence of transcription of the fusion cpcB·PHLS sequence (cpcB-PHLS, lanes d, e). The wild type and the PHLS transformant yielded no RT-PCR products (cpcB-PHLS, lanes a, b). A cDNA fragment, including the 3'end of cpcA and the 5' beginning sequence of cpcC2, was amplified with primers cpcA-cpcC2_Fw and cpcA-cpcC2_Rv (Table 1S) only in the wild type and in the cpcB·PHLS+cpc transformant (cpcA-cpcC2, lanes a, e). The PHLS and cpcB·PHLS transformants that replaced the cpc operon yielded no RT-PCR products (cpcA-cpcC2, lanes b, d). Similarly, a cDNA fragment including the 3' end of cpcC1 and the 5' beginning sequence of cpcD was amplified with primers cpcC1-cpcD_Fw and cpcC1-cpcD_Rv (Table 1S) only in the wild type and in the cpcB·PHLS+cpc transformant (cpcC1-cpcD, lanes a, e). The PHLS and cpcB·PHLS transformants that replaced the cpc operon yielded no RT-PCR products (cpcA-cpcD, lanes b, d). These results showed expression of the cpc genes at the transcriptional level in the cpcB·PHLS+cpc transformant. Transcription begins with the cpcB·PHLS sequence and continues along the downstream cpc genes in a policistronic configuration. In contrast, transcription of cpcA, cpcC2, cpcC1 and cpcD was not seen in the Δcpc+PHLS and Δcpc+cpcB·PHLS strains, because the cpc operon was replaced by the transgenic construct (cpcA-cpcC2, cpcC1-cpcD, lanes b, d). Transcription of the RubisCO large subunit was used as positive control (RbcL), while reactions where the reverse transcriptase was not added constituted the negative control, testing absence of contaminating genomic DNA (panel marked −RT). In all RT-PCR reactions, 2.4 μg of cDNA were used as template. B. Transcript levels of the PHLS transgene in different Synechocystis transformants. Transformant lines b through e were generated by constructs b through e as shown in FIG. 1. The transcript steady state level of PHLS was measured by real time RT-qPCR and normalized to the expression of the rnpB (reference gene), used as internal control under the same experimental conditions. Two different sets of primers were employed, one at the 3'end of the PHLS coding sequence (black) and the other at the 5' end of the PHLS coding sequence (grey). Three independent transformant lines were considered for the analysis of each genotype.

Transcription of the PHLS transgene and of the cpc native genes was assessed by RT-PCR (FIG. 3A). This analysis showed transcription of the cpc genes in the CpcB·PHLS+cpc transformant (FIG. 1e), but not in the Δcpc+PHLS (FIG. 1b) and Δcpc+cpcB·PHLS (FIG. 1d) strains. The latter is consistent with the deletion of the cpc operon. Steady state levels of PHLS transcripts were further measured by Real Time RT-qPCR (FIG. 3B). The Δcpc+PHLS (FIG. 3B, column b), Δcpc+CpcB(30 nt)·PHLS (FIG. 3B, column c) and cpcB·PHLS+cpc (FIG. 3B, column e) transformants all showed consistently high levels of PHLS transcription under the control of the cpc operon promoter. Slightly lower PHLS transcript abundance was observed in the Δcpc+cpcB·PHLS strain (FIG. 3B, column d) suggesting a minor differential rate of transcription or transcript stability, resulting in a slightly lower steady state level, as compared to that of the other transformants.

Transgenic Protein Accumulation

Figure 4:
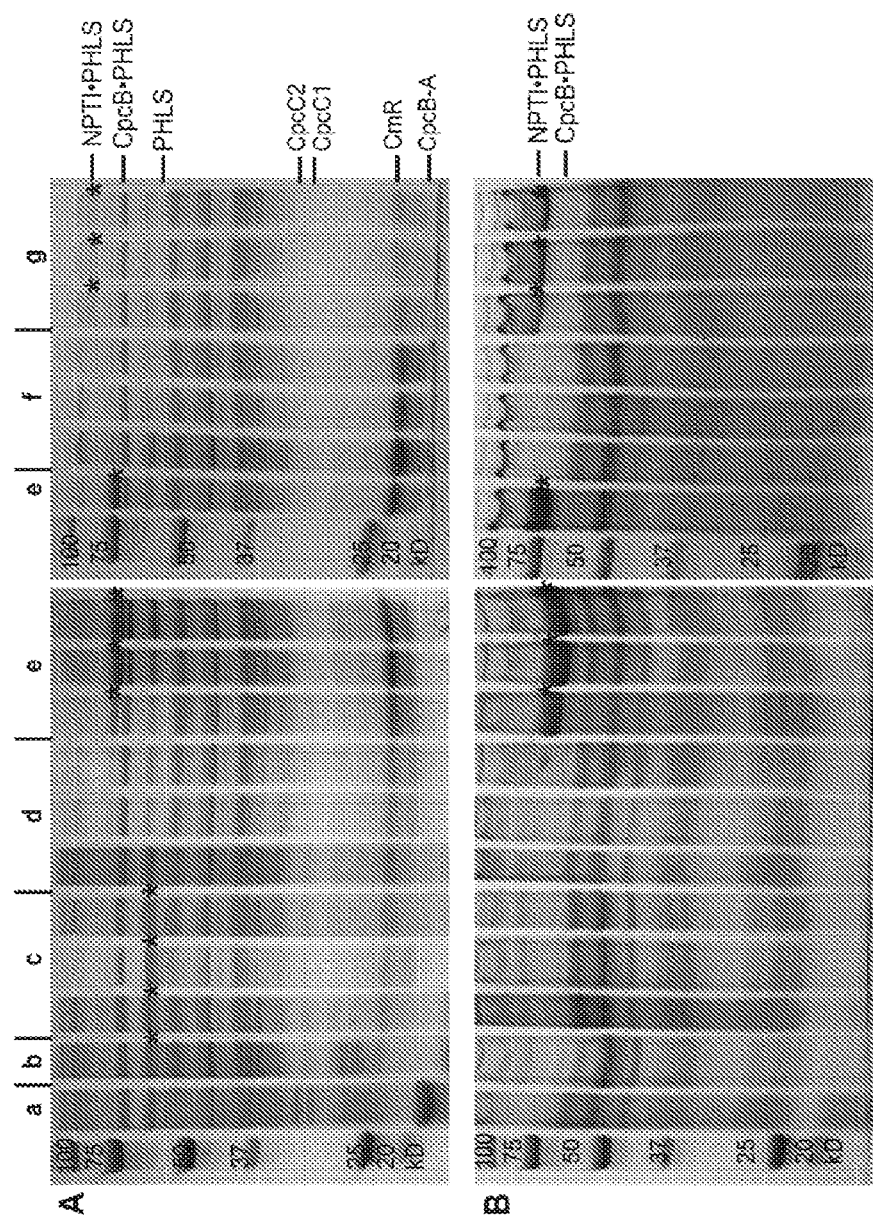
FIG. 4 SDS-PAGE analysis of the total protein extracts from Synechocystis wild type and PHLS transformants. Strains a through g were generated by constructs a through g as shown in FIG. 1. Three independent transformant lines were considered for the analysis of each genotype. Molecular weight markers are indicated in kD. Proteins of interest are labeled and marked with asterisks. A Coomassie-stained SDS-PAGE profile of proteins of cell lysate supernatant fractions. B Coomassie-stained SDS-PAGE profile of proteins of cell lysate pellet fractions.

*Synechocystis* wild type and transformants cells were broken by French press treatment. Supernatant and pellet fractions were separated to improve resolution of the cell constituent proteins. Supernatant (FIG. 4A) and pellet (FIG. 4B) protein extracts were resolved by SDS-PAGE. Low levels of the PHLS protein (~64 kD) were detected in the Coomassie-stained gel in the supernatant fraction of Δcpc+PHLS (FIG. 4A, lane b, marked with an asterisk) and Δcpc+cpcB(30 nt)·PHLS transformants (FIG. 4A, lanes c, marked with asterisks). It is evident that fusion of PHLS to the first 10 amino acids of CpcB protein did not substantially increase the PHLS protein expression level. In the Δcpc+cpcB·PHLS (FIG. 4, lanes d) and cpcB·PHLS+cpc(−cpcA) (FIG. 4, lanes f) transformants, the CpcB·PHLS fusion protein (expected molecular weight of 82 kD) could not be detected upon Coomassie staining of the gels suggesting low transgenic protein expression. In contrast, the CpcB·PHLS fusion protein accumulated to high levels in the cpcB·PHLS+cpc (FIG. 1e) transformant. A protein band migrating to about 75 kD was detected, both in the supernatant and pellet fractions of these cpcB·PHLS+cpc transformants (FIG. 4, lanes e, CpcB·PHLS marked with asterisks). This protein band was absent from the wild type and other transformant extracts. The results indicated that expression of PHLS as a fusion with the CpcB protein can result in substantial recombinant protein accumulation, when the rest of the cpc operon, and in particular the cpcA, is in place.

The premise of a fusion construct in the amplification of transgene expression was examined further in detail, first upon replacing the cpcB gene with a highly expressing kanamycin resistance sequence (Kirst et al. 2014). The rationale behind this design was to test if highly expressed genes, other than the cpcB gene, could act as lead fusion sequences for the amplification of expression of the PHLS transgene. The NPTI·PHLS fusion protein with an expected molecular weight of 95 kD, was clearly visible, especially so in the Coomassie-stained gel of the pellet fractions (FIG. 4, lanes g). It is concluded that a highly expressed gene (cpcB or NPTI), when placed as the lead sequence in a fusion construct, will cause amplification in the expression of the trailing transgene.

Figure 5:
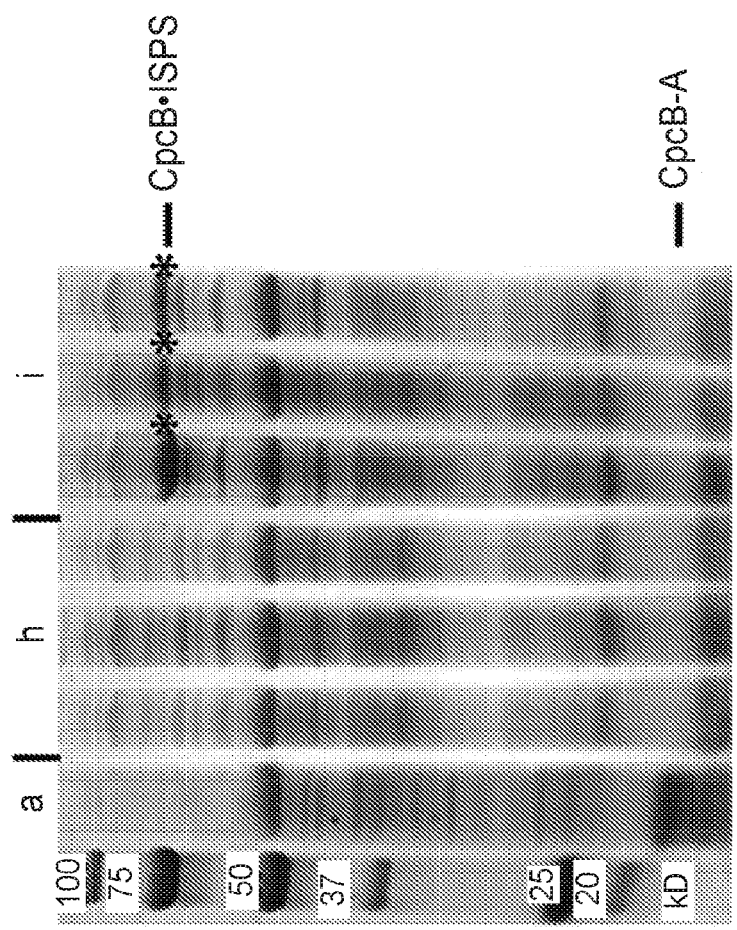
FIG. 5 SDS-PAGE analysis of the total protein extracts from Synechocystis wild type (a) and ISPS transformant lines (h, i). Strains a, h, and i were generated by constructs a, h, and i shown in FIG. 1. Three independent transformant lines were considered for the analysis of each genotype. Shown is the SDS-PAGE profile of total protein extracts from Synechocystis wild type (a) and ISPS transformants (h and i). Molecular weight markers are indicated in kD. Proteins of interest are labeled and marked with asterisks.

The above notion of substantial enhancement in transgene expression as a fusion protein with a highly expressed native protein was further tested upon placement of the isoprene synthase gene from kudzu (Lindberg et al. 2010; Bentley and Melis 2012) as a fusion with the cpcB gene (FIG. 1h, i). Thus, the CpcB fusion strategy with the isoprene synthase protein (ISPS) was designed to test if this approach could be successful in the accumulation of a different transgenic protein. Shown in FIG. 5 are the results, where the CpcB·ISPS fusion protein, with an expected molecular weight of 84 kD, accumulated to high levels in the cpc+cpcB·ISPS transformant (FIG. 5, lanes i), but not in Δcpc+cpcB·ISPS (FIG. 5, lanes h), mirroring the results obtained with CpcB·PHLS.

Figure 6:
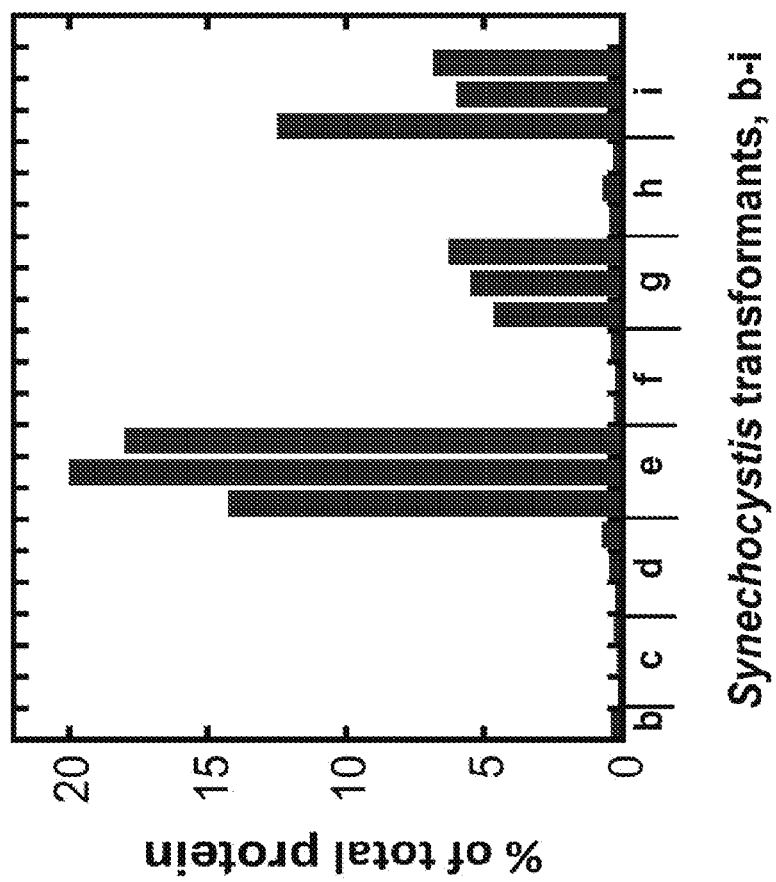
FIG. 6 Densitometric analysis of protein bands shown in FIGS. 4 and 5. The Coomassie-stained band intensity of recombinant PHLS and ISPS proteins was normalized to the total lane protein loading and expressed as a percentage of the total. The analysis was performed with GelPro Analyzer software. *Synechocystis* transformants (b) through (i) measure the transgene expression level derived from constructs b-i shown in FIG. 1.

Quantification of transgenic protein accumulation, as a function of total cell protein, is provided in FIG. 6. Relative amounts of the recombinant proteins are based on Coomassie staining and corroborate the results, as qualitatively shown in FIGS. 4 and 5. The highest recombinant protein accumulation was observed in the cells transformed with the cpcB·PHLS+cpc construct, reaching up to 20% of total cell protein (FIG. 6, lanes e). The next highest accumulation of transgenic protein was observed in the cells transformed with the CpcB·ISPS+cpc construct, reaching up to 10% of total cell protein (FIG. 6, lanes i). The fusion construct with NPTI as leader sequence (FIG. 1g) also produced noticeable amounts of the transgenic protein (FIG. 6, lanes g), although this was not as pronounced as the PHLS and ISPS proteins with the CpcB leader sequence.

Modulation of CpcB·PHLS Expression by CpcA

Of interest is the observation that inclusion of the cpcA gene downstream of the cpcB·PHLS fusion construct was required to enhance accumulation of the CpcB·PHLS fusion protein. To gain a better understanding of this property in the transgenic systems, SDS-PAGE and Western blot analysis with anti-CpcA polyclonal antibodies (Abbiotec) was employed to test for the relative level of expression of the β- and α-phycocyanin subunits. (These polyclonal antibodies cross-react with both the β- and α-phycocyanin protein subunits.) Wild type *Synechocystis* protein extracts showed an abundance of CpcB and CpcA proteins in the supernatant fraction, with the protein bands being clearly visible in equimolar quantities both in the Coomassie-stained SDS-PAGE profile (FIG. 7A, lane a, supernatant) and in the Western blot analysis (FIG. 7B, lane a, supernatant).

*Synechocystis* CpcB·PHLS+cpc protein extracts showed an abundance of the CpcB·PHLS fusion protein in both the supernatant and pellet fractions; with the protein band migrating to about 75 kD in the Coomassie-stained SDS-PAGE (FIG. 7A, lanes e) and in the Western blot analysis (FIG. 7B, lanes e). For the latter, the polyclonal antibody recognized the CpcB protein in spite of its occurrence as a CpcB·PHLS fusion.

Figure 7:
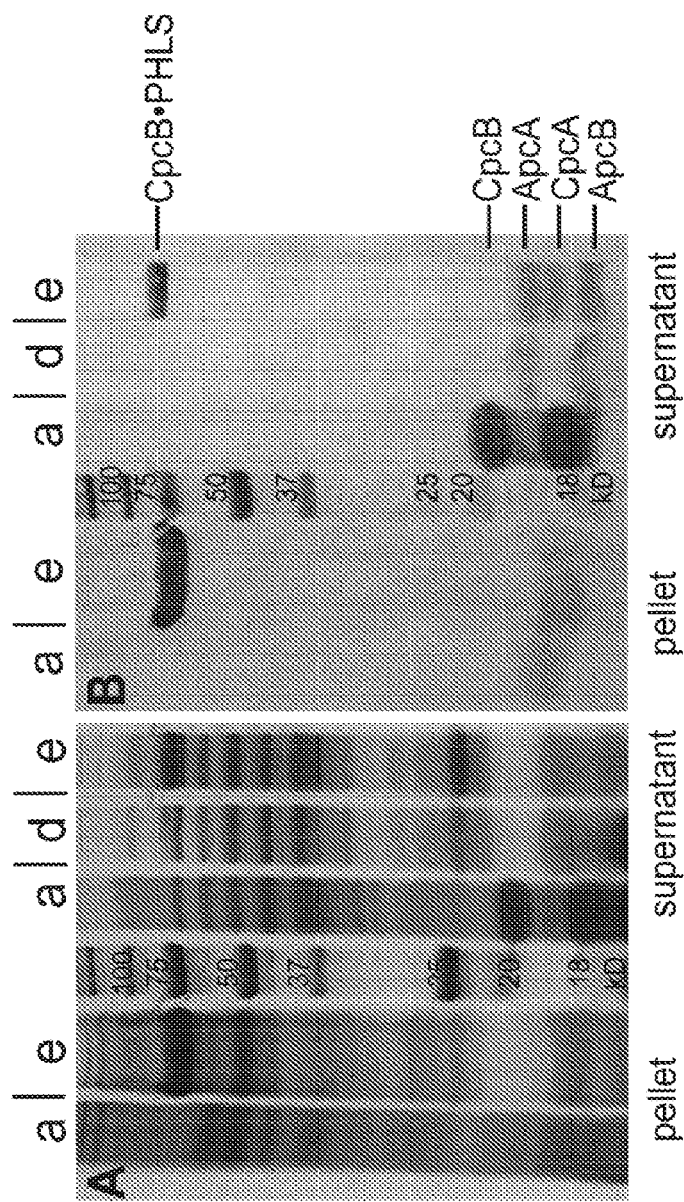
FIG. 7 Analysis of Cpc protein expression in *Synechocystis* wild type and PHLS transformants. Strains a, d, and e were generated by constructs a, d, and e shown in FIG. 1. (A) Total protein of *Synechocystis* cell lysate pellet and supernatant fractions, as indicated, were resolved by SDS-PAGE and visualized by Coomassie staining. (B) Western blot analysis of the SDS-PAGE-resolved proteins shown in (A), obtained upon incubation with CpcA polyclonal antibodies (Abbiotec). The endogenous Cpc and Apc subunits, and CpcB within the CpcB·PHLS fusion, were also recognized by the antibodies and are accordingly labeled.

Low levels of the CpcA protein were detected by Western blot analysis in the CpcB·PHLS+cpc supernatant fraction (FIG. 7B, lane e). Traces of CpcA were in far lower quantity than the CpcB·PHLS fusion protein, and also lower than the CpcA protein measured in the wild type. For comparison purposes, the Δcpc+cpcB·PHLS transformant showed no detectable amounts of the CpcB·PHLS fusion protein or of the CpcA subunit (FIG. 7, lanes d).

Analysis of PHLS Polyribosomes Profile

The PHLS protein from the Δcpc+PHLS transformant and the CpcB·PHLS fusion protein from cpcB·PHLS+cpc were expressed from equally abundant transcripts (FIG. 3B) and were both stable against proteolysis. However, the steady state level of the two recombinant proteins under physiological growth conditions was substantially different (FIG. 4, lane b vs. lanes e). These results suggested that post-transcriptional events, other than protein stability, are responsible for the observed protein expression difference.

Figure 8:
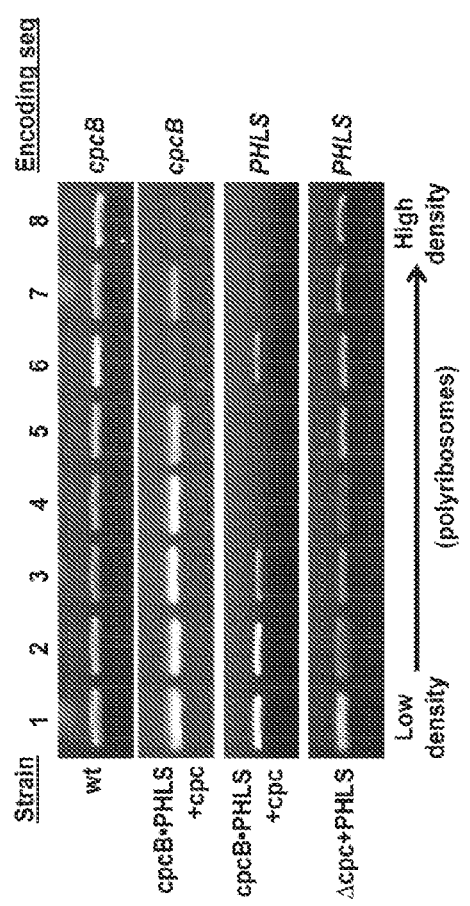
FIG. 8 Analysis of polyribosomes profile. *Synechocystis* total cell cleared lysates were resolved by 10-40% sucrose gradient ultracentrifugation. Fractions obtained were numbered from low to high sucrose gradient concentration (1-8), corresponding to low-density and high-density polyribosomes. Semi-quantitative RT-PCR was performed on each gradient fraction from the wild type, the cpcB·PHLS+cpc and Δcpc+PHLS transformant strains, specified on the left side of the figure. The RT-PCR sequence probed is specified on the right side of the figure. This experiment was repeated in three independent biological replicates. Shown are representative results upon amplification of either the cpcB or PHLS genes (specified on the right side of the figure).

In order to investigate if the different PHLS protein expression levels in Δcpc+PHLS and cpcB·PHLS+cpc transformants are due to a different translation rate and/or efficiency, the polyribosomes distribution profile of the PHLS transcript was assayed upon polyribosomes sucrose gradient ultracentrifugation (FIG. 8). This analysis is based on the fact that, in actively growing cells, multiple ribosomes simultaneously engage in the translation of the same mRNA. The rate and efficiency of ribosome migration on the mRNA molecule determines translation rate and efficiency. In particular, the percentage of ribosomes migrating as polyribosomes is 30% in bacteria, vs. 90% in eukaryotes. This difference is attributed to the fact that protein elongation (i.e., translation) is faster in prokaryotes resulting in a minimal dwell time of ribosomes on the mRNA. While a high density of polyribosomes in eukaryotes is associated with highly translated transcripts, in prokaryotes this is more often attributed to a ribosome pile-up, when a slower ribosome migration rate on the mRNA causes multiple ribosomes to associate with the same mRNA (Qin and Fredrick 2013).

Polyribosomes can be resolved by sucrose gradient ultracentrifugation since each ribosome adds substantial mass to the complex (Qin and Fredrick 2013). Polyribosomes in cleared lysates from wild type, Δcpc+PHLS and cpcB·PHLS+cpc transformants were separated upon sucrose gradient ultracentrifugation, and a semi-quantitative RT-PCR analysis was undertaken on each of the eight fractions that were collected from the gradient, amplifying either cpcB or PHLS (FIG. 8, oligonucleotide primer sequences are reported in Table 1). The signal intensity of the RT-PCR product, when the PCR reaction was terminated before saturation, depends on the abundance of the target transcript in that particular sucrose gradient fraction. The results of FIG. 8 are representative of independent biological replicates, and they showed that the cpc operon transcript in the wild type is associated about evenly with low-density and high-density polyribosomes (FIG. 8, wt). The cpcB·PHLS transcripts in the cpcB·PHLS+cpc transformant cleared lysates are also associated with both low-density and high-density polyribosomes. However, the distribution is not even in this case, as there is a gradient with a greater number of low-density than high-density polyribosomes (FIG. 8, cpcB·PHLS+cpc). This result was reproducible regardless of whether primers specific to cpcB or PHLS encoding sequences were tested, and suggests a short dwell time of ribosomes on the cpcB·PHLS transcript. Insertion of the cpcB·PHLS+cmR construct may also have induced a ribosome drop-off at the end of cpcB·PHLS+cmR. Consistent with this hypothesis is the substantially lower expression level of the subsequent operon genes in the cpcB·PHLS+cpc transformant (FIG. 7).

In contrast, the PHLS transcript in the Δcpc+PHLS transformant, although much shorter, is associated with a higher polyribosome density than the cpcB·PHLS transcript in cpcBPHLS+cpc (FIG. 8, Δcpc+PHLS). Considering the low PHLS protein level in the Δcpc+PHLS transformant (FIG. 4, lane b), this result may suggest a longer dwell time of ribosomes on the PHLS transcript in the Δcpc+PHLS transformants.

Functional Analysis of *Synechocystis* Wild Type and PHLS Transformants

Figure 9:
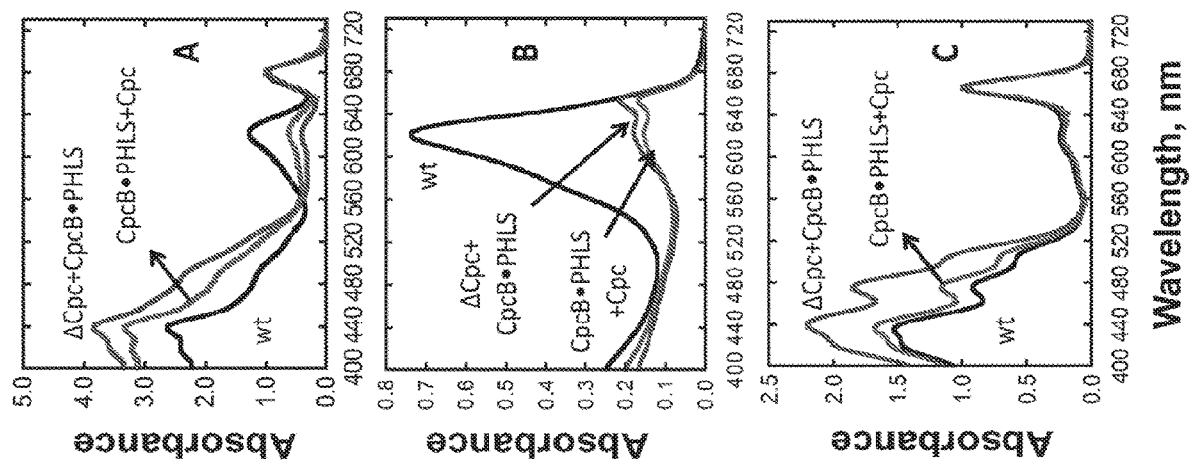
FIG. 9 Absorbance spectra of photosynthetic pigments from *Synechocystis*. A. Absorbance spectra of total cell extracts following disruption by French press of wild type, Δcpc+cpcB·PHLS and cpcB·PHLS+cpc transformants. Spectra were normalized to the chlorophyll a absorbance peak at 678 nm. B. Absorbance spectra of the soluble (supernatant) fraction of cell lysates measured on the same strains as in (A). C. Absorbance spectra of chlorophyll a and carotenoids extracted in 90% methanol, same strains as in (A, B). Spectra were normalized to the chlorophyll a absorbance peak at 665.6 nm. All spectra are average results from three biological replicates per genotype and have standard deviations of the mean within 10% of the presented results.

Absorbance spectroscopy of cell lysates from the wild type showed typical absorbance bands of chlorophyll (Chl) a at 680 nm and phycocyanin (Phc) at 625 nm (Glazer and Hixon, 1975; Glazer 1989), plus a Soret absorbance in the blue region of the spectrum from Chl a and carotenoids (FIG. 9A, wt). The Δcpc+cpcB·PHLS transformant showed the Chl a absorbance band at 680 nm and the Soret absorbance, whereas the Phc absorbance peak at 625 nm was missing (FIG. 9A, Δcpc+cpcB·PHLS), consistent with a ΔCpc phenotype (Kirst et al. 2014; Formighieri and Melis 2014a). In the cpcB·PHLS+cpc transformant, the 625 nm absorbance was detected but at lower levels compared with that in the wild type (FIG. 9A, cpcB·PHLS+cpc).

Cell lysates were separated into supernatant and heavy-fraction pellet. Absorbance spectroscopy was applied to the supernatant fractions, expected to contain the dissociated phycobilisome. The wild type supernatant was blue, dominated by the absorbance of Phc at 625 nm (FIG. 9B, wt). In contrast, the Δcpc+cpcB·PHLS transformant showed a featureless low absorbance at 625 nm (FIG. 9B, Δcpc+cpcB·PHLS), and a more pronounced absorbance band at 650 nm attributed to APC (Glazer 1989). The cpcB·PHLS+cpc transformant showed the same absorbance features as Δcpc+cpcB·PHLS in the soluble fraction (FIG. 9B, cpcB·PHLS+cpc). No minor absorbance band at 625 nm could be observed, opposite to what was detected in the total cell lysate of cpcB·PHLPS+cpc (FIG. 9A). This result suggested that 625 nm absorbance contributions from the cpcB·PHLS+cpc transformant is Phc in the CpcB·PHLS fusion protein that retained the ability to bind bilins, and which preferentially partitioned with the pellet fraction (FIG. 4, lanes e). It is concluded that a functional PBS antenna does not assemble in either the Δcpc+cpcB·PHLS or cpcB·PHLS+cpc transformant (FIG. 9B).

Chlorophyll a and carotenoids were extracted in 90% methanol prior to measuring the absorbance spectra of the extracts (FIG. 9C). A higher Soret absorbance relative to that in the red was observed in the Δcpc+cpcB·PHLS transformant over that in the wild type (FIG. 9C), suggesting a greater Car/Chl ratio in the former (Kirst et al. 2014; Formighieri et al. 2014a).

Figure 10:
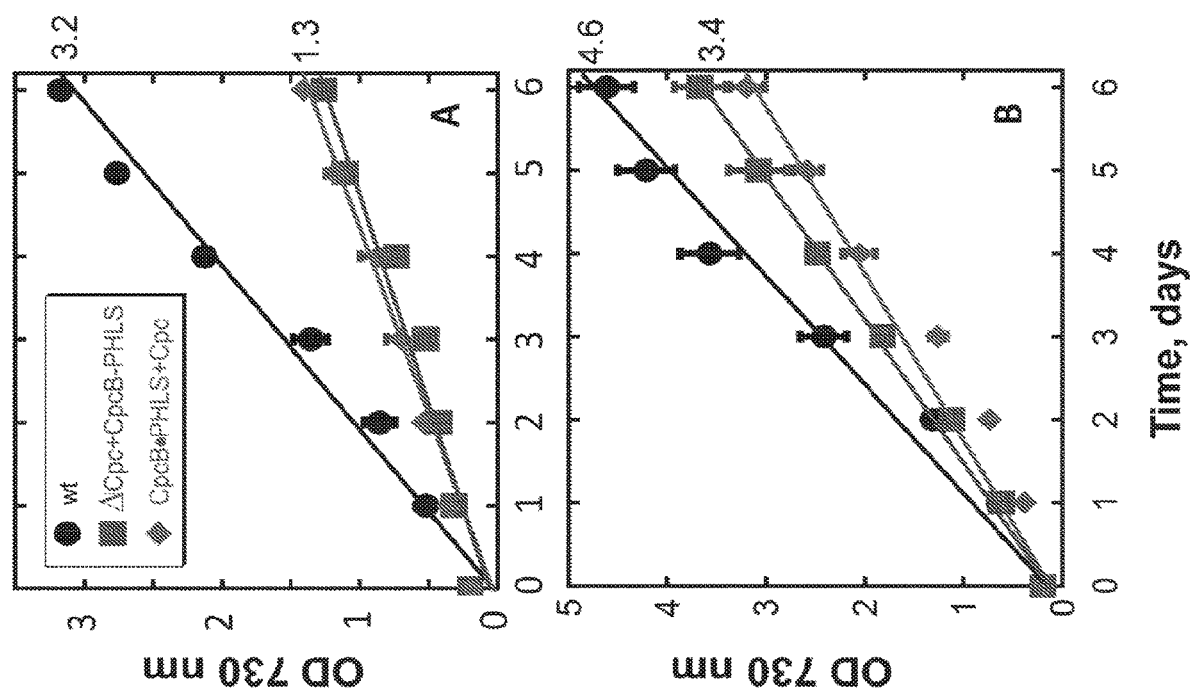
FIG. 10 Growth curves of *Synechocystis* wild type, Δcpc+CpcB·PHLS and cpcB·PHLS+cpc transformants, as measured from the optical density (OD) of the cultures at 730 nm. A. Cells were grown under 50 μmol photons $m^{-2}$ $s^{-1}$ of incident light intensity. B. Cells were grown under 170 μmol photons $m^{-2}$ $s^{-1}$ of incident light intensity. Averages and standard deviations were calculated from three independent biological replicates for each genotype. Cultures were inoculated to an OD at 730 nm of about 0.2, as the initial cell concentration in the growth experiment. Best fit of the points from the cell-density measurements were straight lines, reflecting a deviation from exponential growth due to increasing cell density and shading, gradually limiting the effective light intensity through the cultures.
Figure 11:
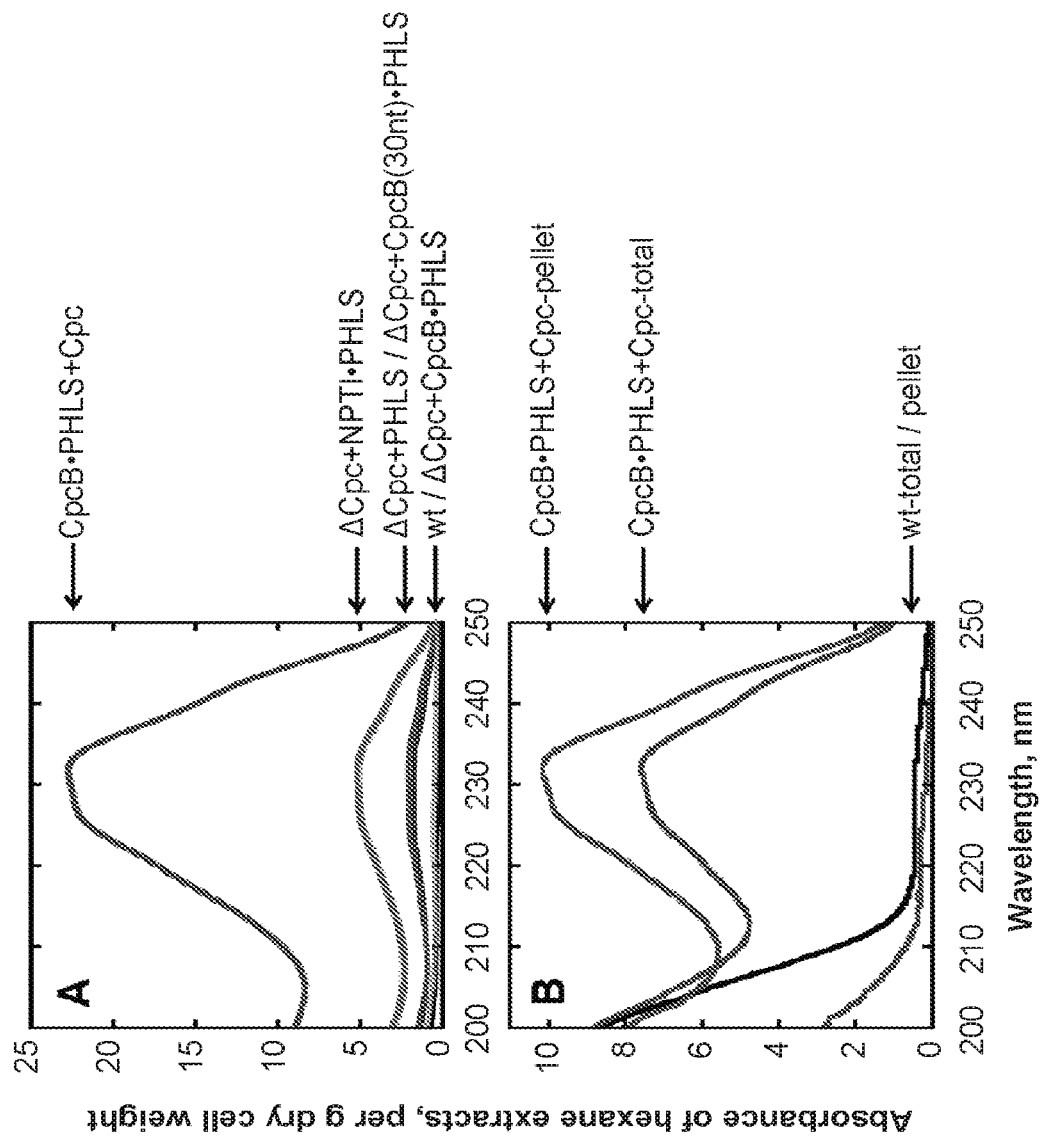
FIG. 11 β-Phellandrene hydrocarbons production assay by *Synechocystis* transformants. A. β-Phellandrene hydrocarbons was collected as a non-miscible compound floating on top of the aqueous phase of live and actively photosynthesizing *Synechocystis* cultures. β-Phellandrene was diluted with a known amount of hexane and siphoned off the top of the growth medium. Absorbance spectra were normalized on per g of dry cell weight (dcw) and refer to 15 mL of hexane extracts. Averages were calculated from three independent biological replicates for each genotype. Calculated β-phellandrene yields are reported in Table 2. B. β-Phellandrene hydrocarbons synthesis was assayed in vitro after *Synechocystis* cell disruption, measured on total cell extracts, and with pellet fractions following centrifugation. Reaction mixtures were incubated with 50 μM of added GPP for 1 hour at 30° C. A small volume of hexane over-layer was applied from the beginning of the reaction for product sequestration. Absorbance spectra of the hexane extracts were normalized on a per g of dry cell weight (dcw) basis and refer to 1 mL of hexane solution. Averages were calculated from three independent biological replicates, error bars are within 20% of the presented results.

Photoautotrophic growth was measured with the wt and the CpcB·PHLS transformants. At 50 µmol photons $m^{-2} s^{-1}$, the ΔCpc+cpcB·PHLS and cpcB·PHLS+cpc transformants grew with only about 30% of the rate measured with the wild type (FIG. 10A). When grown at 170 µmol photons $m^{-2} s^{-1}$, rate of growth accelerated for the wild type by about 35%, whereas rate of growth for the ΔCpc+cpcB·PHLS and cpcB·PHLS+cpc transformants accelerated by 280% (FIG. 10B). These results are consistent with the phenotype of ΔCpc mutants (Kirst et al. 2014; Formighieri et al. 2014a), and with the notion that strains with a truncated light-harvesting antenna size have a diminished light-harvesting capacity, a disadvantage under limiting light conditions that translates in lower photosynthetic productivity. However, this phenotype is alleviated as growth irradiance increases. Comparable rates of cell growth for the ΔCpc+cpcB·PHLS and cpcB·PHLS+cpc transformants under all tested irradiances suggested that accumulation of the CpcB·PHLS protein to high levels in the latter does not exert a negative impact on cell growth and biomass accumulation.

β-Phellandrene hydrocarbons production in PHLS transformants

β-Phellandrene was collected as a non-miscible compound floating on top of the aqueous medium of transformant cultures. The floating β-phellandrene product was diluted upon addition of hexane, siphoned off the culture and quantified by absorbance spectroscopy, where the compound is distinguished by a specific absorbance in the UV region of the spectrum, showing a primary peak at 232.4 nm in hexane (Formighieri and Melis 2014a, 2014b). FIG. 11A shows the absorbance spectra of hexane extracts from the wild type and PHLS transformants, normalized on a per g of dry cell weight (dcw) of the biomass at the end of a 48 h cultivation period. Related yields of β-phellandrene as mg β-PHL $g^{-1}$ dcw are reported in Table 2 and referred to three independent transformant lines for each genotype. The ΔCpc+PHLS transformant produced about 0.2 mg β-PHL $g^{-1}$ dcw (Table 2). The ΔCpc+cpcB(30 nt)·PHLS transformant yielded comparable β-phellandrene amounts (about 0.3 mg β-PHL $g^{-1}$ dcw), consistent with PHLS protein expression levels (FIG. 4, lanes b, c). The ΔCpc+cpcB·PHLS transformant yielded lower β-phellandrene amounts (0.04 mg β-PHL $g^{-1}$ dew), a result that relates to the low CpcB·PHLS protein expression in this strain (FIG. 4, lanes d). In contrast, the cpcB·PHLS+cpc transformant (FIG. 1e; FIG. 4, lanes e) yielded an average of 3.2 mg β-PHL $g^{-1}$ dew (Table 2). This constitutes a 16-fold yield increase over that of the ΔCpc+PHLS strain (Table 2). The NPTI·PHLS transformant generated an intermediate yield of 0.64 mg β-PHL $g^{-1}$ dcw (FIG. 11A and Table 2).

TABLE 2

β-Phellandrene hydrocarbons production measurements over a 48 h photoautotrophic cultivation of Synechocystis transformants. Yields are expressed as mg of β-phellandrene per g of dry cell weight (dcw). Three independent transformant lines were tested for each genotype, with corresponding averages and standard deviations of the mean.

| | β-phellandrene, mg $g^{-1}$ dcw Transformant lines | | |
|---|---|---|---|
| Genotype | a | b | c |
| ΔCpc + PHLS | 0.24 ± 0.08 | 0.16 ± 0.03 | 0.21 ± 0.04 |
| ΔCpc + CpcB(10 nt) · PHLS | 0.40 ± 0.20 | 0.22 ± 0.13 | 0.35 ± 0.09 |
| ΔCpc + CpcB · PHLS | 0.05 ± 0.02 | 0.02 ± 0.01 | 0.03 ± 0.02 |

TABLE 2-continued

β-Phellandrene hydrocarbons production measurements over a 48 h photoautotrophic cultivation of Synechocystis transformants. Yields are expressed as mg of β-phellandrene per g of dry cell weight (dcw). Three independent transformant lines were tested for each genotype, with corresponding averages and standard deviations of the mean.

| | β-phellandrene, mg $g^{-1}$ dcw Transformant lines | | |
|---|---|---|---|
| Genotype | a | b | c |
| CpcB · PHLS + Cpc | 3.70 ± 0.48 | 2.57 ± 0.50 | 3.28 ± 0.90 |
| ΔCpc + NPTI · PHLS | 0.72 ± 0.10 | 0.62 ± 0.2 | 0.56 ± 0.14 |

The activity of the β-phellandrene synthase was additionally assessed in vitro with total cell extracts, after cell disruption, or with the pellet fraction following centrifugation. FIG. 11B compares the results obtained with the wild type and the CpcB·PHLS+Cpc transformant. While the wild type extracts gave a featureless flat absorption spectrum, both total cell extracts and pellet fractions from the CpcB·PHLS+Cpc transformant yielded measurable amounts of β-phellandrene, detected as a clear UV absorbance. This in vitro experiment showed that the CpcB·PHLS fusion protein recovered from the pellet fraction (FIG. 4, 7, lanes e) is active in product generation.

Figure 12:
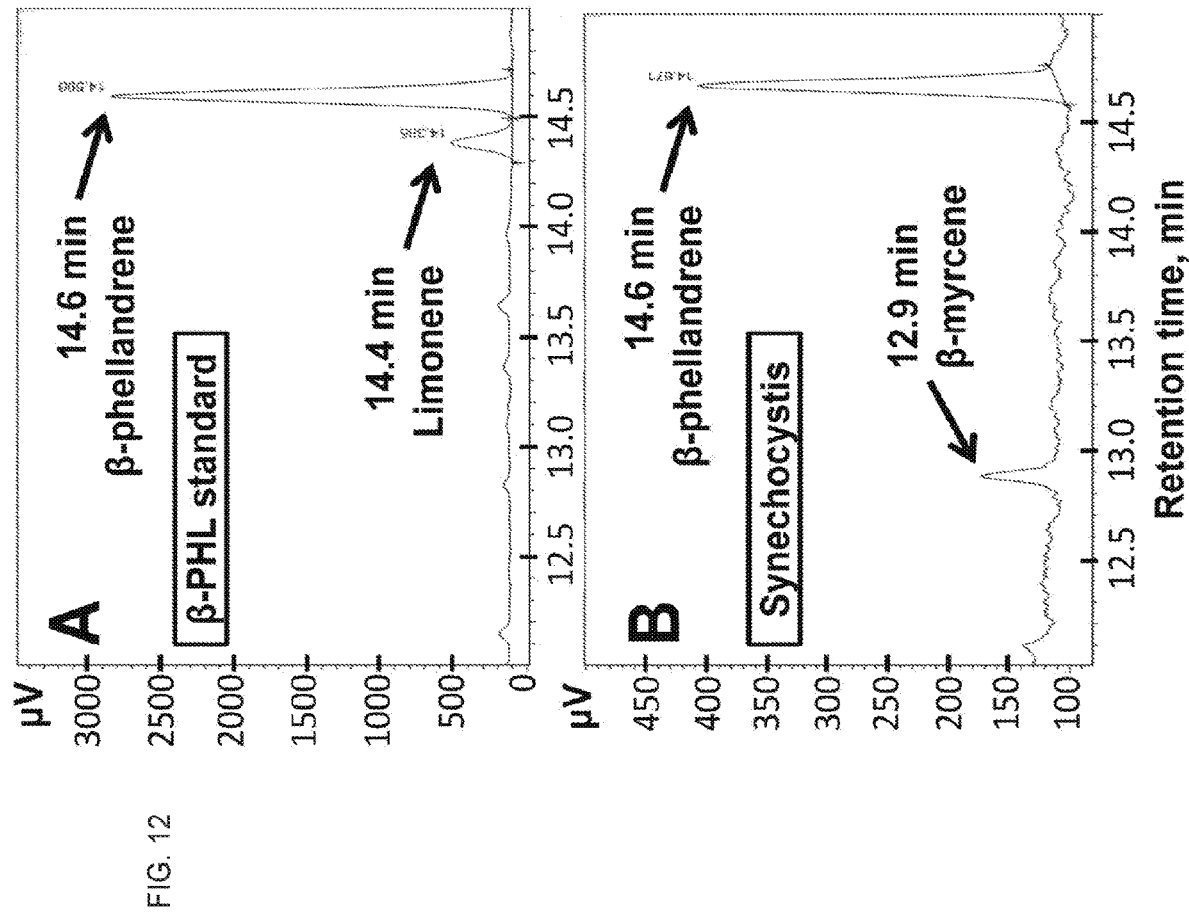
FIG. 12 GC-FID sensitive analysis of hexane extracts from PHLS transformant *Synechocystis* cultures. A. GC-FID analysis of a β-phellandrene standard (Chemos GmbH) showing a retention time of 14.6 min under these conditions. The β-phellandrene standard contained other monoterpenes and the main impurity was limonene (retention time of 14.4 min). B. GC-FID analysis of hexane extracts from cpcB·PHLS+cpc transformant lines, showing the presence of β-phellandrene (retention time of 14.6 min) as the major product, confirmed by GC-MS, and of β-myrcene as a minor byproduct (retention time of 12.9 min). GC-FID analysis of hexane extracts from wild type cultures, measured under the same conditions, displayed a flat profile, showing no discernible peaks in the 5-20 min retention time region (not shown).

FIG. 12 shows the GC-FID profile of the hexane extract from the cpcB·PHLS+cpc transformants, as compared to that of a β-phellandrene standard. The results showed the presence of β-phellandrene as the major product with a retention time of 14.6 min. A small amount of limonene was detected in the β-phellandrene standard, and a small amount of β-myrcene was detected as the byproduct of the recombinant PHLS enzymatic activity (Formighieri and Melis 2014b).

Discussion of Experimental Results Provided in EXAMPLES Section

Aquatic organisms, both unicellular and multicellular, do not have a native ability to generate essential oils such as monoterpenes, as these systems lack endogenous monoterpene synthase genes required for their synthesis (Van Wagoner et al. 2007). In nature, monoterpene synthesis and accumulation in specialized organs, the trichomes, is a trait of terrestrial plants only. This example illustrates the production of the monoterpene β-phellandrene in *Synechocystis* transformants heterologously expressing β-phellandrene synthase (PHLS), as a fusion protein with either highly expressed endogenous CpcB or heterologous NPTI.

Cyanobacteria express the methyl-erythritol-4-phosphate (MEP) pathway (Lichtenthaler 2000) to synthesize a wide variety of terpenoid-like molecules for cell function. Carbon flux in photosynthetic systems through the MEP pathway may be naturally up-regulated, compared to heterotrophic organisms, in order to sustain the synthesis and accumulation of carotenoids, phytol moieties of chlorophyll, and prenyl tails of plastoquinone molecules, which constitute the vast majority of isoprenoids serving the photosynthetic apparatus (Formighieri and Melis 2014b). For this reason, the endogenous MEP pathway can sustain heterologous synthesis of terpenes, and expression of PHLS alone is necessary and sufficient to endow *Synechocystis* cells with β-phellandrene biosynthesis. On the other hand, rate and yield in product generation are limited by the amounts of the PHLS enzyme (Formighieri and Melis 2014a). High expression levels of the heterologous terpene synthase are desired to competitively sustain carbon flux toward the desired product.

Phycocyanin (Phc), encoded by the cpcB and cpcA genes, is the most abundant soluble protein in cyanobacteria. Their high level of expression is in part due to strong cis-regulatory elements in the cpc operon promoter that, theoretically, could also be used to efficiently drive expression of transgenes. We first expressed the PHLS transgene under the cpc endogenous promoter. The Δcpc+PHLS strain, obtained by replacing the entire cpc operon with the PHLS gene under the control of the cpc operon promoter, yielded a limited 0.2 mg of β-phellandrene per g of dry cell weigh (dcw) (Table 2), corresponding to a 0.025% β-PHL:Bms (w:w) carbon partitioning ratio. This accounts for only a small fraction of the carbon flux through the cell's own terpenoid biosynthetic pathway, which was estimated to be 4-5% of all photosynthetically fixed carbon (Lindberg et al. 2010).

We concluded that greater amounts of recombinant PHLS protein are needed to further improve product yields. Expression of the PHLS gene under the control of the cpc operon promoter led to relatively low levels of transgenic protein, and nowhere near those of the abundant Phc subunits that are normally expressed under this promoter (FIG. 4, lane b). Our results suggested that expression of the native Phc β- and α-subunits is subject to post-transcriptional regulation, in addition to transcriptional control exerted by the cpc promoter. In the present work, cpcB·PHLS fusion constructs were made in order to test whether a translational enhancement in Phc accumulation might also extend to the heterologous PHLS protein synthesis. The rationale was that the efficiency of translation initiation may contribute to overall protein expression. For example, codons immediately downstream of the translation start (named downstream box, DB) have been shown to affect accumulation of foreign proteins in *E. coli* (Sprengart et al. 1996; Salis et al. 2009), in tobacco chloroplasts (Kuroda and Maliga 2001a; 2001b; Kudla et al. 2009) and in *Synechocystis* (Formighieri and Melis 2014a). The DB sequence was proposed to potentially facilitate unfolding of the mRNA secondary structure and enhance ribosome binding during translation initiation.

PHLS was initially fused to the leading 10 aminoacids of CpcB, testing for the contribution of translation initiation efficiency on overall protein accumulation. However, expression of PHLS (FIG. 4, lanes b, c) and yields of PHL hydrocarbons (Table 2) did not substantially improve in the Δcpc+cpcB(30 nt)·PHLS transformant compared to the Δcpc+PHLS strains. This result suggested that translation initiation, affected by the efficiency of ribosome binding at the 5'UTR and downstream box, is not the absolute factor accounting for the divergent Phc and PHLS protein expression under the same cpc operon promoter.

PHLS was subsequently fused to the C-terminus of the entire CpcB, generating a recombinant fusion protein of 82 kD. The cpc promoter used was the same as in the Δcpc+PHLS strains, and it afforded comparable PHLS transcript abundance (FIG. 3B), thus changes in PHLS protein expression could be attributed to post-transcriptional events. Remarkably, the CpcB·PHLS fusion protein accumulated to very high levels in the cpcB·PHLS+cpc transformant, becoming the most abundant protein in the transformant extracts (FIGS. 4, 6, 7, lanes e). The highly expressed endogenous CpcB thus can be an effective leader fusion sequence, substantially enhancing the expression of the PHLS protein. The notion of substantial enhancement in transgene expression as a fusion protein with a highly expressed native protein, such as CpcB, was further confirmed with an isoprene synthase (ISPS) transgene, expressed as a CpcB·ISPS fusion (FIGS. 5, 6, lanes i).

Furthermore, this example demonstrates that a heterologous NPTI·PHLS fusion construct was made that allowed for substantial NPTI·PHLS protein accumulation (FIGS. 4, 6, lanes g). This demonstrated that highly expressed genes other than cpcB can also act as lead fusion sequences for the amplification of transgene expression The importance of increasing the amount of the recombinant terpene synthase as a pre-requisite for greater product yield was evidenced from the analysis of β-PHL hydrocarbons generation (Table 2). The high level of CpcB·PHLS protein expression supported synthesis of an average of 3.2 mg of β-PHL $g^{-1}$ dcw, corresponding to 0.32% β-PHL:Bms (w:w) ratio (Table 2). NPTI·PHLS expression led to an intermediate product yield of 0.064% β-PHL:Bms (w:w) ratio, consistent with the level of the transgenic protein accumulation.

We observed that CpcB protein fused to PHLS was present in the supernatant and in the pellet of cell lysates, instead of being exclusively in the supernatant, as the case is for the native Cpc subunits (FIGS. 4, 7). This may be due to the PHLS protein and the properties that it confers, resulting in partial accumulation in the pellet. However, PHLS found in the pellet of lysed cells is active in β-phellandrene protein synthesis and β-phellandrene hydrocarbons production (FIG. 11B). PHLS has no predicted transmembrane domain; however, terpene synthases are found both in the plastid stroma of higher plants and thylakoid-membrane pellets (Wildermuth and Fall 1998), such that recombinant PHLS may be partially tethered to membranes and is found in the heavy-fraction pellet of *Synechocystis* transformants.

In addition to transcription and translation initiation, translation elongation is an important regulatory step controlling protein expression (Tyystjarvi et al. 2001). Ribosome queuing and collisions happen during translation, when ribosomes interfere with each other and traffic jams cause delays and pile up of ribosomes, thus causing a substantial delay in producing proteins (Mitarai et al. 2008). An efficient codon distribution, between fast and slow translated regions, especially in the first part of a transcript, regulates the average ribosome distance in the later part, and thereby minimizes ribosomes queues there (Mitarai et al. 2008). The PHLS sequence was codon optimized for transcription in *Synechocystis*, however, this proved to be insufficient to sustain high translation rates. A long dwell time of ribosomes on the PHLS transcript in the Δcpc-PHLS transformant may account for the low protein expression level (FIG. 4, lane b, FIG. 8). In contrast, cpcB is an endogenous sequence that is normally expressed at very high levels and its efficient codon distribution allows for optimal average ribosome distance and translation elongation also of the following heterologous PHLS in the cpcB·PHLS fusion construct. To achieve this result, a cpcB sequence longer than just the first 10 codons was employed.

These examples thus provide illustrative results demonstrating that fusion of a transgene to a highly expressed gene substantially enhances transgene translation and recombinant protein accumulation, beyond a point where the recombinant enzyme is limiting the rate and yield of product formation.

The above examples are provided to illustrate the invention but not to limit its scope. Other variants of the invention will be readily apparent to one of ordinary skill in the art and are encompassed by the appended claims. All publications, patents, patent applications, and accession numbers cited herein are hereby incorporated by reference in their entireties for all purposes.

REFERENCES CITED IN THE APPLICATION BY AUTHOR AND PUBLICATION YEAR

Bentley F K, Melis A (2012) Diffusion-based process for carbon dioxide uptake and isoprene emission in gaseous/aqueous two-phase photobioreactors by photosynthetic microorganisms. Biotechnol Bioeng 109:100-109

Bentley F K, Garcia-Cerdin J G, Chen H C, Melis A (2013) Paradigm of monoterpene (β-phellandrene) hydrocarbons production via photosynthesis in cyanobacteria. BioEnergy Res 6:917-929

Camsund D, Lindblad P (2014) Engineered transcriptional systems for cyanobacterial biotechnology. Front Bioeng Biotechnol 2:40 doi: 10.3389/fbioe.2014.00040

Chen H-C, Melis A (2013) Marker-free genetic engineering of the chloroplast in the green microalga *Chlamydomonas reinhardtii*. Plant Biotech J. 11: 818-828

Demissie Z A, Sarker L S, Mahmoud S S (2011) Cloning and functional characterization of β-phellandrene synthase from *Lavandula angustifolia*. Planta 233:685-696

Ducat D C, Way J C, Silver P A (2011) Engineering cyanobacteria to generate high-value products. Trends Biotechnol 29:95-103

Eaton-Rye J J (2011) Construction of gene interruptions and gene deletions in the cyanobacterium *Synechocystis* sp. strain PCC 6803. Methods Mol Biol 684:295-312

Formighieri C, Melis A (2014a) Regulation of β-phellandrene synthase gene expression, recombinant protein accumulation, and monoterpene hydrocarbons production in *Synechocystis* transformants. Planta 240:309-324

Formighieri C, Melis A (2014b) Carbon partitioning to the terpenoid biosynthetic pathway enables heterologous β-phellandrene production in *Escherichia coli* cultures. Arch Microbiol 196:853-861

Glazer A N, Hixson C S (1975) Characterization of R-phycocyanin. Chromophore content of R-phycocyanin and C-phycoerythrin. J Biol Chem 250: 5487-95.

Glazer A N (1989) Light guides. Directional energy transfer in a photosynthetic antenna. J Biol Chem 264: 1-4.

Halfmann C, Gu L, Zhou R (2014) Engineering cyanobacteria for the production of a cyclic hydrocarbon fuel from CO2 and H2O. Green Chem 16, 3175-3185

Jindou S, Ito Y, Mito N, Uematsu K, Hosoda A, Tamura H (2014) Engineered platform for bioethylene production by a cyanobacterium expressing a chimeric complex of plant enzymes. ACS Synth Biol 3:487-496

Kirst H, Formighieri C, Melis A (2014) Maximizing photosynthetic efficiency and culture productivity in cyanobacteria upon minimizing the phycobilisome light-harvesting antenna size. Biochim Biophys Acta 1837:1653-1664

Kudla G, Murray A W, Tollervey D, Plotkin J B (2009) Coding-sequence determinants of gene expression in *Escherichia coli*. Science 324:255-258

Kuroda H, Maliga P (2001a) Complementarity of the 16S rRNA penultimate stem with sequences downstream of the AUG destabilizes the plastid mRNAs. Nucleic Acids Res 29:970-975

Kuroda H, Maliga P (2001b) Sequences downstream of the translation initiation codon are important determinants of translation efficiency in chloroplasts. Plant Physiol 125:430-436

Lichtenthaler H K (2000) Sterols and isoprenoids. Biochem Soc Trans 28:785-789

Lindberg P, Park S, Melis A (2010) Engineering a platform for photosynthetic isoprene production in cyanobacteria, using *Synechocystis* as the model organism. Metab Eng 12:70-79

Livak K J, Schmittgen T D (2001) Analysis of relative gene expression data using real-time quantitative PCR and the 2-ΔΔCT method. Methods 25:402-408

Meeks J K, Castenholz R W (1971) Growth and photosynthesis in an extreme thermophile, *Synechococcus lividus* (Cyanophyta). Arch Microbiol 78:25-41

Melis A (2012) Photosynthesis-to-fuels: from sunlight to hydrogen, isoprene, and botryococcene production. Energy Environ Sci 5:5531-5539

Mitarai N, Sneppen K, Pedersen S (2008) Ribosome collisions and translation efficiency: optimization by codon usage and mRNA destabilization. J Mol Biol 382:236-245.

Oliver J W K, Atsumi S (2014) Metabolic design for cyanobacterial chemical synthesis. Photosynth Res 120: 249-261

Qin D, Fredrick K (2013) Analysis of polysomes from bacteria. Methods Enzymol 530:159-172

Salis H M, Mirsky E A Voigt C A (2009) Automated design of synthetic ribosome binding sites to control protein expression. Nat Biotechnol 27, 946-950

Savakis P, Hellingwerf K J (2015) Engineering cyanobacteria for direct biofuel production from CO2. Current Opinion in Biotechnology 33:8-14

Sprengart M L, Fuchs E, Porter A G (1996) The downstream box: an efficient and independent translation initiation signal in *Escherichia coli*. EMBO J 15:665-674

Tyystjarvi T, Herranen M, Aro E M (2001) Regulation of translation elongation in cyanobacteria: membrane targeting of the ribosome nascent-chain complexes controls the synthesis of D1 protein. Mol Microbiol 40:476-484

Van Wagoner R M, Drummond A K, Wright J L C (2007) Biogenetic diversity of cyanobacterial metabolites. Adv Appl Microbiol 61:89-217

Wijffels R H, Kruse O, Hellingwerf K J (2013) Potential of industrial biotechnology with cyanobacteria and eukaryotic microalgae. Curr Opin Biotechnol 24:405-413

Wildermuth M C, Fall R (1998). Biochemical characterization of stromal and thylakoid-bound isoforms of isoprene synthase in willow leaves. Plant Physiol 116:1111-1123.

Williams J G K (1988) Construction of specific mutations in photosystem II photosynthetic reaction center by genetic engineering methods in *Synechocystis* 6803. Methods Enzymol 167:766-778

Xue Y, Zhang Y, Grace S, He Q (2014) Functional expression of an *Arabidopsis* p450 enzyme, p-coumarate-3-hydroxylase, in the cyanobacterium *Synechocystis* PCC 6803 for the biosynthesis of caffeic acid. J Appl Phycol 26:219-226

Zhou J, Zhang H, Meng H, Zhu Y, Bao G, Zhang Y, Li Y, Ma Y (2014) Discovery of a super-strong promoter enables efficient production of heterologous proteins in cyanobacteria. Scientific Reports 4: 4500 doi:10.1038/srep04500

Illustrative sequences. Sequences of CpcB · PHLS, NPTI · PHLS and CpcB · ISPS fusion constructs employed in EXAMPLES.
cpcB(30 nt) · PHLS construct used to transform *Synechocystis* to generate the Δcpc + cpcB(30 nt) · PHILS strain
Upper case italics, cpc_us and cpc_ds sequences for homologous recombination
Lower case underlined, the first 30 nucleotides of the CpcB- encoding sequence
Upper case, β-phellandrene synthase (PHLS) sequence
Lower case, chloramphenicol resistance cassette

SEQ ID NO: 1

*AAGAGTCCCTGAATATCAAAATGGTGGGATAAAAAGCTCAAAAAGGAAAGTAGGCTGTGGTTCCCTAGGC*

*AACAGTCTTCCCTACCCCACTGGAAACTAAAAAAACGAGAAAAGTTCGCACCGAACATCAATTGCATAATT*

*TTAGCCCTAAAACATAAGCTGAACGAAACTGGTTGTCTTCCCTTCCCAATCCAGGACAATCTGAGAATCCC*

*CTGCAACATTACTTAACAAAAAAGCAGGAATAAAATTAACAAGATGTAACAGACATAAGTCCCATCACCGTT*

*GTATAAAGTTAACTGTGGGATTGCAAAAGCATTCAAGCCTAGGCGCTGAGCTGTTTGAGCATCCCGGTGG*

*CCCTTGTCGCTGCCTCCGTGTTTCTCCCTGGATTTATTTAGGTAATATCTCTCATAAATCCCCGGGTAGTTA*

*ACGAAAGTTAATGGAGATCAGTAACAATAACTCTAGGGTCATTACTTTGGACTCCCTCAGTTTATCCGGGG*

*GAATTGTGTTTAAGAAAATCCCAACTCATAAAGTCAAGTAGGAGATTAATTCA*<u>atgttcgacgtattcactcgggttg</u>

<u>ttttcc</u>CATATGTGTAGTTTGCAAGTTTCTGATCCTATTCCTACCGGACGCCGTTCCGG

TGGTTATCCCCCGGCCTTATGGGATTTCGATACTATTCAATCCCTGAATACCGAAT

ATAAGGGCGAACGTCACATGCGTCGGGAAGAAGACTTAATTGGTCAAGTTCGGG

AAATGTTGGTGCACGAAGTAGAAGATCCCACTCCCCAGTTGGAATTCATTGACGA

TCTGCATAAATTGGGCATTTCCTGCCATTTTGAAAACGAGATTCTGCAAATTCTC

AAATCCATTTATCTCAACCAAAACTATAAACGGGACCTCTATTCTACCAGTTTAG

CCTTCCGTCTCTTGCGTCAATACGGGTTTATCTTGCCGCAGGAAGTTTTTGACTGC

TTTAAAAACGAAGAAGGTACGGATTTTAAACCCAGCTTCGGCCGGGATATTAAG

GGTCTGTTACAGTTGTACGAAGCCTCCTTTTTGTCCCGGAAGGGGGAAGAAACTT

TACAACTCGCCCGCGAATTTGCTACCAAAATCTTGCAAAAGGAAGTCGATGAAC

GGGAATTTGCTACTAAAATGGAATTTCCCAGTCACTGGACCGTACAAATGCCTAA

CGCTCGGCCTTTTATCGATGCCTATCGTCGGCGTCCCGACATGAACCCCGTGGTT

CTGGAACTCGCCATTCTCGATACCAATATCGTGCAAGCTCAGTTTCAAGAAGAAT

TGAAGGAGACCTCCCGTTGGTGGGAAAGCACGGGGATTGTTCAAGAACTGCCGT

TTGTTCGGGACCGGATTGTGGAAGGTTATTTTTGGACCATTGGTGTTACTCAACG

CCGTGAACACGGTTACGAACGTATTATGACGGCCAAAGTCATCGCTTTGGTGACC

TGTTTGGATGATATTTATGACGTATATGGCACTATTGAAGAATTGCAACTCTTCA

CCTCTACGATTCAGCGTTGGGATTTGGAGTCTATGAAGCAGTTACCGACTTATAT

GCAGGTAAGCTTCCTGGCCTTGCACAATTTTGTAACCGAAGTGGCCTATGATACG

CTGAAGAAAAAGGGCTACAACTCTACCCCCTATTTGCGGAAGACTTGGGTGGATT

TGGTCGAAAGTTACATTAAGGAAGCCACTTGGTACTATAATGGGTACAAACCCTC

TATGCAGGAATACCTCAACAACGCCTGGATCTCTGTGGGCAGCATGGCTATTTTG

AATCATTTGTTTTTTCGCTTTACTAATGAACGCATGCATAAGTACCGGGACATGA

ATCGTGTATCCTCTAATATTGTGCGGTTAGCCGACGATATGGGAACCTCTTTGGC

CGAAGTTGAACGCGGTGACGTGCCCAAAGCTATCCAATGTTACATGAATGAAAC

GAACGCCTCTGAGGAGGAGGCCCGCGAATATGTGCGGCGCGTTATCCAGGAAGA

ATGGGAAAAACTGAACACTGAACTGATGCGCGACGACGACGATGACGATGATTT

CACCTTAAGTAAATACTACTGCGAAGTCGTTGCTAACCTGACCCGGATGGCTCAG

-continued

```
TTCATTTACCAAGATGGTTCCGATGGGTTTGGGATGAAAGATTCCAAAGTAAATC

GTTTACTGAAAGAAACGCTGATTGAGCGCTATGAGtgaAGATCTGCGGCCGCgttgatc ggcacgtaagaggttccaactttcaccataatgaaataagatcactaccgggcgtattttttgagttatcgagattttcaggagctaagga agctaaaatggagaaaaaaatcactggatataccaccgttgatatatcccaatggcatcgtaaagaacattttgaggcatttcagtcagtt gctcaatgtacctataaccagaccgttcagctggatattacggccttttttaaagaccgtaaagaaaaataagcacaagttttatccggcctt tattcacattcttgcccgcctgatgaatgctcatccggaattccgtatggcaatgaaagacggtgagctggtgatatgggatagtgttcac ccttgttacaccgttttccatgagcaaactgaaacgttttcatcgctctggagtgaataccacgacgatttccggcagtttctacacatatat tcgcaagatgtggcgtgttacggtgaaaacctggcctatttccctaaagggtttattgagaatatgttttttcgtctcagccaatccctgggt gagtttcaccagttttgatttaaacgtggccaatatggacaacttcttcgcccccgttttcaccatgggcaaatattatacgcaaggcgaca aggtgctgatgccgctggcgattcaggttcatcatgccgtctgtgatggcttccatgtcggcagaatgcttaatgaattacaacagtactg cgatgagtggcagggcggggcgtaatttttttaaggcagttattggtgcccttaaacgcctgggGATCCGCTATTTTGTTAATTA

CTATTTGAGCTGAGTGTAAAATACCTTACTTACTCAAAAGCATTAACTAACCATAACAATGACTAATCTCTTT

TTTTGATTGAACTCCAAACTAGAATAGCCATCGAGTCAGTCCATTTAGTTCATTATTAGTGAAAGTTTGTTG

GCGGTGGGTTATCCGTTGATAAACCACCGTTTTTGTTTGGGCAAAGTAACGATTTGATGCAGTGATGGGTT

TAAAGATAATCCCGTTTGAGGAAATCCTGCAGGACGACGGGAACTTTAACCTGACCGCTGCTGGGTTCGT

AATAATTTTCTAAAATTGCCGCCATGGTGCGCCCGATCGCCAAACCGGAACCGTTGAGAGTGTGAACAAA

TTGGGTGCCTTTTTTGCCCTTTTCCTTGTAGCGAATGTTGGCCCGACGGGCTTGGAAATCGTGGAAGTTA

GAACAACTGGAAATTTCCCGGTAGGTGTTAGCCGATGGTAACCAAACTTCCAAGTCGTAGCATTTAGCCG

CTCCAAAACCTAAATCACCGGTACATAATTCCACCACTGAGCT.
```

CpcB · PHLS construct used to transform *Synechocystis* to generate the
Δcpc + cpcB · PHILS strain
Upper case italics, cpc_us and cpc_ds sequences for homologous recombination
Lower case underlined, the cpcB sequence
Upper case, β-phellandrene synthase (PHLS) sequence
Lower case, chloramphenicol resistance cassette

SEQ ID NO: 2

```
AAGAGTCCCTGAATATCAAAATGGTGGGATAAAAAGCTCAAAAAGGAAAGTAGGCTGTGGTTCCCTAGGC

AACAGTCTTCCCTACCCCACTGGAAACTAAAAAAACGAGAAAAGTTCGCACCGAACATCAATTGCATAATT

TTAGCCCTAAAACATAAGCTGAACGAAACTGGTTGTCTTCCCTTCCCAATCCAGGACAATCTGAGAATCCC

CTGCAACATTACTTAACAAAAAAGCAGGAATAAAATTAACAAGATGTAACAGACATAAGTCCCATCACCGTT

GTATAAAGTTAACTGTGGGATTGCAAAAGCATTCAAGCCTAGGCGCTGAGCTGTTTGAGCATCCCGGTGG

CCCTTGTCGCTGCCTCCGTGTTTCTCCCTGGATTTATTTAGGTAATATCTCTCATAAATCCCCGGGTAGTTA

ACGAAAGTTAATGGAGATCAGTAACAATAACTCTAGGGTCATTACTTTGGACTCCCTCAGTTTATCCGGGG

GAATTGTGTTTAAGAAAATCCCAACTCATAAAGTCAAGTAGGAGATTAATTCAatgttcgacgtattcactcgggttg tttcccaagctgatgctcgcggcgagtacctctctggttctcagttagatgctttgagcgctaccgttgctgaaggcaacaaacggattga ttctgttaaccgcatcaccggtaatgcttccgctatcgtttccaacgctgctcgtgctttgttcgccgaacagccccaattaatccaacccg gtggaaacgcctacaccagccgtcgtatggctgcttgtttgcgtgacatggaaatcatcctccgctatgttacctacgcaaccttcaccg gcgacgcttccgttctagaagatcgttgcttgaacggtctccgtgaaacctacgttgccctgggtgttcccggtgcttccgtagctgctgg cgttcaaaaaatgaaagaagctgccctggacatcgttaacgatcccatggcatcacccgtggtgattgcagtgctatcgttgctgaaat cgctggttacttcgaccgcgccgctgctgccgtagccCATATGTGTAGTTTGCAAGTTTCTGATCCTATT

CCTACCGGACGCCGTTCCGGTGGTTATCCCCCGGCCTTATGGGATTTCGATACTA

TTCAATCCCTGAATACCGAATATAAGGGCGAACGTCACATGCGTCGGGAAGAAG

ACTTAATTGGTCAAGTTCGGGAAATGTTGGTGCACGAAGTAGAAGATCCCACTCC

CCAGTTGGAATTCATTGACGATCTGCATAAATTGGGCATTTCCTGCCATTTTGAA
```

-continued

```
AACGAGATTCTGCAAATTCTCAAATCCATTTATCTCAACCAAAACTATAAACGGG

ACCTCTATTCTACCAGTTTAGCCTTCCGTCTCTTGCGTCAATACGGGTTTATCTTG

CCGCAGGAAGTTTTTGACTGCTTTAAAAACGAAGAAGGTACGGATTTTAAACCCA

GCTTCGGCCGGGATATTAAGGGTCTGTTACAGTTGTACGAAGCCTCCTTTTTGTCC

CGGAAGGGGGAAGAAACTTTACAACTCGCCCGCGAATTTGCTACCAAAATCTTG

CAAAAGGAAGTCGATGAACGGGAATTTGCTACTAAAATGGAATTTCCCAGTCAC

TGGACCGTACAAATGCCTAACGCTCGGCCTTTTATCGATGCCTATCGTCGGCGTC

CCGACATGAACCCCGTGGTTCTGGAACTCGCCATTCTCGATACCAATATCGTGCA

AGCTCAGTTTCAAGAAGAATTGAAGGAGACCTCCCGTTGGTGGGAAAGCACGGG

GATTGTTCAAGAACTGCCGTTTGTTCGGGACCGGATTGTGGAAGGTTATTTTTGG

ACCATTGGTGTTACTCAACGCCGTGAACACGGTTACGAACGTATTATGACGGCCA

AAGTCATCGCTTTGGTGACCTGTTTGGATGATATTTATGACGTATATGGCACTATT

GAAGAATTGCAACTCTTCACCTCTACGATTCAGCGTTGGGATTTGGAGTCTATGA

AGCAGTTACCGACTTATATGCAGGTAAGCTTCCTGGCCTTGCACAATTTTGTAAC

CGAAGTGGCCTATGATACGCTGAAGAAAAAGGGCTACAACTCTACCCCCTATTTG

CGGAAGACTTGGGTGGATTTGGTCGAAAGTTACATTAAGGAAGCCACTTGGTACT

ATAATGGGTACAAACCCTCTATGCAGGAATACCTCAACAACGCCTGGATCTCTGT

GGGCAGCATGGCTATTTTGAATCATTTGTTTTTTCGCTTTACTAATGAACGCATGC

ATAAGTACCGGGACATGAATCGTGTATCCTCTAATATTGTGCGGTTAGCCGACGA

TATGGGAACCTCTTTGGCCGAAGTTGAACGCGGTGACGTGCCCAAAGCTATCCAA

TGTTACATGAATGAAACGAACGCCTCTGAGGAGGAGGCCCGCGAATATGTGCGG

CGCGTTATCCAGGAAGAATGGGAAAAACTGAACACTGAACTGATGCGCGACGAC

GACGATGACGATGATTTCACCTTAAGTAAATACTACTGCGAAGTCGTTGCTAACC

TGACCCGGATGGCTCAGTTCATTTACCAAGATGGTTCCGATGGGTTTGGGATGAA

AGATTCCAAAGTAAATCGTTTACTGAAAGAAACGCTGATTGAGCGCTATGAGtgaA

GATCTGCGGCCGCgttgatcggcacgtaagaggttccaactttcaccataatgaaataagatcactaccgggcgtattttttg agttatcgagattttcaggagctaaggaagctaaaatggagaaaaaaatcactggatataccaccgttgatatatcccaatggcatcgta aagaacattttgaggcatttcagtcagttgctcaatgtacctataaccagaccgttcagctggatattacggcctttttaaagaccgtaaag aaaaataagcacaagttttatccggcctttattcacattcttgcccgcctgatgaatgctcatccggaattccgtatggcaatgaaagacg gtgagctggtgatatgggatagtgttcaccettgttacaccgttttccatgagcaaactgaaacgttttcatcgctctggagtgaataccac gacgatttccggcagtttctacacatatattcgcaagatgtggcgtgttacggtgaaaacctggcctatttccctaaagggtttattgagaa tatgttttttcgtctcagccaatccctgggtgagtttcaccagttttgatttaaacgtggccaatatggacaacttcttcgcccccgttttcacc atgggcaaatattatacgcaaggcgacaaggtgctgatgccgctggcgattcaggttcatcatgccgtctgtgatggcttccatgtcgg cagaatgcttaatgaattacaacagtactgcgatgagtggcagggcggggcgtaatttttttaaggcagttattggtgcccttaaacgcct gggGATCCGCTATTTTGTTAATTACTATTTGAGCTGAGTGTAAAATACCTTACTTACTCAA

AAGCATTAACTAACCATAACAATGACTAATCTCTTTTTTTGATTGAACTCCAAACTAGAAT

AGCCATCGAGTCAGTCCATTTAGTTCATTATTAGTGAAAGTTTGTTGGCGGTGGGTTAT

CCGTTGATAAACCACCGTTTTTGTTTGGGCAAAGTAACGATTTGATGCAGTGATGGGTT

TAAAGATAATCCCGTTTGAGGAAATCCTGCAGGACGACGGGAACTTTAACCTGACCGC

TGCTGGGTTCGTAATAATTTTCTAAAATTGCCGCCATGGTGCGCCCGATCGCCAAACC

GGAACCGTTGAGAGTGTGAACAAATTGGGTGCCTTTTTTGCCCTTTTCCTTGTAGCGAA
```

*TGTTGGCCCGACGGGCTTGGAAATCGTGGAAGTTAGAACAACTGGAAATTTCCCGGTA*

*GGTGTTAGCCGATGGTAACCAAACTTCCAAGTCGTAGCATTTAGCCGCTCCAAAACCTA*

*AATCACCGGTACATAATTCCACCACTGAGCT*

```
CpcB · PHLS construct used to transform Synechocystis to generate the
CpcB · PHLS + cpc strain
Upper case italics, cpc_us sequence for homologous recombination
Lower case underlined, the cpcB sequence
Upper case, β-phellandrene synthase (PHLS) sequence
Lower case, chloramphenicol resistance cassette
Lower case underlined italics, the cpcA sequence for homologous recombination
```
SEQ ID NO: 3

*AAGAGTCCCTGAATATCAAAATGGTGGGATAAAAAGCTCAAAAAGGAAAGTAGGCTGTGTGGTTCCCTAGGC*

*AACAGTCTTCCCTACCCCACTGGAAACTAAAAAAACGAGAAAAGTTCGCACCGAACATCAATTGCATAATT*

*TTAGCCCTAAAACATAAGCTGAACGAAACTGGTTGTCTTCCCTTCCCAATCCAGGACAATCTGAGAATCCC*

*CTGCAACATTACTTAACAAAAAAGCAGGAATAAAATTAACAAGATGTAACAGACATAAGTCCCATCACCGTT*

*GTATAAAGTTAACTGTGGGATTGCAAAAGCATTCAAGCCTAGGCGCTGAGCTGTTTGAGCATCCCGGTGG*

*CCCTTGTCGCTGCCTCCGTGTTTCTCCCTGGATTTATTTAGGTAATATCTCTCATAAATCCCCGGGTAGTTA*

*ACGAAAGTTAATGGAGATCAGTAACAATAACTCTAGGGTCATTACTTTGGACTCCCTCAGTTTATCGGGG*

*GAATTGTGTTTAAGAAAATCCCAACTCATAAAGTCAAGTAGGAGATTAATTCA*<u>atgttcgacgtattcactcgggttg</u>

<u>tttcccaagctgatgctcgcggcgagtacctctctggttctcagttagatgctttgagcgctaccgttgctgaaggcaacaaacggattga</u>

<u>ttctgttaaccgcatcaccggtaatgcttccgctatcgtttccaacgctgctcgtgctttgttcgccgaacagccccaattaatccaacccg</u>

<u>gtggaaacgcctacaccagccgtcgtatggctgcttgtttgcgtgacatggaaatcatcctccgctatgttacctacgcaaccttcaccg</u>

<u>gcgacgcttccgttctagaagatcgttgcttgaacggtctccgtgaaacctacgttgccctgggtgttcccggtgcttccgtagctgctgg</u>

<u>cgttcaaaaaatgaaagaagctgccctggacatcgttaacgatcccaatggcatcacccgtggtgattgcagtgctatcgttgctgaaat</u>

<u>cgctggttacttcgaccgcgccgctgctgccgtagcc</u>CATATGTGTAGTTTGCAAGTTTCTGATCCTATT

CCTACCGGACGCCGTTCCGGTGGTTATCCCCCGGCCTTATGGGATTTCGATACTA

TTCAATCCCTGAATACCGAATATAAGGGCGAACGTCACATGCGTCGGGAAGAAG

ACTTAATTGGTCAAGTTCGGGAAATGTTGGTGCACGAAGTAGAAGATCCCACTCC

CCAGTTGGAATTCATTGACGATCTGCATAAATTGGGCATTTCCTGCCATTTTGAA

AACGAGATTCTGCAAATTCTCAAATCCATTTATCTCAACCAAAACTATAAACGGG

ACCTCTATTCTACCAGTTTAGCCTTCCGTCTCTTGCGTCAATACGGGTTTATCTTG

CCGCAGGAAGTTTTTGACTGCTTTAAAAACGAAGAAGGTACGGATTTTAAACCCA

GCTTCGGCCGGGATATTAAGGGTCTGTTACAGTTGTACGAAGCCTCCTTTTTGTCC

CGGAAGGGGAAGAAACTTTACAACTCGCCCGCGAATTTGCTACCAAAATCTTG

CAAAAGGAAGTCGATGAACGGGAATTTGCTACTAAAATGGAATTTCCCAGTCAC

TGGACCGTACAAATGCCTAACGCTCGGCCTTTTATCGATGCCTATCGTCGGCGTC

CCGACATGAACCCCGTGGTTCTGGAACTCGCCATTCTCGATACCAATATCGTGCA

AGCTCAGTTTCAAGAAGAATTGAAGGAGACCTCCCGTTGGTGGGAAAGCACGGG

GATTGTTCAAGAACTGCCGTTTGTTCGGGACCGGATTGTGGAAGGTTATTTTTGG

ACCATTGGTGTTACTCAACGCCGTGAACACGGTTACGAACGTATTATGACGGCCA

AAGTCATCGCTTTGGTGACCTGTTTGGATGATATTTATGACGTATATGGCACTATT

GAAGAATTGCAACTCTTCACCTCTACGATTCAGCGTTGGGATTTGGAGTCTATGA

AGCAGTTACCGACTTATATGCAGGTAAGCTTCCTGGCCTTGCACAATTTTGTAAC

CGAAGTGGCCTATGATACGCTGAAGAAAAAGGGCTACAACTCTACCCCCTATTTG

-continued

```
CGGAAGACTTGGGTGGATTTGGTCGAAAGTTACATTAAGGAAGCCACTTGGTACT

ATAATGGGTACAAACCCTCTATGCAGGAATACCTCAACAACGCCTGGATCTCTGT

GGGCAGCATGGCTATTTTGAATCATTTGTTTTTTCGCTTTACTAATGAACGCATGC

ATAAGTACCGGGACATGAATCGTGTATCCTCTAATATTGTGCGGTTAGCCGACGA

TATGGGAACCTCTTTGGCCGAAGTTGAACGCGGTGACGTGCCCAAAGCTATCCAA

TGTTACATGAATGAAACGAACGCCTCTGAGGAGGAGGCCCGCGAATATGTGCGG

CGCGTTATCCAGGAAGAATGGGAAAAACTGAACACTGAACTGATGCGCGACGAC

GACGATGACGATGATTTCACCTTAAGTAAATACTACTGCGAAGTCGTTGCTAACC

TGACCCGGATGGCTCAGTTCATTTACCAAGATGGTTCCGATGGGTTTGGGATGAA

AGATTCCAAAGTAAATCGTTTACTGAAAGAAACGCTGATTGAGCGCTATGAGtgaA

GATCTGCGGCCGCgttgatcggcacgtaagaggttccaactttcaccataatgaaataagatcactaccgggcgtattttttg agttatcgagattttcaggagctaaggaagctaaaatggagaaaaaaatcactggatataccaccgttgatatatcccaatggcatcgta aagaacattttgaggcatttcagtcagttgctcaatgtacctataaccagaccgttcagctggatattacggccttttttaaagaccgtaaag aaaaataagcacaagtttatccggcctttattcacattcttgcccgcctgatgaatgctcatccggaattccgtatggcaatgaaagacg gtgagctggtgatatgggatagtgttcaccttgttacaccgttttccatgagcaaactgaaacgttttcatcgctctggagtgaataccac gacgatttccggcagtttctacacatatattcgcaagatgtggcgtgttacggtgaaaacctggcctatttccctaaagggtttattgagaa tatgttttcgtctcagccaatccctgggtgagtttcaccagttttgatttaaacgtggccaatatggacaacttcttcgccccgttttcacc atgggcaaatattatacgcaaggcgacaaggtgctgatgccgctggcgattcaggttcatcatgccgtctgtgatggcttccatgtcgg cagaatgcttaatgaattacaacagtactgcgatgagtggcagggcgggcgtaattttttttaaggcagttattggtgcccttaaacgcct gggGATCCtctggttattttaaaaaccaactttactcaggttccatacccgagaaaatccagcttaaagctgacatatctaggaa aattttcacattctaacgggagataccagaacaatgaaaaccccttaactgaagccgtttccaccgctgactctcaaggtcgctttc tgagcagcaccgaattgcaaattgctttcggtcgtctacgtcaagctaatgctggtttgcaagccgctaaagctctgaccgacaatg cccagagcttggtaaatggtgctgcccaagccgtttataacaaattcccctacaccaccaaacccaaggcaacaactttgctgcg gatcaacggggtaaagacaagtgtgcccgggacateggctactacctccgcatcgttacctactgcttagttgctggtggtaccggt cctttggatgagtacttgatcgccggtattgatgaaatcaaccgcacctttgacctctccccagctggtatgttgaagctctgaaata catcaaagctaaccacggcttgagtggcgatgcccgtgacgaagctaattcctacctcgattacgccatcaatgctctgagctag
```

NPTI · PHLS construct used to transform *Synechocystis* to generate the
Δcpc + kanR · PHLS strain
Upper case italics, cpc_us and cpc_ds sequences for homologous recombination
Upper case underlined, the kanR encoding sequence
Upper case, β-phellandrene synthase (PHLS) sequence
Lower case, chloramphenicol resistance cassette

SEQ ID NO: 4

```
AAGAGTCCCTGAATATCAAAATGGTGGGATAAAAAGCTCAAAAAGGAAAGTAGGCTGTG

GTTCCCTAGGCAACAGTCTTCCCTACCCCACTGGAAACTAAAAAAACGAGAAAAGTTCG

CACCGAACATCAATTGCATAATTTTAGCCCTAAAACATAAGCTGAACGAAACTGGTTGTC

TTCCCTTCCCAATCCAGGACAATCTGAGAATCCCCTGCAACATTACTTAACAAAAAAGC

AGGAATAAAATTAACAAGATGTAACAGACATAAGTCCCATCACCGTTGTATAAAGTTAAC

TGTGGGATTGCAAAAGCATTCAAGCCTAGGCGCTGAGCTGTTTGAGCATCCCGGTGGC

CCTTGTCGCTGCCTCCGTGTTTCTCCCTGGATTTATTTAGGTAATATCTCTCATAAATCC

CCGGGTAGTTAACGAAAGTTAATGGAGATCAGTAACAATAACTCTAGGGTCATTACTTT

GGACTCCCTCAGTTTATCCGGGGAATTGTGTTTAAGAAAATCCCAACTCATAAAGTCA

AGTAGGAGATTAATTCAATGAGTCACATCCAGAGAGAAACTAGTTGTTCCCGACCT

CGTTTGAATAGCAATATGGATGCAGATCTGTACGGATATAAATGGGCGCGAGAT
```

-continued

AACGTAGGCCAATCTGGGGCCACTATTTATCGGTTATATGGCAAACCAGATGCTC

CCGAACTGTTTCTCAAACATGGCAAAGGGTCTGTGGCCAATGATGTTACCGATGA

AATGGTGCGGTTGAACTGGTTGACAGAATTTATGCCCCTCCCGACCATCAAACAT

TTTATCAGGACTCCAGACGATGCATGGCTATTAACTACGGCCATTCCTGGGAAAA

CTGCCTTTCAGGTGTTGGAAGAATATCCCGATTCTGGTGAGAATATCGTCGATGC

GTTAGCGGTTTTTCTAAGACGTCTACATAGCATTCCCGTTTGCAATTGTCCCTTTA

ATTCGGACCGGGTGTTCCGCTTGGCGCAGGCTCAGTCCCGGATGAATAACGGTTT

GGTAGATGCCTCGGACTTTGATGATGAACGGAACGGCTGGCCCGTTGAACAGGT

TTGGAAAGAGATGCATAAGCTGCTGCCCTTCTCCCCCGACAGCGTTGTTACTCAT

GGAGATTTTTCTCTCGATAATCTGATTTTCGACGAAGGCAAGCTAATTGGCTGTA

TCGATGTGGGACGGGTAGGGATTGCGGACCGGTATCAAGACCTAGCAATTTTGT

GGAACTGCCTAGGTGAATTTTCCCCCAGCCTACAAAAACGGCTGTTTCAAAAATA

CGGAATCGATAATCCCGACATGAACAAATTACAATTTCATCTGATGCTAGATGAG

TTCTTTCATATGTGTAGTTTGCAAGTTTCTGATCCTATTCCTACCGGACGCCGTTC

CGGTGGTTATCCCCCGGCCTTATGGGATTTCGATACTATTCAATCCCTGAATACC

GAATATAAGGGCGAACGTCACATGCGTCGGGAAGAAGACTTAATTGGTCAAGTT

CGGGAAATGTTGGTGCACGAAGTAGAAGATCCCACTCCCCAGTTGGAATTCATTG

ACGATCTGCATAAATTGGGCATTTCCTGCCATTTTGAAAACGAGATTCTGCAAAT

TCTCAAATCCATTTATCTCAACCAAAACTATAAACGGGACCTCTATTCTACCAGT

TTAGCCTTCCGTCTCTTGCGTCAATACGGGTTTATCTTGCCGCAGGAAGTTTTTGA

CTGCTTTAAAAACGAAGAAGGTACGGATTTTAAACCCAGCTTCGGCCGGGATATT

AAGGGTCTGTTACAGTTGTACGAAGCCTCCTTTTTGTCCCGGAAGGGGGAAGAAA

CTTTACAACTCGCCCGCGAATTTGCTACCAAAATCTTGCAAAAGGAAGTCGATGA

ACGGGAATTTGCTACTAAAATGGAATTTCCCAGTCACTGGACCGTACAAATGCCT

AACGCTCGGCCTTTTATCGATGCCTATCGTCGGCGTCCCGACATGAACCCCGTGG

TTCTGGAACTCGCCATTCTCGATACCAATATCGTGCAAGCTCAGTTTCAAGAAGA

ATTGAAGGAGACCTCCCGTTGGTGGGAAAGCACGGGGATTGTTCAAGAACTGCC

GTTTGTTCGGGACCGGATTGTGGAAGGTTATTTTTGGACCATTGGTGTTACTCAA

CGCCGTGAACACGGTTACGAACGTATTATGACGGCCAAAGTCATCGCTTTGGTGA

CCTGTTTGGATGATATTTATGACGTATATGGCACTATTGAAGAATTGCAACTCTTC

ACCTCTACGATTCAGCGTTGGGATTTGGAGTCTATGAAGCAGTTACCGACTTATA

TGCAGGTAAGCTTCCTGGCCTTGCACAATTTTGTAACCGAAGTGGCCTATGATAC

GCTGAAGAAAAAGGGCTACAACTCTACCCCCTATTTGCGGAAGACTTGGGTGGA

TTTGGTCGAAAGTTACATTAAGGAAGCCACTTGGTACTATAATGGGTACAAACCC

TCTATGCAGGAATACCTCAACAACGCCTGGATCTCTGTGGGCAGCATGGCTATTT

TGAATCATTTGTTTTTTCGCTTTACTAATGAACGCATGCATAAGTACCGGGACAT

GAATCGTGTATCCTCTAATATTGTGCGGTTAGCCGACGATATGGGAACCTCTTTG

GCCGAAGTTGAACGCGGTGACGTGCCCAAAGCTATCCAATGTTACATGAATGAA

ACGAACGCCTCTGAGGAGGAGGCCCGCGAATATGTGCGGCGCGTTATCCAGGAA

GAATGGGAAAAACTGAACACTGAACTGATGCGCGACGACGACGATGACGATGAT

TTCACCTTAAGTAAATACTACTGCGAAGTCGTTGCTAACCTGACCCGGATGGCTC

```
AGTTCATTTACCAAGATGGTTCCGATGGGTTTGGGATGAAAGATTCCAAAGTAAA

TCGTTTACTGAAAGAAACGCTGATTGAGCGCTATGAGtgaAGATCTGCGGCCGCgtt gatcggcacgtaagaggttccaactttcaccataatgaaataagatcactaccgggcgtatttttgagttatcgagattttcaggagctaa ggaagctaaaatggagaaaaaaatcactggatataccaccgttgatatatcccaatggcatcgtaaagaacattttgaggcatttcagtc agttgctcaatgtacctataaccagaccgttcagctggatattacggccttttttaaagaccgtaaagaaaaataagcacaagttttatccg gcctttattcacattcttgcccgcctgatgaatgctcatccggaattccgtatggcaatgaaagacggtgagctggtgatatgggatagtg ttcaccttgttacaccgttttccatgagcaaactgaaacgttttcatcgctctggagtgaataccacgacgatttccggcagtttctacaca tatattcgcaagatgtggcgtgttacggtgaaaacctggcctatttccctaaagggtttattgagaatatgttttttcgtctcagccaatccctg ggtgagtttcaccagttttgatttaaacgtggccaatatggacaacttcttcgccccgttttcaccatgggcaaatattatacgcaaggcg acaaggtgctgatgccgctggcgattcaggttcatcatgccgtctgtgatggcttccatgtcggcagaatgcttaatgaattacaacagta ctgcgatgagtggcagggcggggcgtaattttttttaaggcagttattggtgcccttaaacgcctgggGATCCGCTATTTTGT

TAATTACTATTTGAGCTGAGTGTAAAATACCTTACTTACTCAAAAGCATTAACTAACCATA

ACAATGACTAATCTCTTTTTTTGATTGAACTCCAAACTAGAATAGCCATCGAGTCAGTCC

ATTTAGTTCATTATTAGTGAAAGTTTGTTGGCGGTGGGTTATCCGTTGATAAACCACCGT

TTTTGTTTGGGCAAAGTAACGATTTGATGCAGTGATGGGTTTAAAGATAATCCCGTTTGA

GGAAATCCTGCAGGACGACGGGAACTTTAACCTGACCGCTGCTGGGTTCGTAATAATT

TTCTAAAATTGCCGCCATGGTGCGCCCGATCGCCAAACCGGAACCGTTGAGAGTGTGA

ACAAATTGGGTGCCTTTTTTGCCCTTTTCCTTGTAGCGAATGTTGGCCCGACGGGCTTG

GAAATCGTGGAAGTTAGAACAACTGGAAATTTCCCGGTAGGTGTTAGCCGATGGTAAC

CAAACTTCCAAGTCGTAGCATTTAGCCGCTCCAAAACCTAAATCACCGGTACATAATTC

CACCACTGAGCT
```

The following codon-optimized isoprene synthase (ISPS) sequence was
used to replace PHLS in the CpcB · PHLS constructs, generating the Δcpc + cpcB · ISPS
and cpcB · ISPS + cpc strains

SEQ ID NO: 5

```
CATatgCCCTGGCGTGTAATCTGTGCAACTTCTTCCCAATTTACTCAAATTACCGAG

CACAATTCCCGGCGTAGTGCCAACTATCAACCCAATCTGTGGAACTTTGAGTTCT

TACAGAGCCTGGAAAATGATTTAAAGGTCGAGAAATTGGAGGAGAAGGCCACTA

AATTGGAAGAGGAAGTGCGGTGTATGATTAATCGTGTAGACACCCAACCATTGA

GTCTGTTAGAATTGATCGATGATGTGCAACGTCTCGGCCTGACATACAAATTCGA

AAAAGATATCATTAAGGCCCTAGAAAACATTGTCTTATTGGATGAAAACAAGAA

AAATAAGTCTGACTTGCATGCCACCGCTTTAAGTTTCCGCTTGTTGCGGCAGCAC

GGCTTTGAAGTGTCCCAAGATGTTTTTGAACGGTTCAAAGACAAGGAGGGCGGC

TTTTCCGGCGAACTCAAAGGGGATGTTCAGGGCCTATTGTCTTTGTATGAAGCTA

GTTACTTGGGATTTGAAGGCGAGAATCTGTTAGAAGAAGCTCGCACTTTTTCCAT

TACACATTTAAAGAACAACCTAAAGGAAGGGATTAACACAAAAGTGGCTGAGCA

GGTGTCTCATGCTCTGGAGTTGCCGTATCATCAACGCTTACACCGGCTCGAAGCC

CGCTGGTTTTTGGATAAATATGAACCGAAAGAACCGCATCATCAATTACTGCTCG

AACTGGCGAAGCTGGACTTTAATATGGTCCAAACACTACATCAGAAAGAACTCC

AGGACCTAAGTCGGTGGTGGACTGAAATGGGTCTGGCATCCAAGCTAGATTTTGT

GCGCGACCGTTTGATGGAGGTGTACTTCTGGGCACTAGGCATGGCTCCCGACCCG

CAGTTTGGTGAGTGTCGTAAGGCAGTGACCAAGATGTTTGGTTTAGTAACGATCA
```

-continued

```
TCGACGACGTTTACGATGTCTATGGCACCCTAGACGAATTACAACTCTTTACAGA

TGCCGTCGAACGTTGGGATGTTAATGCCATCAATACCTTACCTGATTACATGAAA

TTGTGCTTCCTCGCCTTGTATAATACCGTTAATGACACCAGCTATTCTATTCTGAA

GGAAAAAGGCCACAATAACTTAAGCTACCTAACCAAAAGTTGGCGGGAATTGTG

TAAGGCTTTCTTACAGGAAGCCAAATGGTCCAACAACAAAATTATCCCCGCATTT

TCTAAATACCTGGAAAATGCCTCCGTGTCCTCTTCCGGGGGCTTTGCTAGCAC

CCAGCTACTTTTCTGTTTGTCAGCAACAGGAGGACATCAGTGACCATGCCTTGCG

GTCCTTAACGGACTTTCATGGCTTAGTGCGGAGTAGCTGCGTCATTTTTCGTTTAT

GTAACGATTTGGCTACAAGTGCTGCGGAATTGGAACGTGGGGAAACAACCAACA

GCATTATCAGTTATATGCACGAAAACGATGGCACCAGTGAAGAGCAGGCACGGG

AAGAACTGCGCAAATTAATCGACGCTGAATGGAAGAAGATGAATCGCGAACGTG

TGTCTGATAGTACCTTATTACCTAAAGCCTTCATGGAAATTGCGGTGAATATGGC

CCGCGTCAGTCATTGCACTTACCAATACGGCGATGGATTAGGTCGGCCCGATTAC

GCAACGGAAAATCGGATCAAATTGCTATTGATTGATCCGTTCCCAATTAATCAAT

TAATGTACGTGtaaAGATCT
```

Codon optimized chloramphenicol resistance DNA sequence was used as
a highly-expressing leader sequence to overexpress transgenes.

SEQ ID NO: 6

```
ATGGAGAAAAAAATCACTGGATATACCACCGTTGATATATCCCAATGGCATCGT

AAAGAACATTTTGAGGCATTTCAGTCAGTTGCTCAATGTACCTATAACCAGACCG

TTCAGCTGGATATTACGGCCTTTTTAAAGACCGTAAAGAAAAATAAGCACAAGTT

TTATCCGGCCTTTATTCACATTCTTGCCCGCCTGATGAATGCTCATCCGGAATTCC

GTATGGCAATGAAAGACGGTGAGCTGGTGATATGGGATAGTGTTCACCCTTGTTA

CACCGTTTTCCATGAGCAAACTGAAACGTTTTCATCGCTCTGGAGTGAATACCAC

GACGATTTCCGGCAGTTTCTACACATATATTCGCAAGATGTGGCGTGTTACGGTG

AAAACCTGGCCTATTTCCCTAAAGGGTTTATTGAGAATATGTTTTTCGTCTCAGCC

AATCCCTGGGTGAGTTTCACCAGTTTTGATTTAAACGTGGCCAATATGGACAACT

TCTTCGCCCCCGTTTTCACCATGGGCAAATATTATACGCAAGGCGACAAGGTGCT

GATGCCGCTGGCGATTCAGGTTCATCATGCCGTCTGTGATGGCTTCCATGTCGGC

AGAATGCTTAATGAATTACAACAGTACTGCGATGAGTGGCAGGGCGGGGCGTAA
```

---

What is claimed is:

1. A cyanobacterial host cell that comprises an expression construct comprising a polynucleotide encoding a fusion protein, said fusion protein comprising (i) a protein of interest to be expressed in cyanobacteria joined to (ii) a polypeptide comprising a β-subunit of phycocyanin (cpcB) or a polypeptide comprising an α- subunit of phycocyanin (cpcA),
wherein the polynucleotide encoding said fusion protein comprises a transgene encoding the protein of interest that is codon-optimized for expression in cyanobacteria joined to the 3' end of a nucleic acid encoding the polypeptide comprising cpcB or the polypeptide comprising cpcA.

2. The cyanobacterial host cell of claim 1, wherein the transgene encodes a terpene synthase.

3. The cyanobacterial host cell of claim 2, wherein the terpene synthase is an isoprene synthase, a monoterpene synthase, or a sesquiterpene synthase.

4. The cyanobacterial host cell of claim 3, wherein the terpene synthase is an isoprene synthase.

5. The cyanobacterial host cell of claim 3, wherein the terpene synthase is a monoterpene synthase.

6. The cyanobacterial host cell of claim 5, wherein the monoterpene synthase is beta-phellandrene synthase.

7. The cyanobacterial host cell of claim 6, wherein the beta- phellandrene synthase is lavender, tomato, grand fir, pine, or spruce beta-phellandrene synthase.

8. The cyanobacterial host cell of claim 3, wherein the terpene synthase is a sesquiterpene synthase.

9. The cyanobacterial host cell of claim 8, wherein the sesquiterpene synthase is a farnesene synthase, a zingiberene synthase, a caryophellene synthase, a longifolene synthase, a taxadiene synthase, or a dictyophorine synthase.

10. The cyanobacterial host cell of claim 1, wherein the cyanobacteria host cell is a single celled cyanobacteria.

11. The cyanobacterial host cell of claim 10, where the single-celled cyanobacteria is a *Synechococcus* sp., a *Thermosynechococcus elongatus*, a *Synechocystis* sp., or a *Cyanothece* sp.

12. The cyanobacterial host cell of claim 1, wherein the cyanobacteria host cell is a micro-colonial cyanobacteria.

13. The cyanobacterial host cell of claim 12, wherein the micro-colonial cyanobacteria is a *Gloeocapsa magma, Gloeocapsa phylum, Gloeocapsa alpicola, Gloeocpasa atrata, Chroococcus* spp., or *Aphanothece* sp.

14. The cyanobacterial host cell of claim 1, wherein the cyanobacteria host cell is a filamentous cyanobacteria.

15. The cyanobacterial host cell of claim 14, wherein the filamentous cyanobacteria is an *Oscillatoria* spp., a *Nostoc* sp., an *Anabaena* sp., or an *Arthrospira* sp.

16. A cyanobacterial cell culture comprising the cyanobacterial host cell of claim 1.

17. A method of expressing a transgene at high levels, the method comprising culturing a cyanobacterial cell culture of claim 16 under conditions in which the transgene is expressed.

18. The method of claim 17, wherein the transgene encodes a terpene synthase.

19. An expression construct comprising a polynucleotide encoding a fusion protein, said fusion protein comprising a protein of interest to be expressed in cyanobacteria joined to a polypeptide comprising a β-subunit of phycocyanin (cpcB) or comprising an α-subunit of phycocyanin (cpcA), wherein the polynucleotide comprises a transgene encoding the protein of interest that is codon-optimized for expression in cyanobacteria that is joined to the 3' end of a nucleic acid encoding the cpcB or cpcA.

20. A method of modifying a cyanobacterial cell to express a transgene, the method comprising introducing an expression construct of claim 1 into the cyanobacterial cell.

* * * * *

SEQUENCE LISTING

```
Sequence total quantity: 40
SEQ ID NO: 1            moltype = DNA   length = 3584
FEATURE                 Location/Qualifiers
misc_feature            1..3584
                        note = Description of Artificial Sequence: Synthetic
                         construct
source                  1..3584
                        mol_type = other DNA
                        organism = synthetic construct
SEQUENCE: 1
aagagtccct gaatatcaaa atggtgggat aaaaagctca aaaaggaaag taggctgtgg    60
ttccctaggc aacagtcttc cctaccccac tggaaactaa aaaaacgaga aaagttcgca   120
ccgaacatca attgcataat tttagcccta aaacataagc tgaacgaaac tggttgtctt   180
cccttcccaa tccaggacaa tctgagaatc ccctgcaaca ttacttaaca aaaaagcagg   240
aataaaatta acaagatgta acagacataa gtcccatcac cgttgtataa agttaactgt   300
gggattgcaa aagcattcaa gcctaggcgc tgagctgttt gagcatcccg gtggcccttg   360
tcgctgcctc cgtgtttctc cctggattta tttaggtaat atctctcata aatccccggg   420
tagttaacga aagttaatgg agatcagtaa caataactct agggtcatta ctttggactc   480
```

```
cctcagttta tccgggggaa ttgtgtttaa gaaaatccca actcataaag tcaagtagga    540
gattaattca atgttcgacg tattcactcg ggttgtttcc catatgtgta gtttgcaagt    600
ttctgatcct attcctaccg gacgccgttc cggtggttat ccccggcct tatgggattt    660
cgatactatt caatccctga ataccgaata taagggcgaa cgtcacatgc gtcgggaaga    720
agacttaatt ggtcaagttc gggaaatgtt ggtgcacgaa gtagaagatc ccactcccca    780
gttggaattc attgacgatc tgcataaatt gggcatttcc tgccattttg aaaacgagat    840
tctgcaaatt ctcaaatcca tttatctcaa ccaaaactat aaacgggacc tctattctac    900
cagtttagcc ttccgtctct tgcgtcaata cgggtttatc ttgccgcagg aagttttga    960
ctgcttttaaa aacgaagaag gtacggattt taaacccagc ttcggccggg atattaaggg   1020
tctgttacag ttgtacgaag cctcctttt gtcccggaag ggggaagaaa ctttacaact   1080
cgcccgcgaa tttgctacca aatcttgca aaggaagtc gatgaacggg aatttgctac   1140
taaaatggaa tttcccagtc actggaccgt acaaatgcct aacgctcggc cttttatcga   1200
tgcctatcgt cggcgtcccg acatgaaccc cgtggttctg gaactcgcca ttctcgatac   1260
caatatcgtg caagctcagt ttcaagaaga atggaaggag acctcccgtt ggtgggaaag   1320
cacggggatt gttcaagaac tgccgtttgt tcgggaccgg attgtggaag gttatttttg   1380
gaccattggt gttactcaac gccgtgaaca cggttacgaa cgtattatga cggcaaagt   1440
catcgctttg gtgacctgtt tggatgatat ttatgacgta tatggcacta ttgaagaatt   1500
gcaactcttc acctctacga ttcagcgttg ggatttggag tctatgaagc agttaccgac   1560
ttatatgcag gtaagcttcc tggccttgca caatttgta accgaagtgg cctatgatac   1620
gctgaagaaa aagggctaca actctacccc ctatttgcgg aagacttggg tggatttggt   1680
cgaaagttac attaaggaag ccacttgta ctataatggg tacaaaccct ctatgcagga   1740
atacctcaac aacgctgga tctctgtggg cagcatggct attttgaatc attttgttttt   1800
tcgctttact aatgaacgca tgcataagta ccgggacatg aatcgtgtat cctctaatat   1860
tgtgcggtta gccgacgata tgggaacctc tttggccgaa gttgaacgcg gtgacgtgcc   1920
caaagctatc caatgttaca tgaatgaaac gaacgcctct gaggaggagg cccgcgaata   1980
tgtgcggcgc gttatccagg aagaatggga aaaactgaac actgaactga gtgcgacga   2040
cgacgatgac gatgatttca ccttaagtaa atactactgc gaagtcgttg ctaacctgac   2100
ccggatggct cagttcattt accaagatgg ttccgatggg tttgggatga agattccaa   2160
agtaaatcgt ttactgaaag aaacgctgat tgagcgctat gagtgaagat ctgcggccgc   2220
gttgatcggc acgtaagagg ttccaacttt caccataagt aaataagatc actaccgggc   2280
gtattttttg agttatcgag attttcagga gctaaggaag ctaaaatgga gaaaaaatc   2340
actggatata ccaccgttga tatcccaa tggcatcgta aagaacattt tgaggcattt   2400
cagtcagttg ctcaatgtac ctataaccag accgttcagc tggatattac ggcctttta   2460
aagaccgtaa agaaaaataa gcacaagttt tatcccgcct ttattcacat tcttgcccag   2520
ctgatgaatg ctcatccgga attccgtatg gcaatgaaag acggtgagct ggtgatatgg   2580
gatagtgttc acccttgtta caccgttttc catgagcaaa ctgaaacgtt tcatcgctc   2640
tggagtgaat accacgacga tttccggcag tttctacaca tatattcgca agatgtggcg   2700
tgttacggtg aaaacctggc ctatttccct aaagggttta ttgagaatat gttttttcgtc   2760
tcagccaatc cctgggtgag tttcaccagt tttgatttaa acgtggccaa tatgacaac   2820
ttcttcgccc ccgttttcac catgggcaaa tattatacgc aaggcgacaa ggtgctgatg   2880
ccgctggcga ttcaggttca tcatgccgtc tgtgatggct tccatgtcgg cagaatgctt   2940
aatgaattac aacagtactg cgatgagtgg cagggcgggg cgtaattttt ttaaggcagt   3000
tattggtgcc cttaaacgcc tgggggatccg ctattttgtt aattactatt tgactgcact   3060
gtaaatacc ttacttactc aaaagcatta actaaccata acaatgacta atctcttttt   3120
ttgattgaac tccaaactag aatagccatc gagtcagtcc atttagttca ttattagtga   3180
aagtttgttg gcggtgggtt atccgttgat aaaccaccgt ttttgtttgg gcaaagtaac   3240
gatttgatgc agtgatgggt ttaaagataa tcccgtttga ggaatctg caggacgacg   3300
ggaactttaa cctgaccgct gctgggttcg taataatttt ctaaaattgc cgccatggtg   3360
cgcccgatcg ccaaaccgga accgttgaga gtgtgaacaa attgggtgcc ttttttgccc   3420
ttttcttgt agcgaatgtt ggcccgacgg gcttggaaat cgtggaagtt agaacaactg   3480
gaaatttccc ggtaggtgtt agccgatggt aaccaaactt ccaagtcgta gcatttagcc   3540
gctccaaaac ctaaatcacc ggtacataat tccaccactg agct                    3584
SEQ ID NO: 2            moltype = DNA    length = 4070
FEATURE                 Location/Qualifiers
misc_feature            1..4070
                        note = Description of Artificial Sequence: Synthetic
                        construct
source                  1..4070
                        mol_type = other DNA
                        organism = synthetic construct
SEQUENCE: 2
aagagtccct gaatatcaaa atggtgggat aaaaagctca aaaaggaaag taggctgtgg      60
ttccctaggc aacagtcttc cctacccac tggaaactaa aaaaacgaaa aaagttcgca     120
ccgaacatca attgcataat tttagcccta aaacataagc tgaacgaaac tggttgtctt     180
cccttcccaa tccaggacaa tctgagaatc ccctgcaaca ttacttaaca aaaaagcagg    240
aataaaatta acaagatgta acagacataa gtcccatcac cgttgtataa agttaactgt    300
gggattgcaa aagcattcaa gcctaggcgc tgagctgttt gagcatcccg gtggcccttg    360
tcgctgcctc cgtgtttctc cctggattta tttaggtaat atctctcata aatccccgga    420
tagttaacga aagttaatgg agatcagtaa caataactct agggtcatta ctttggactc    480
cctcagttta tccgggggaa ttgtgtttaa gaaaatccca actcataaag tcaagtagga    540
gattaattca atgttcgacg tattcactcg ggttgtttcc caagctgatg ctcgcggcga    600
gtacctctct ggttctcagt tagatgcttt gagcgctacc gttgctgaag caacaaacg      660
gattgattct gttaaccgca tcaccggtaa tgcttccgt atcgtttcca acgctgtcg      720
tgctttgttc gccgaacagc cccaattaat ccaacccgtt ggaaacgcct acaccagccg    780
tcgtatgggct gcttgttttgc gtgacatgga aatcatcctc cgctatgtta cctacgcaac   840
cttcaccggc gacgcttccg ttctagaaga tcgttgcttg aacggtctcc gtgaaaccta    900
cgttgccctg ggtgttcccg gtgcttccgt agctgctggc gttcaaaaaa tgaaagaagc    960
tgccctggac atcgttaacg atcccaatgg catcaccgtt ggtgattgca gtgctatcgt   1020
```

```
tgctgaaatc gctggttact tcgaccgcgc cgctgctgcc gtagcccata tgtgtagttt    1080
gcaagtttct gatcctattc ctaccggacg ccgttccggt ggttatcccc cggccttatg    1140
ggatttcgat actattcaat ccctgaatac cgaatataag ggcgaacgtc acatgcgtcg    1200
ggaagaagac ttaattggtc aagttcggga atgttggtg cacgaagtag aagatcccac     1260
tcccagttg gaattcattg acgatctgca taaattgggc atttcctgcc attttgaaaa     1320
cgagattctg caaattctca aatccatttta tctcaaccaa aactataaac gggacctcta   1380
ttctaccagt ttagccttcc gtccttgcg tcaatacggg tttatcttgc cgcaggaagt     1440
ttttgactgc tttaaaaacg aagaaggtac ggattttaaa cccagcttcg gccgggatat    1500
taagggtctg ttacagttgt acgaagcctc cttttttgtcc cggaaggggg aagaaacttt   1560
acaactcgcc cgcgaattg ctaccaaaat cttgcaaaag gaagtcgatg aacgggaatt     1620
tgctactaaa atggaatttc ccagtcactg gaccgtacaa atgcctaacg ctcggccttt    1680
tatcgatgcc tatcgtcggc gtcccgacat gaacccgtg gttctggaac tcgccattct     1740
cgataccaat atcgtgcaag ctcagtttca agaagaattg aaggagacct cccgttggtg    1800
ggaaagcacg gggattgttc aagaactgcc gtttgttcgg gaccggattg tggaaggtta    1860
tttttggacc attggtgtta ctcaacgccg tgaacacggt tacgaacgta ttatgacggc    1920
caaagtcatc gctttggtga cctgtttgga tgatatttat gacgtatatg gcactattga    1980
agaattgcaa ctcttcacct ctacgattca gcgttgggat ttggagtcta tgaagcagtt    2040
accgacttat atgcaggtaa gcttcctggc cttgcacaat tttgtaaccg aagtggccta    2100
tgatacgctg aagaaaaagg gctacaactc taccccctat ttgcggaaga cttgggtgga   2160
tttggtcgaa agttacatta aggaagccac ttggtactat aatgggtaca aaccctctat    2220
gcaggaatac ctcaacaacg cctggatctc tgtgggcagc atggctattt tgaatcattt    2280
gttttttcgc tttactaatg aacgcatgca taagtaccgg gacatgaatc gtgtatcctc   2340
taatattgtg cggttagccg acgatatggg aacctctttg gccgaagttg aacgcggtga   2400
cgtgcccaaa gctatccaat gttacatgaa tgaaacgaac gcctctgagg aggaggcccg    2460
cgaatatgtg cggcgcgtta tccaggaaga atgggaaaaa ctgaacactg aactgatgcg   2520
cgacgacgac gatgacgatg atttcaacctt aagtaaatac tactgcgaag tcgttgctaa   2580
cctgacccgg atggctcagt tcatttacca agatggttcc gatgggtttg ggatgaaaga   2640
ttccaaagta aatcgtttac tgaaagaaac gctgattgag cgctatgagt gaagatctgc   2700
ggccgcgttg atcggcacgt aagaggttcc aactttcacc ataatgaaat aagatcacta    2760
ccgggcgtat tttttgagtt atcgagattt tcaggagcta aggaagctaa aatggagaaa    2820
aaaatcactg gatataccac cgttgatata tcccaatggc atcgtaaaga acattttgag    2880
gcatttcagt cagttgctca atgtacctat aaccagaccg ttcagctgga tattacggcc    2940
tttttaaaga ccgtaaagaa aaataagcac aagttttatc cggcctttat tcacattctt    3000
gcccgcctga tgaatgctca tccggaattc cgtatgcaa tgaaagacgg tgagctggtg    3060
atatgggata gtgttcaccc ttgttacacc gttttccatg agcaaactga aacgttttca    3120
tcgctctgga gtgaatacca cgacgatttc cggcagtttc tacacatata ttcgcaagat   3180
gtggcgtgtt acggtgaaaa cctggcctat ttccctaaag ggtttattga gaatatgttt    3240
ttcgtctcag ccaatccctg ggtgagtttc accagtttg atttaaacgt ggccaatatg    3300
gacaacttct tcgccccgt tttcaccatg ggcaaatatt atacgcaagg cgacaaggtg    3360
ctgatgccgc tggcgattca ggttcatcat gccgtctgtg atgcttcca tgtcggcaga    3420
atgcttaatg aattacaaca gtactgcgat gagtggcagg gcggggcgta atttttttaa    3480
ggcagttatt ggtgccctta aacgcctggg gatccgctat tttgttaatt actatttgag    3540
ctgagtgtaa aattaacttac ttactcaaaa gcattaacta accataacaa tgactaatct    3600
ctttttttga ttgaactcca aactagaata gccatcgagt cagtccattt agttcattat    3660
tagtgaaagt ttgttggcgg tgggttatcc gttgataaac caccgttttt gtttgggcaa   3720
agtaacgatt tgatgcagtg atgggtttaa agataatccc gtttgaggaa atcctgcagg    3780
acgacgggaa ctttaacctg accgctgctg ggttcgtaat aatttttctaa aattgccgcc    3840
atggtgcgcc cgatcgccaa accggaaccg ttgagagtgt gaacaaattg ggtgcctttt    3900
ttgccccttt ccttgtagcg aatgttggcc cgacgggctt ggaaatcgtg gaagttagaa    3960
caactggaaa tttcccggta ggtgttagcc gatggtaacc aaacttccaa gtcgtagcat    4020
ttagccgctc caaaacctaa atcaccggta cataattcca ccactgagct               4070
```

SEQ ID NO: 3          moltype = DNA   length = 4114
FEATURE               Location/Qualifiers
misc_feature          1..4114
                      note = Description of Artificial Sequence: Synthetic
                      construct
source                1..4114
                      mol_type = other DNA
                      organism = synthetic construct
SEQUENCE: 3

```
aagagtccct gaatatcaaa atggtgggat aaaaagctca aaaaggaaag taggctgtgg    60
ttccctaggc aacagtcttc cctaccccac tggaaactaa aaaaacgaga aaagttcgca   120
ccgaacatca attgcataat tttagcccta aaacataagc tgaacgaaac tggttgtctt    180
cccttcccaa tccaggacaa tctgagaatc ccctgcaaca ttacttaaca aaaaagcagg    240
aataaaatta acaagatgta acagacataa gtcccatcac cgttgtataa agttaactgt    300
gggattgcaa aagcattcaa gcctaggcgc tgagctgttt gagcatcccg gtgggccttg    360
tcgctgcctc cgtgtttctc cctggattta tttaggtaat atctctcata aatccccggg    420
tagttaacga aagttaatgg agatcagtaa caataactat agggtcatta ctttggactc    480
cctcagttta tccgggggaa ttgtgtttaa gaaaatccca actcataaag tcaagtagga    540
gattaattca atgttcgacg tattcactcg ggttgtttcc caagctgatg ctcgcggcga    600
gtacctctct ggttctcagt tagatgcttt gagcgctacc gttgctgaag gcaacaaacg    660
gattgattct gttaaccgca tcaccggtaa tgcttccgct atcgtttcca acgctgctcg    720
tgcttttgttc gccgaacagc cccaattaat ccaacccgt ggaaacgcct acaccagccg    780
tcgtatggct gcttgtttgc gtgacatgga aatcatcctc cgctatgtta cctacgcaac    840
cttcaccggc gacgcttccg ttctagaaga tcgttgcttg aacggtctcc gtgaaaccta    900
cgttgccctg ggtgttccg gtgcttccgt agctgctggc gttcaaaaaa tgaaagaagc    960
tgcccctgga atcgttaacg atcccaatgg catcacccgt ggtgattgca gtgctatcgt    1020
tgctgaaatc gctggttact tcgaccgcgc cgctgctgcc gtagcccata tgtgtagttt    1080
```

```
gcaagtttct gatcctattc ctaccggacg ccgttccggt ggttatcccc cggccttatg   1140
ggatttcgat actattcaat ccctgaatac cgaatataag ggcgaacgtc acatgcgtcg   1200
ggaagaagac ttaattggtc aagttcggga aatgttggtg cacgaagtag aagatcccac   1260
tccccagttg gaattcattg acgatctgca taaattgggc atttcctgcc attttgaaaa   1320
cgagattctg caaattctca aatccattta tctcaaccaa aactataaac gggacctcta   1380
ttctaccagt ttagccttcc gtctcttgcg tcaatacggg tttatcttgc cgcaggaagt   1440
ttttgactgc tttaaaaacg aagaaggtac ggattttaaa cccagcttcg gccgggatat   1500
taagggtctg ttacagttgt acgaagcctc cttttttgtcc cggaagggg aagaaacttt   1560
acaactcgcc cgcgaatttg ctaccaaaat cttgcaaaag gaagtcgatg aacggaatt   1620
tgctactaaa atggaatttc ccagtcactg gaccgtacaa atgcctaacg ctcggcctt   1680
tatcgatgcc tatcgtcggc gtcccgacat gaaccccgtg gttctggaac tcgccattct   1740
cgataccaat atcgtgcaag ctcagtttca agaagaattg aaggagacct cccgttggtg   1800
ggaaagcacg gggattgttc aagaactgcc gtttgttcgg gaccggattg tggaaggtta   1860
tttttggacc attggtgtta ctcaacgccg tgaacacgta tacgaacgta ttatgacggc   1920
caaagtcatc gctttggtga cctgtttgga tgatatttat gacgtatatg gcactattga   1980
agaattgcaa ctcttcacct ctacgattca gcgttgggat ttggagtcta tgaagcagtt   2040
accgacttat atgcaggtaa gcttcctggc cttgcacaat tttgtaaccg aagtggccta   2100
tgatacgctg aagaaaaagg gctacaactc tacccctat ttgcggaaga cttgggtgga   2160
tttggtcgaa agttacatta aggaagccac ttggtactat aatgggtaca aaccctctat   2220
gcaggaatac ctcaacaacg cctggatctc tgtgggcagc atggctattt tgaatcattt   2280
gttttttcgc tttactaatg aacgcatgca taagtaccgg acatgaatc gtgtatcctc   2340
taatattgtg cggttagccg acgatatggg aacctctttg gccgaagttg aacgcggtga   2400
cgtgcccaaa gctatccaat gttacatgaa tgaaacgaac gcctctgagg aggaggccca   2460
cgaatatgtg cggcgcgtta tccaggaaga atgggaaaaa ctgaacactg aactgatgcg   2520
cgacgacgac gatgacgatg atttcacctt aagtaaatac tactgcgaag tcgttgctaa   2580
cctgacccgg atggctcagt tcatttacca agatggttcc gatgggtttg ggatgaaaga   2640
ttccaaagta aatcgtttac tgaaagaaac gctgattgag cgctatgagt gaagatctgc   2700
ggccgcgttg atcggcacgt aagaggttcc aactttcacc ataatgaaat aagatcacta   2760
ccgggcgtat tttttgagtt atcgagattt tcaggagcta aggaagctaa aatggagaaa   2820
aaaatcactg gatataccac cgttgatata tcccaatggc atcgtaaaga acattttgag   2880
gcatttcagt cagttgctca atgtaccatt aaccagaccg ttcagctgga tattacggcc   2940
ttttttaaaga ccgtaaagaa aaataagcac aagttttatc cggcctttat tcacattctt   3000
gcccgcctga tgaatgctca tccggaattc cgtatggcaa tgaaagacgg tgagctggtg   3060
atatgggata gtgttcaccc ttgttacacc gttttccatg agcaaactga aacgttttca   3120
tcgctctgga gtgaatacca cgacgatttc cggcagtttc tacacatata ttcgcaagat   3180
gtggcgtgtt acggtgaaaa cctggcctat ttccctaaag ggtttattga gaatatgttt   3240
ttcgtctcag ccaatccctg ggtgagtttc accagttttg atttaaacgt ggccaatatg   3300
gacaacttct tcgcccccgt tttcaccatg gcaaatatt atacgcaagg cgacaaggtg   3360
ctgatgccgc tggcgattca ggttcatcat gccgtctgtg atggcttcca tgtcggcaga   3420
atgcttaatg aattacaaca gtactgcgat gagtggcagg gcggggcgta atttttttaa   3480
ggcagttatt ggtgcccta aacgcctggg gatcctctgg ttatttttaaa aaccaacttt   3540
actcaggttc cataccccgag aaaatccagc ttaaagctga catatctagg aaaattttca   3600
cattctaacg ggagatacca gaacaatgaa aacccctta actgaagccg tttccaccgc   3660
tgactctcaa ggtcgctttc tgagcagcac cgaattgcaa attgctttcg gtcgtctacg   3720
tcaagctaat gctggtttgc aagccgctaa agctctgacc gacaatgccc agagcttggt   3780
aaatggtgct gcccaagccg tttataacaa attcccctac accacccaaa cccaaggcaa   3840
caacttttgct gcggatcaac ggggtaaaga caagtgtgcc gggacatcg gctactacct   3900
ccgcatcgtt acctactgct tagttgctgg tggtaccggt cctttggatg agtacttgat   3960
cgccggtatt gatgaaatca accgcacctt tgacctctcc cccagctggt atgttgaagc   4020
tctgaaatac atcaaagcta accacggctt gagtggcgat gcccgtgacg aagctaattc   4080
ctacctcgat tacgccatca atgctctgag ctag                              4114

SEQ ID NO: 4              moltype = DNA   length = 4367
FEATURE                   Location/Qualifiers
misc_feature              1..4367
                          note = Description of Artificial Sequence: Synthetic
                           construct
source                    1..4367
                          mol_type = other DNA
                          organism = synthetic construct
SEQUENCE: 4
aagagtccct gaatatcaaa atggtgggat aaaaagctca aaaaggaaag taggctgtgg    60
ttccctaggc aacagtcttc cctaccccac tggaaactaa aaaaacgaga aaagttcgca   120
ccgaacatca attgcataat tttagcccta aaacataagc tgaacgaaac tggttgtctt   180
cccttcccaa tccaggacaa tctgagaatc ccctgcaaca ttacttaaca aaaaagcagg   240
aataaaatta acaagatgta acagacataa gtcccatcac cgttgtataa agttaactgt   300
gggattgcaa aagcattcaa gcctaggcgc tgagctgttt gagcatcccg gtggcccttg   360
tcgctgcctc cgtgtttctc cctggattta tttaggtaat atctctcata aatcccccggg   420
tagttaacga aagttaatgg agatcagtaa caataactct agggtcatta ctttggactc   480
cctcagttta tccggggaa ttgtgtttaa gaaaatccca actcataaag tcaagtagga   540
gattaattca atgagtcaca tccagagaga aactagttgt tcccgacctc gtttgaatag   600
caatatggat gcagatctgt acggatataa atgggcgcga gataacgtag ccaatctgg   660
ggccactatt tatcggttat atggcaaacc agatgctccc gaactgtttc tcaaacatgg   720
caaagggtct gtggcaatg atgttaccga tgaaatggtt cggttgaact ggttgacaga   780
atttatgccc ctcccgacca tcaaacattt tatcaggact ccagacgatg catggctatt   840
aactacggcc attcctggga aaactgcctt tcaggtgttg aagaatatc ccgattctgt   900
tgagaatatc gtcgatgcgt tagcggtttt tctaagacgt ctacatagca ttcccgtttg   960
caattgtccc tttaattcgg accgggtgtt ccgcttggcg caggctcagt cccggatgaa  1020
taacggtttg gtagatgcct cggactttga tgatgaacgg aacggctggc ccgttgaaca  1080
```

```
ggtttggaaa gagatgcata agctgctgcc cttctccccc gacagcgttg ttactcatgg   1140
agattttttct ctcgataatc tgattttcga cgaaggcaag ctaattggct gtatcgatgt  1200
gggacgggta gggattgcgg accggtatca agacctagca attttgtgga actgcctagg  1260
tgaatttttcc cccagcctac aaaaacggct gtttcaaaaa tacggaatcg ataatcccga  1320
catgaacaaa ttacaatttc atctgatgct agatgagttc tttcatatgt gtagtttgca  1380
agtttctgat cctattccta ccggacgccg ttccggtggt tatccccccgg ccttatggga  1440
tttcgatact attcaatccc tgaataccga atataagggc gaacgtcaca tgcgtcggga  1500
agaagactta attggtcaag ttcgggaaat gttggtgcac gaagtagaag atcccactcc  1560
ccagttggaa ttcattgacg atctgcataa atgggcatt tcctgccatt ttgaaaacga  1620
gattctgcaa attctcaaat ccatttatct caaccaaaac tataaacggg acctctattc  1680
taccagttta gccttccgtc tcttgcgtca atacgggttt atcttgccgc aggaagtttt  1740
tgactgcttt aaaaacgaag aaggtacgga ttttaaaccc agcttcggcc gggatattaa  1800
gggtctgtta cagttgtacg aagcctcctt tttgtcccgg aagggggaag aaactttaca  1860
actcgcccgc gaatttgcta ccaaaatctt gcaaaaggaa gtcgatgaac gggaatttgc  1920
tactaaaatg gaatttccca gtcactggac cgtacaaatg cctaacgctc ggcctttat   1980
cgatgcctat cgtcggcgtc ccgacatgaa ccccgtggtt ctggaactcg ccattctcga  2040
taccaatatc gtgcaagctc agtttcaaga agaattgaag gagacctccc gttggtggga  2100
aagcacgggg attgttcaag aactgccgtt tgttcggagc cggattgtgg aaggttattt  2160
ttggaccatt ggtgttactc aacgccgtga acacgttac gaacgtatta tgacggccaa  2220
agtcatcgct ttggtgacct gttttggatga tatttatgac gtatatggca ctattgaaga  2280
attgcaactc ttcacctcta cgattcagcg ttgggatttg gagtctatga agcagttacc  2340
gacttatatg caggtaagct tcctggcctt gcacaattat gtaaccgaag tggcctatga  2400
tacgctgaag aaaaagggct acaactctac ccctatttg cggaagactt gggtggattt  2460
ggtcgaaagt tacattaagg aagccacttg gtactataat gggtacaaac cctctatgca  2520
ggaataccte aacaacgcct ggatctctgt gggcagcatg gctattttga atcatttgtt  2580
ttttcgcttt actaatgaac gcatgcataa gtaccgggac atgaatcgtg tatcctctaa  2640
tattgtgcgg ttagccgacg atatgggaac ctctttggcc gaagttgaac gcggtgacgt  2700
gcccaaagct atccaatgtt acatgaatga acgaacgcc tctgaggagg aggcccgcga  2760
atatgtgcgg cgcgttatcc aggaagaatg ggaaaaactg aacactgaac tgatgcgcga  2820
cgacgacgat gacgatgatt tcaccttaag taaatactac tgcgaagtcg ttgctaacct  2880
gacccggatg gctcagttca tttaccaaga tggttccgat gggtttggga tgaaagattc  2940
caaagtaaat cgtttactga aagaaacgct gattgagcgc tatgagtgaa gatctgcggc  3000
cgcgttgatc ggcacgtaag aggttccaac tttcaccata atgaaataag atcactaccg  3060
ggcgtatttt ttgagttatc gagattttca ggagctaagg aagctaaaat gggagaaaaa  3120
atcactggat ataccaccgt tgatatatcc caatggcatc gtaaagaaca ttttgaggca  3180
tttcagtcag ttgctcaatg tacctataac cagaccgttc agctggatat acggcctttt  3240
ttaaagaccg taaagaaaaa taagcacaag ttttatccgg cctttattca cattcttgcc  3300
cgcctgatga atgctcatcc ggaattccgt atggcaatga aagacggtga gctggtgata  3360
tgggatagtg ttcacccttg ttacaccgtt tccatgagca aactgaaacg ttttcatcg   3420
ctctggagtg aataccacga cgatttccgg cagtttctac acatatattc gcaagatgtg  3480
gcgtgttacg gtgaaaacct ggcctatttc cctaaagggt ttattgagaa tatgtttttc  3540
gtctcagcca atccctgggt gagtttcacc agttttgatt taaacgtggc caatatggac  3600
aacttcttcg ccccgttttt caccatgggc aaatattata cgcaaggcga caaggtgctg  3660
atgccgctgg cgattcaggt tcatcatgcc gtctgtgatg gcttccatgt cggcagaatg  3720
cttaatgaat tacaacagta ctgcgatgag tggcagggcg gggcgtaatt tttttaaggc  3780
agttattggt gcccttaaac gcctgggat ccgctatttt gttaattact atttgagctg   3840
agtgtaaaat accttacta ctcaaaagca ttaactaacc ataacaatct ctctt          3900
ttttgattg aactcaaac tagaatagcc atcgagtcag tccatttagt tcattattag     3960
tgaaagtttg ttggcggtgg gttatccgtt gataaaccac cgtttttgtt tgggcaaagt   4020
aacgatttga tgcagtgatg ggtttaaaga taatcccgtt tgaggaaatc ctgcaggacg   4080
acgggacttt aacctgacc gctgctgggt tcgtaataat tttctaaact tgccgccatg   4140
gtgcgcccga tcgccaaacc ggaaccgttg agagtgtgaa caaattgggg gccttttttg   4200
ccctttttcct tgtagcgaat gttggcccga cgggcttgga aatcgtggaa gttagaacaa   4260
ctggaaatt cccggtaggt gttagccgat ggtaaccaaa cttccaagtc gtagcattta    4320
gccgctccaa aacctaaatc accggtacat aattccacca ctgagct                 4367
```

```
SEQ ID NO: 5              moltype = DNA    length = 1719
FEATURE                   Location/Qualifiers
misc_feature              1..1719
                          note = Description of Artificial Sequence: Synthetic
                          construct
source                    1..1719
                          mol_type = other DNA
                          organism = synthetic construct
SEQUENCE: 5
catatgccct ggcgtgtaat ctgtgcaact tcttcccaat ttactcaaat taccgagcac     60
aattcccggc gtagtgccaa ctatcaaccc aatctgtgga actttgagtt cttacagagc   120
ctggaaaatg atttaaaggt cgagaaattg gaggagaagg ccactcaatt ggaagaggaa   180
gtgcggtgta tgattaatcg tgtagacacc caaccattga gtctgttaga attgatcgat   240
gatgtgcaac gtctcggcct gacatacaaa ttcgaaaaag atatcattaa ggccctagaa   300
aacattgtct tattggatga aaacaagaaa ataagtctg acttgcatgc caccgcttta    360
agtttccgct gttgcggca gcacggcttt gaagtgtccc aagatgtttt tgaacggttc   420
aaagacaagg agggcggctt ttccggcgaa ctcaaagggg atgttcaggg cctattgtct   480
ttgtatgaag ctagttactt gggatttgaa gcgagaatc tgttagaaga agctcgcact   540
tttttccatta cacatttaaa gaacaaccta aggaagggaa ttaacacaaa agtggctgag   600
caggtgtctc atgctctgga gttgccgtat catcaacgct acaccggct cgaagcccgc    660
tggttttttgg ataaatatga accgaaagaa ccgcatcatc aattactgct cgaactggcg   720
aagctggact ttaatatggt ccaaacacta catcagaaag aactccagga cctaagtcgg   780
tggtggactg aaatgggtct ggcatccaag ctagattttg tgcgcgaccg tttgatggag   840
```

```
gtgtacttct gggcactagg catggctccc gacccgcagt ttggtgagtg tcgtaaggca    900
gtgaccaaga tgtttggttt agtaacgatc atcgacgacg tttacgatgt ctatggcacc    960
ctagacgaat tacaactctt tacagatgcc gtcgaacgtt gggatgttaa tgccatcaat   1020
accttacctg attacatgaa attgtgcttc ctcgccttgt ataataccgt taatgacacc   1080
agctattcta ttctgaagga aaaaggccac aataacttaa gctacctaac caaaagttgg   1140
cgggaattgt gtaaggcttt cttacaggaa gccaaatggt ccaacaacaa aattatcccc   1200
gcattttcta ataacctgga aaatgcctcc gtgtcctctt ccggggtggc tttgctagca   1260
cccagctact tttctgtttg tcagcaacag gaggacatca gtgaccatgc cttgcggtcc   1320
ttaacggact ttcatggctt agtgcggagt agctgcgtca ttttcgtttt atgtaacgat   1380
ttggctacaa gtgctgcgga attgaacgt ggggaaacaa ccaacagcat tatcagttat   1440
atgcacgaaa acgatggcac cagtgaagag caggcacggg aagaactgcg caaattaatc   1500
gacgctgaat ggaagaagat gaatcgcgaa cgtgtgtctg atagtacctt attacctaaa   1560
gccttcatgg aaaattgcgg t gaatatggcc cgcgtcagtc attgcactta ccaatacggc   1620
gatggattag gtcggcccga ttacgcaacg gaaaatcgga tcaaattgct attgattgat   1680
ccgttcccaa ttaatcaatt aatgtacgtg taaagatct                          1719

SEQ ID NO: 6           moltype = DNA   length = 660
FEATURE                Location/Qualifiers
misc_feature           1..660
                       note = Description of Artificial Sequence: Synthetic
                        construct
source                 1..660
                       mol_type = other DNA
                       organism = synthetic construct
SEQUENCE: 6
atggagaaaa aaatcactgg atataccacc gttgatatat cccaatggca tcgtaaagaa    60
cattttgagg catttcagtc agttgctcaa tgtacctata accagaccgt tcagctggat   120
attacggcct ttttaaagac cgtaaagaaa aataagcaca gtttttatcc ggcctttatt   180
cacattcttg cccgcctgat gaatgctcat ccggaattcc gtatggcaat gaaagacggt   240
gagctggtga tatgggatag tgttcaccct tgttacaccg ttttccatga gcaaactgaa   300
acgttttcat cgctctggag tgaataccac gacgatttcc ggcagtttct acacatatat   360
tcgcaagatg tggcgtgtta cggtgaaaac ctggcctatt tccctaaagg gtttattgag   420
aatatgtttt tcgtctcagc caatccctgg gtgagtttca ccagttttga tttaaacgtg   480
gccaatatgg acaacttctt cgccccccgtt ttcaccatgg gcaaatatta tacgcaaggc   540
gacaaggtgc tgatgccgct ggcgattcag gttcatcatg ccgtctgtga tggcttccat   600
gtcggcagaa tgcttaatga attacaacag tactgcaggg cggggcgtaa                660

SEQ ID NO: 7           moltype = DNA   length = 35
FEATURE                Location/Qualifiers
misc_feature           1..35
                       note = Description of Artificial Sequence: Synthetic primer
source                 1..35
                       mol_type = other DNA
                       organism = synthetic construct
SEQUENCE: 7
ccgctcgaga agagtccctg aatatcaaaa tggtg                              35

SEQ ID NO: 8           moltype = DNA   length = 38
FEATURE                Location/Qualifiers
misc_feature           1..38
                       note = Description of Artificial Sequence: Synthetic primer
source                 1..38
                       mol_type = other DNA
                       organism = synthetic construct
SEQUENCE: 8
ggaattccat atgggaaaca acccgagtga atacgtcg                           38

SEQ ID NO: 9           moltype = DNA   length = 35
FEATURE                Location/Qualifiers
misc_feature           1..35
                       note = Description of Artificial Sequence: Synthetic primer
source                 1..35
                       mol_type = other DNA
                       organism = synthetic construct
SEQUENCE: 9
ggaattccat atgggctacg gcagcagcgg cgcgg                              35

SEQ ID NO: 10          moltype = DNA   length = 36
FEATURE                Location/Qualifiers
misc_feature           1..36
                       note = Description of Artificial Sequence: Synthetic primer
source                 1..36
                       mol_type = other DNA
                       organism = synthetic construct
SEQUENCE: 10
cgcggatcct ctggttattt taaaaaccaa ctttac                             36

SEQ ID NO: 11          moltype = DNA   length = 31
FEATURE                Location/Qualifiers
```

```
misc_feature              1..31
                          note = Description of Artificial Sequence: Synthetic primer
source                    1..31
                          mol_type = other DNA
                          organism = synthetic construct
SEQUENCE: 11
cgcgagctcc tagctcagag cattgatggc g                                       31

SEQ ID NO: 12             moltype = DNA  length = 34
FEATURE                   Location/Qualifiers
misc_feature              1..34
                          note = Description of Artificial Sequence: Synthetic primer
source                    1..34
                          mol_type = other DNA
                          organism = synthetic construct
SEQUENCE: 12
cgcggatcct cagtttttaa ttctagctgg cctg                                    34

SEQ ID NO: 13             moltype = DNA  length = 36
FEATURE                   Location/Qualifiers
misc_feature              1..36
                          note = Description of Artificial Sequence: Synthetic primer
source                    1..36
                          mol_type = other DNA
                          organism = synthetic construct
SEQUENCE: 13
cgcgagctcc ctgattctag gcaagggaaa tcattg                                  36

SEQ ID NO: 14             moltype = DNA  length = 37
FEATURE                   Location/Qualifiers
misc_feature              1..37
                          note = Description of Artificial Sequence: Synthetic primer
source                    1..37
                          mol_type = other DNA
                          organism = synthetic construct
SEQUENCE: 14
ggaattccat atgaaagaac tcatctagca tcagatg                                 37

SEQ ID NO: 15             moltype = DNA  length = 36
FEATURE                   Location/Qualifiers
misc_feature              1..36
                          note = Description of Artificial Sequence: Synthetic primer
source                    1..36
                          mol_type = other DNA
                          organism = synthetic construct
SEQUENCE: 15
ggaattccat atgccctggc gtgtaatctg tgcaac                                  36

SEQ ID NO: 16             moltype = DNA  length = 35
FEATURE                   Location/Qualifiers
misc_feature              1..35
                          note = Description of Artificial Sequence: Synthetic primer
source                    1..35
                          mol_type = other DNA
                          organism = synthetic construct
SEQUENCE: 16
ggaagatctt tacacgtaca ttaattgatt aattg                                   35

SEQ ID NO: 17             moltype = DNA  length = 24
FEATURE                   Location/Qualifiers
misc_feature              1..24
                          note = Description of Artificial Sequence: Synthetic primer
source                    1..24
                          mol_type = other DNA
                          organism = synthetic construct
SEQUENCE: 17
ccattagcaa ggcaaatcaa agac                                               24

SEQ ID NO: 18             moltype = DNA  length = 23
FEATURE                   Location/Qualifiers
misc_feature              1..23
                          note = Description of Artificial Sequence: Synthetic primer
source                    1..23
                          mol_type = other DNA
                          organism = synthetic construct
SEQUENCE: 18
ggtggaaacg gcttcagtta aag                                                23

SEQ ID NO: 19             moltype = DNA  length = 27
```

```
FEATURE                 Location/Qualifiers
misc_feature            1..27
                        note = Description of Artificial Sequence: Synthetic primer
source                  1..27
                        mol_type = other DNA
                        organism = synthetic construct
SEQUENCE: 19
cctgattcta ggcaagggaa atcattg                                          27

SEQ ID NO: 20           moltype = DNA  length = 24
FEATURE                 Location/Qualifiers
misc_feature            1..24
                        note = Description of Artificial Sequence: Synthetic primer
source                  1..24
                        mol_type = other DNA
                        organism = synthetic construct
SEQUENCE: 20
gttccctttg gtcaagcaag taag                                             24

SEQ ID NO: 21           moltype = DNA  length = 30
FEATURE                 Location/Qualifiers
misc_feature            1..30
                        note = Description of Artificial Sequence: Synthetic primer
source                  1..30
                        mol_type = other DNA
                        organism = synthetic construct
SEQUENCE: 21
ggttgattcg tttacatcag ttcaataaag                                       30

SEQ ID NO: 22           moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 22
caatccggtc ccgaacaaac                                                  20

SEQ ID NO: 23           moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 23
caccggtaat gcttccgcta                                                  20

SEQ ID NO: 24           moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 24
gcatgtgacg ttcgcccttt                                                  20

SEQ ID NO: 25           moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 25
ccgcatcgtt acctactgct                                                  20

SEQ ID NO: 26           moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 26
gatcactggt agcgtagccc                                                  20
```

```
SEQ ID NO: 27            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 27
gctaacagtg accgttccca                                                   20

SEQ ID NO: 28            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 28
gcggagtcca ctgacttcat                                                   20

SEQ ID NO: 29            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 29
gtatcaccat gggcttcgtt                                                   20

SEQ ID NO: 30            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 30
cacaagcttc caaagcaaca                                                   20

SEQ ID NO: 31            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 31
gacgacgacg atgacgatga                                                   20

SEQ ID NO: 32            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 32
atcccaaacc catcggaacc                                                   20

SEQ ID NO: 33            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 33
tctggaactc gccattctcg                                                   20

SEQ ID NO: 34            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 34
aaccttccac aatccggtcc                                                   20
```

```
SEQ ID NO: 35            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 35
gtgaggacag tgccacagaa                                                     20

SEQ ID NO: 36            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 36
tgcacccta cccttttcag                                                      20

SEQ ID NO: 37            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 37
caccggtaat gcttccgcta                                                     20

SEQ ID NO: 38            moltype = DNA   length = 22
FEATURE                  Location/Qualifiers
misc_feature             1..22
                         note = Description of Artificial Sequence: Synthetic primer
source                   1..22
                         mol_type = other DNA
                         organism = synthetic construct
SEQUENCE: 38
ggctacggca gcagcggcgc gg                                                  22

SEQ ID NO: 39            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 39
ttggtgacct gtttggatga                                                     20

SEQ ID NO: 40            moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 40
ccaggcgttg ttgaggtatt                                                     20
```